United States Patent
Du et al.

(10) Patent No.: US 11,866,513 B2
(45) Date of Patent: *Jan. 9, 2024

(54) ANTI-TMPRSS6 ANTIBODIES AND USES THEREOF

(71) Applicant: MABWELL THERAPEUTICS INC., La Jolla, CA (US)

(72) Inventors: Xin Du, La Jolla, CA (US); Buxin Chen, San Marcos, CA (US); Yu Jean Wang, San Diego, CA (US)

(73) Assignee: MABWELL THERAPEUTICS, INC., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/329,172

(22) Filed: Jun. 5, 2023

(65) Prior Publication Data

US 2023/0348623 A1 Nov. 2, 2023

Related U.S. Application Data

(63) Continuation of application No. 17/916,008, filed as application No. PCT/US2021/025775 on Apr. 5, 2021.

(60) Provisional application No. 63/158,265, filed on Mar. 8, 2021, provisional application No. 63/006,695, filed on Apr. 7, 2020.

(51) Int. Cl.
*C07K 16/40* (2006.01)
*A61P 7/06* (2006.01)
*C12N 15/63* (2006.01)

(52) U.S. Cl.
CPC .............. *C07K 16/40* (2013.01); *A61P 7/06* (2018.01); *C12N 15/63* (2013.01); *C07K 2317/565* (2013.01)

(58) Field of Classification Search
None
See application file for complete search history.

(56) References Cited

FOREIGN PATENT DOCUMENTS

| WO | 2008097461 A2 | 8/2008 |
|---|---|---|
| WO | 2013070786 A1 | 5/2013 |
| WO | 2014099391 A1 | 6/2014 |
| WO | 2016071701 A1 | 5/2016 |
| WO | 2020065252 A1 | 4/2020 |
| WO | 2021105389 A1 | 6/2021 |

OTHER PUBLICATIONS

Anonymous, "Anti-Matriptase 2 antibody—Catalytic domain (ab56182) Abcam", Jan. 1, 2016 (Jan. 1, 2016), p. 1-8, Retrieved from the Internet: URL:https://www.abcam.com/matriptase-2-antibody-catalytic-domain-ab56182.html.

Anonymous, "Matriptase 2 antibody | anti Matriptase 2 antibody | Biorbyr", Mar. 25, 2015 (Mar. 25, 2015), p. 1-4, Retrieved from the Internet: URL:https://www.biorbyt.com/matriptase-2-antibody-orb2471.html.

Camaschella C., "Treating iron overload" N Engl Journal Med 368(24):2325-7, Jun. 13, 2013, DOI: 10.1056/NEJMcibr1304338.

Du et al., Du, X. et al."The Serine Protease TMPRSS6 Is Required to Sense Iron Deficiency" Science 2008. 320: 1088-1092 (May 23, 2008), DOI: 10.1126/science.1157121. Retrieved as HHS Public Access Author Manuscript PMC2430097 URL: https://www.ncbi.nlm.nih.gov/pmc/articles/PMC2430097/.

Frydlova et al, "Effect of Erythropoietin, Iron Deficiency and Iron Overload on Liver Matriptase-2 (TMPRSS6) Protein Content in Mice and Rats", PLOS One Jan. 1, 2016 (Jan. 1, 2016), p. e0148540-e0148540, DOI: 10.1371/journal.pone.0148540.

Fung et al, "Manipulation of the hepcidin pathway for therapeutic purposes", Haematologica, vol. 98, No. 11, 01 Nov. 8, 2013 (Nov. 1, 2013), p. 1667-1676, DOI: 10.3324/haematol.2013.084624.

Guo et al.' "Reducing TMPRSS6 ameliorates hernochromatosis and beta-thalassemia in mice", Journal of Clinical Investigation, vol. 123, No. 4, Mar. 25, 2013 (Mar. 25, 2013), p. 1531-1541, XP055135245 DOI: 10.1172/JCI66969.

International Preliminary Report on Patentability (IPRP) for International Patent Application No. PCT/US2021/025775 dated Oct. 6, 2022.

Lob et al. 2022, TMPRSS6 Inhibition with a Monoclonal Antibody Improves Red Blood Cell Health and Reduces Hepatic Iron Loading in Mouse Models of Iron Overload Diseases. American Society of Hematology (ASH) 64th ASH Annual Meeting and Exposition, Dec. 12, 2022.

Ramsay et al., "Matriptase-2 (TMPRSS6): a proteolytic regulator of iron homeostasis", Haematologica, Fondazione Ferrata Storti, IT, vol. 94, No. 6, Apr. 18, 2009 (Apr. 18, 2009), p. 840-849, DOI: 10.3324/HAEMATOL.2008.001867.

Schmidt et al., "An RNAi therapeutic targeting Tmprss6 decreases iron overload in Hfe-/-mice and ameliorates anemia and iron overload in murine beta-thalassemia intermedia", Blood, vol. 121, No. 7, Jan. 1, 2013 (Jan. 1, 2013), p. 1200-1208, DOI: 10.1182/blood-2012-09-453977.

Wake et al 2019 "KY1066: Generation and characterisation of a fully human antibody targeting the enzymatic activity of matriptase-2 for the treatment of iron overload in 13 thalassemia" Poster No. 3532, American Society of Hematology (ASH) 61st Annual Meeting, Dec. 9, 2019.

Wake Matihew et al, "Generation and Characterisation of KY1066, a Fully Human Antibody Targeting the Enzymatic Activity of Matriptase-2 for the Treatment of Iron Overload in Beta Thalassemia", Blood, American Society of Hematology, US, vol. 134, Nov. 13, 2019 (Nov. 13, 2019), p. 3532, Doi: 10.1182/BLOOD-2019-124075.

(Continued)

*Primary Examiner* — Sharon X Wen
(74) *Attorney, Agent, or Firm* — Neal, Gerber & Eisenberg LLP

(57) ABSTRACT

Antibodies and antigen-binding fragments thereof that bind type II transmembrane serine protease 6 (TMPRSS6) on the surface of a cell and increase hepcidin expression, and methods for treating disorders of iron metabolism using anti TMPRSS6 antibodies and fragments, are provided.

25 Claims, 19 Drawing Sheets
Specification includes a Sequence Listing.

(56) References Cited

OTHER PUBLICATIONS

Wang et al., "The role of TMPRSS6/matriptase-2 in iron regulation and anemia", Frontiers in Pharmacology May 19, 2014 (May 19, 2014), vol. 5, Retrieved from the Internet: URL:https://www.ncbi.nlm.nih.gov/pmc/articles/PMC4053654/pdf/fphar-05-00114.pdf, DOI: 10. 3389/fphar.2014.00114.
U.S. Appl. No. 17/916,008, filed Sep. 29, 2022.

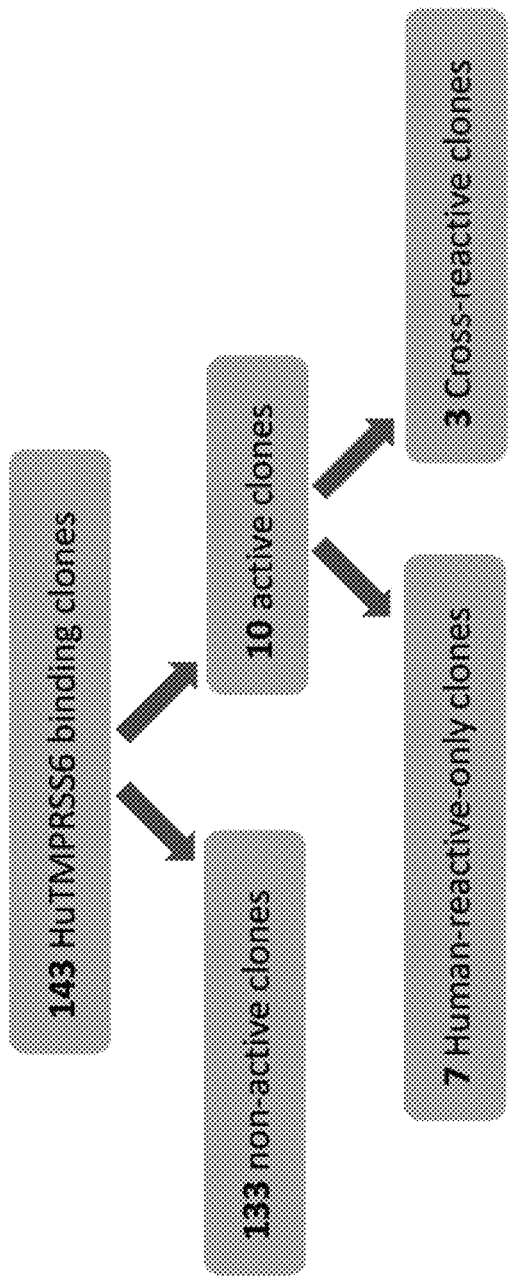
FIG. 1 Cascade screening for anti-TMPRSS6 antibodies.

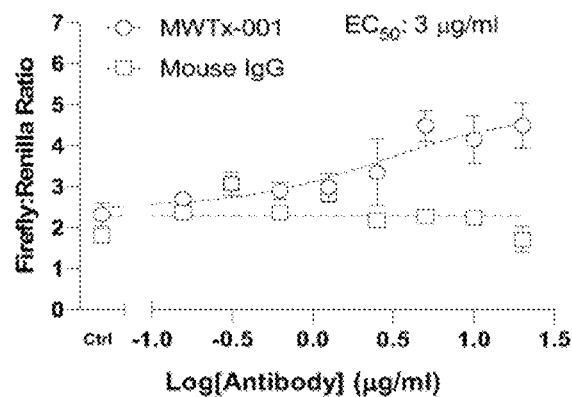
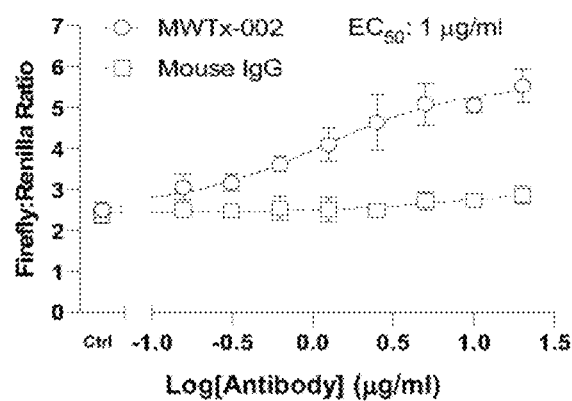
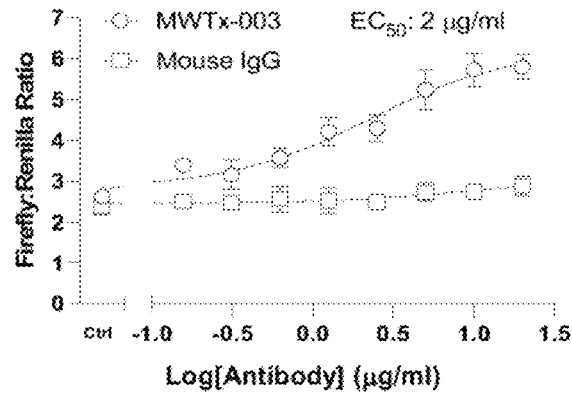

| | $K_D$ (M) | $k_{on}$ (1/Ms) | $k_{off}$ (1/s) | $R^2$ |
|---|---|---|---|---|
| MWTx-001 | 6.6e-10 | 2.08e+05 | 1.37e-04 | 0.9991 |
| MWTx-002 | 8.2e-10 | 1.46e+05 | 1.19e-04 | 0.9996 |
| MWTx-003 | 6.4e-09 | 2.42e+04 | 1.55e-04 | 0.9992 |
| hzMWTx-001Var | 3.36e-09 | 1.26e+05 | 4.23e-04 | 0.9999 |
| hzMWTx-002Var | 1.84e-08 | 5.95e+04 | 1.09e-03 | 0.9977 |
| hzMWTx-003Var | 1.37e-08 | 4.79e+03 | 6.58e-05 | 0.9996 |

FIG. 3M

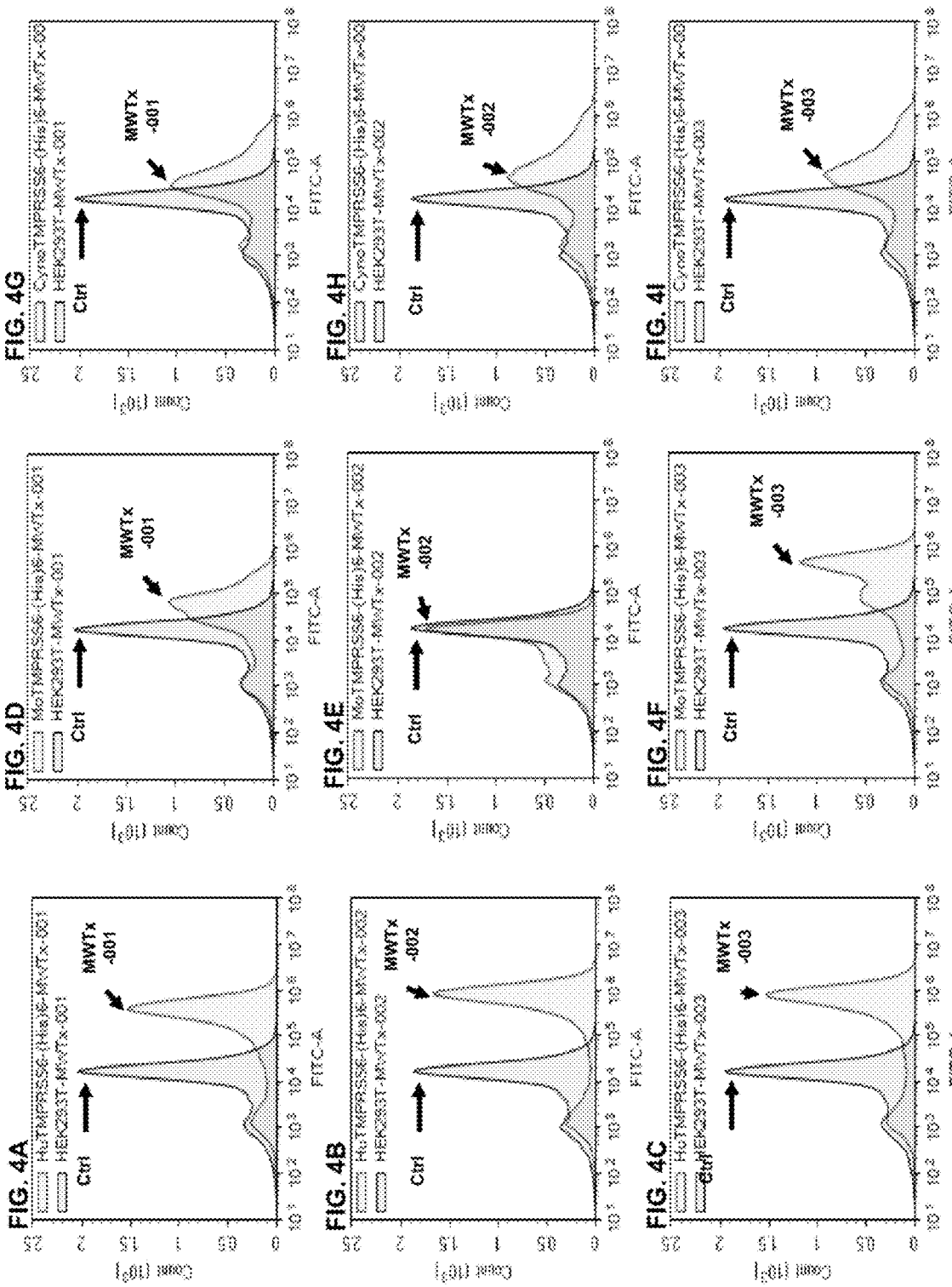

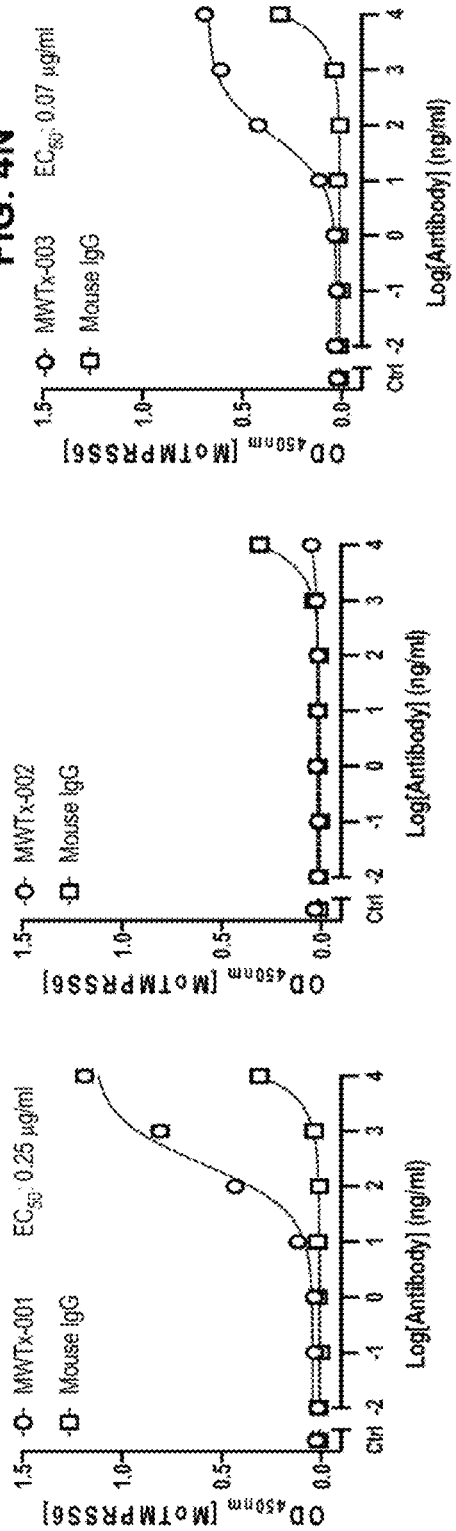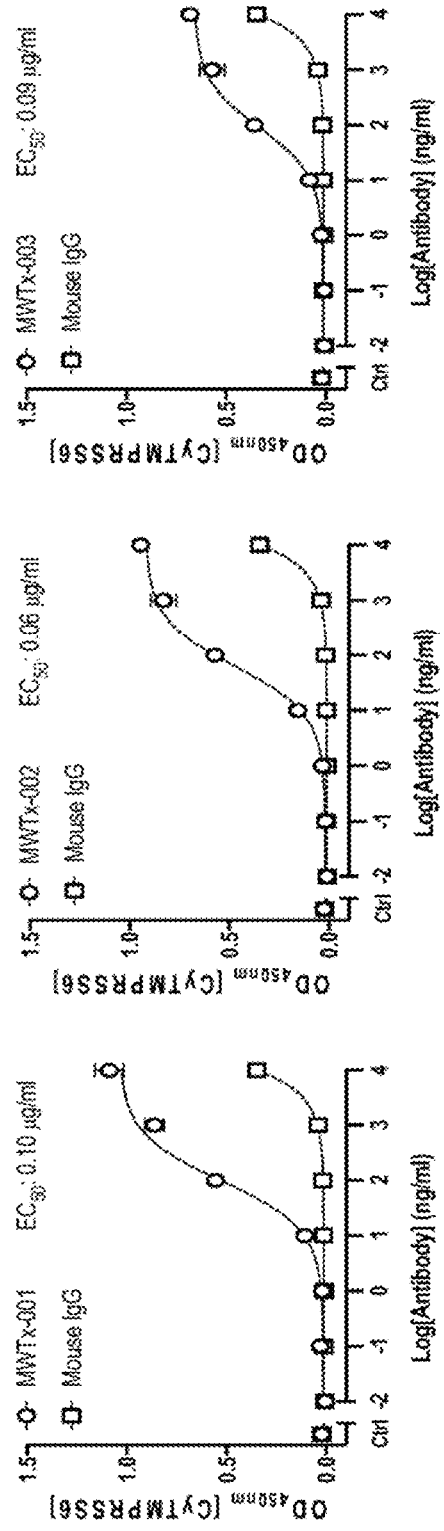

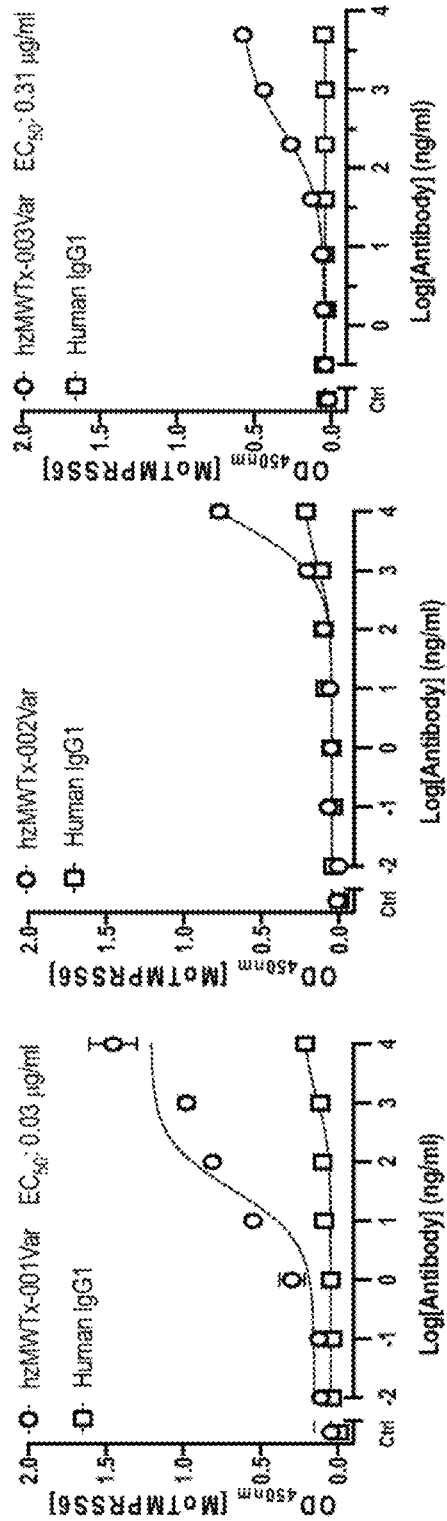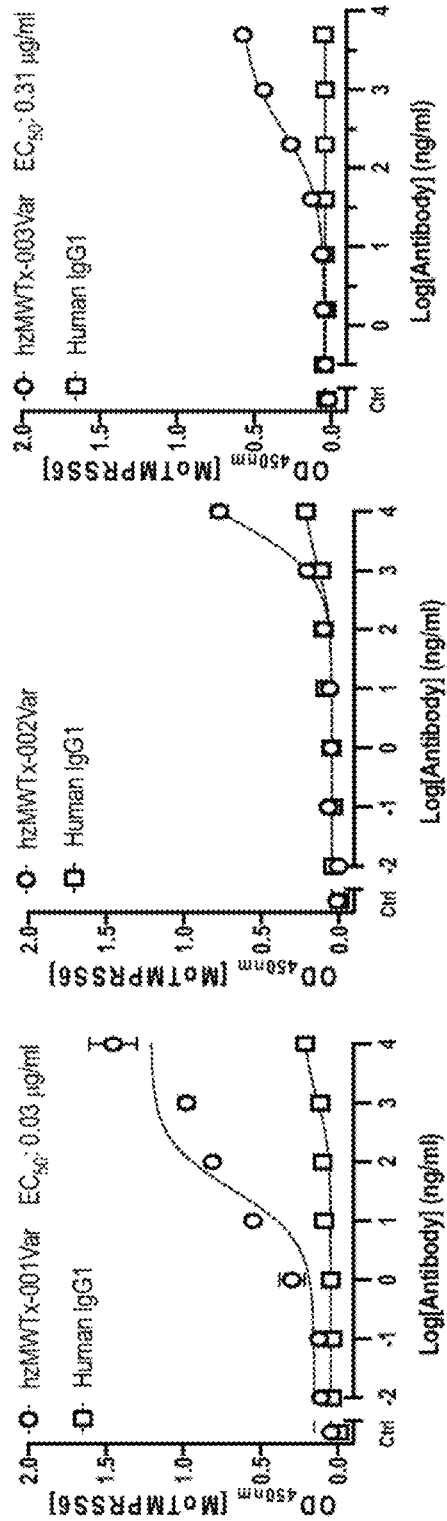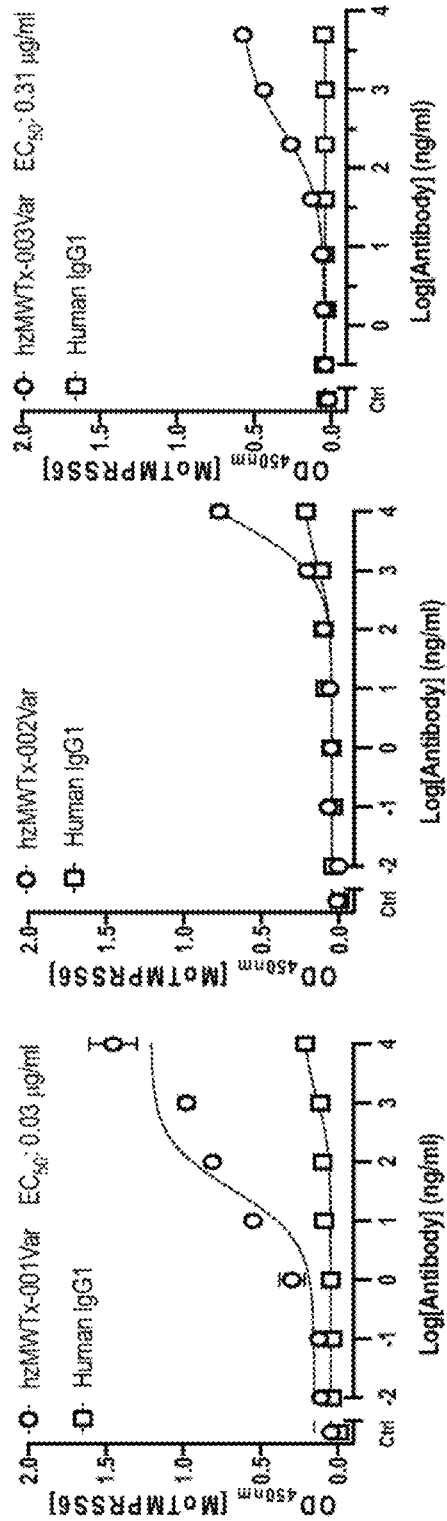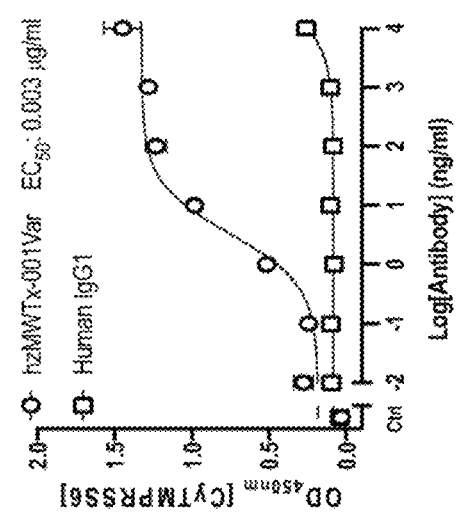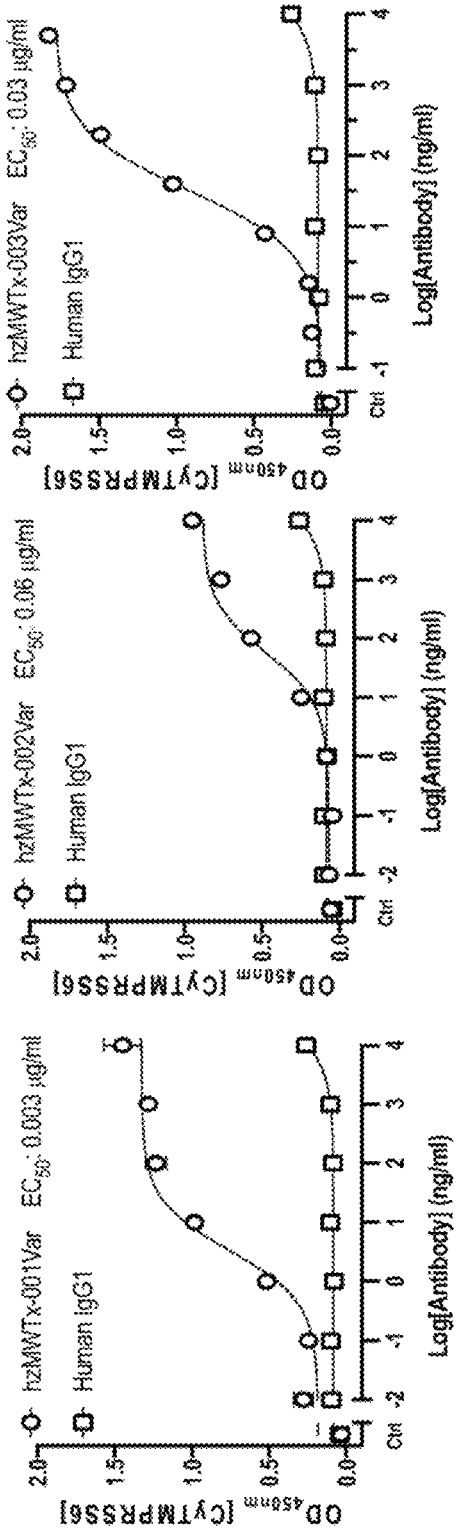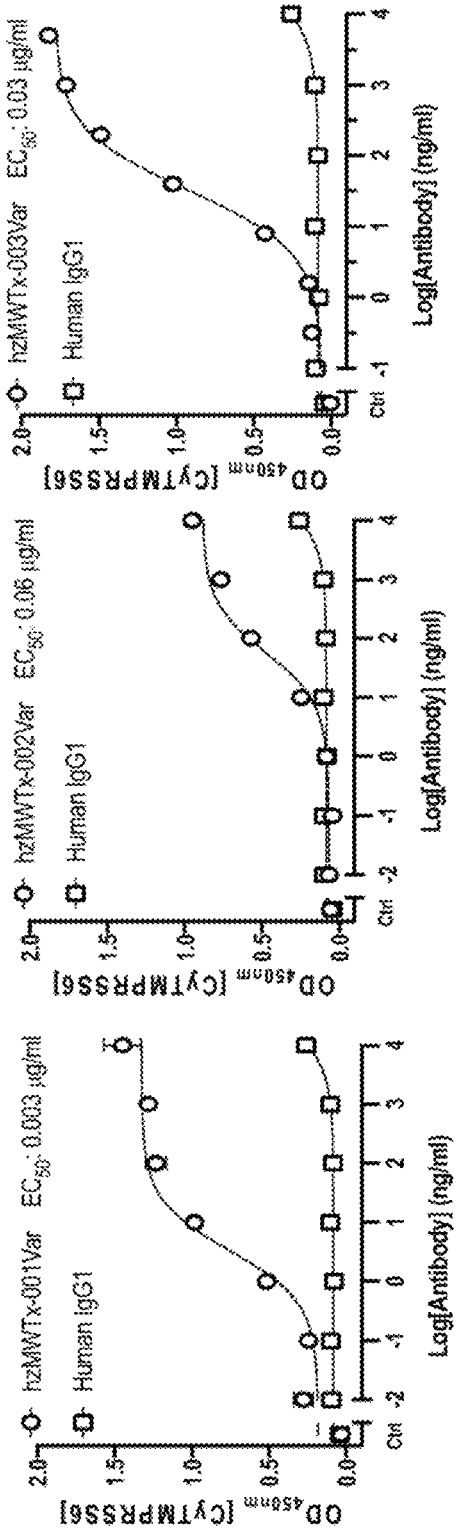

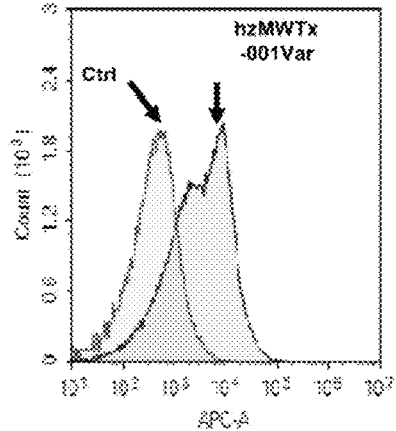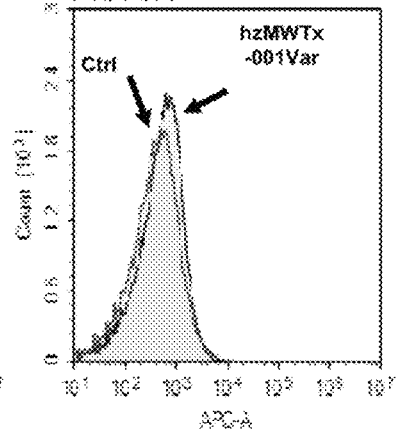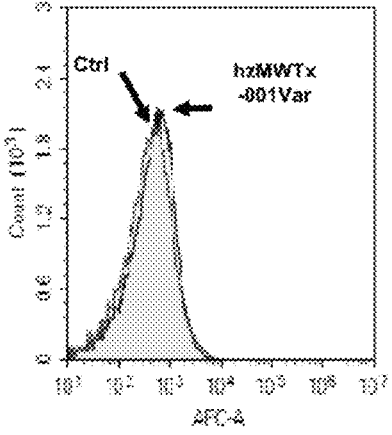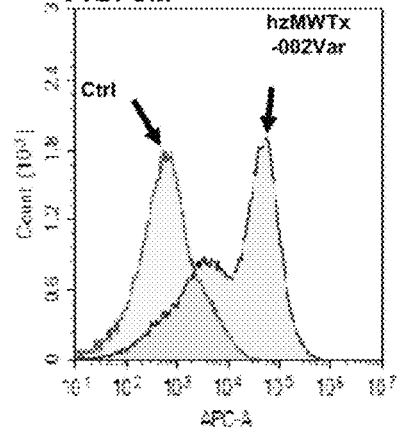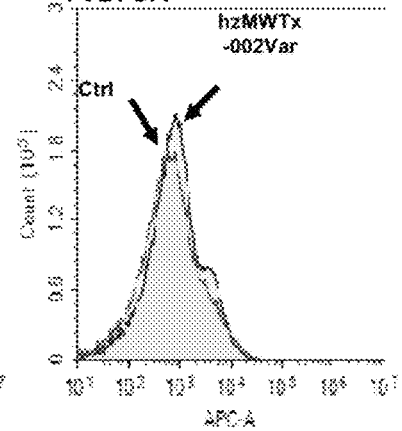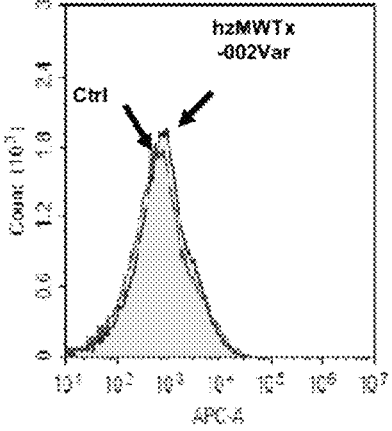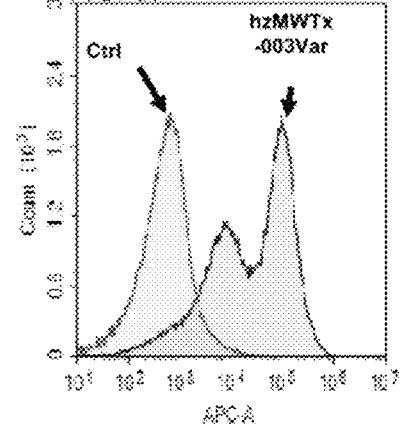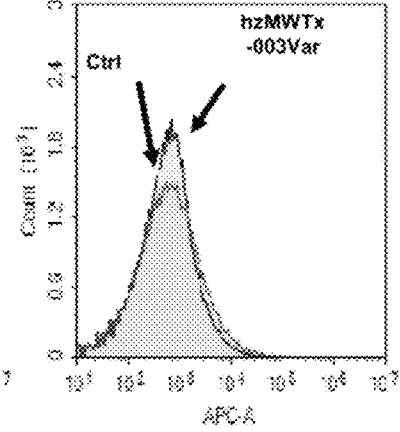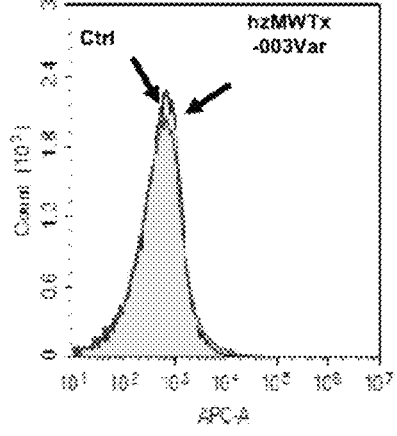

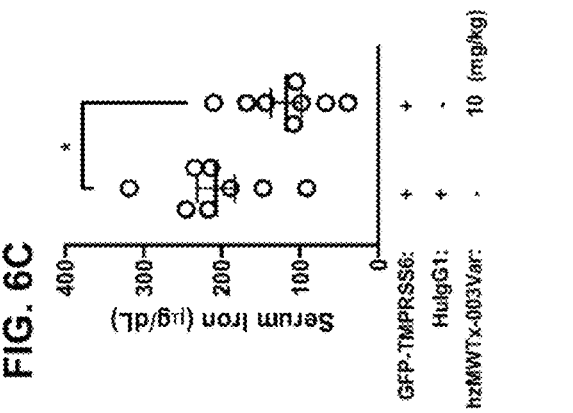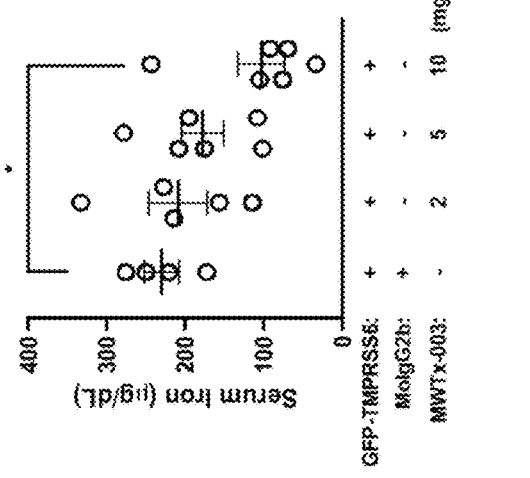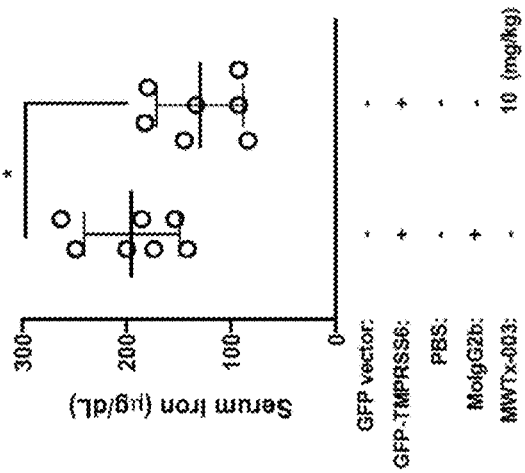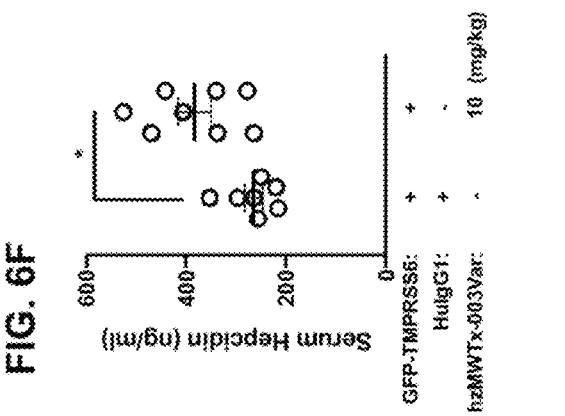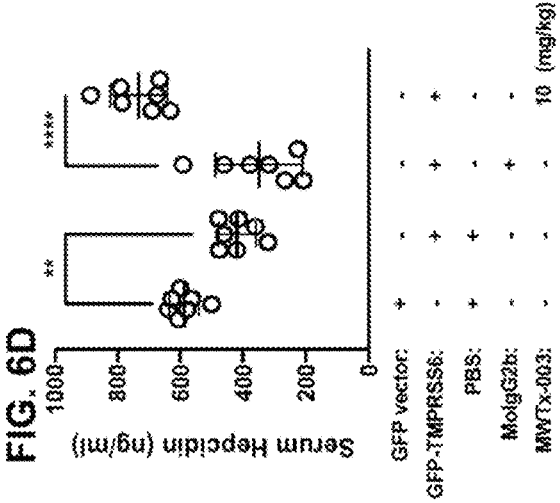

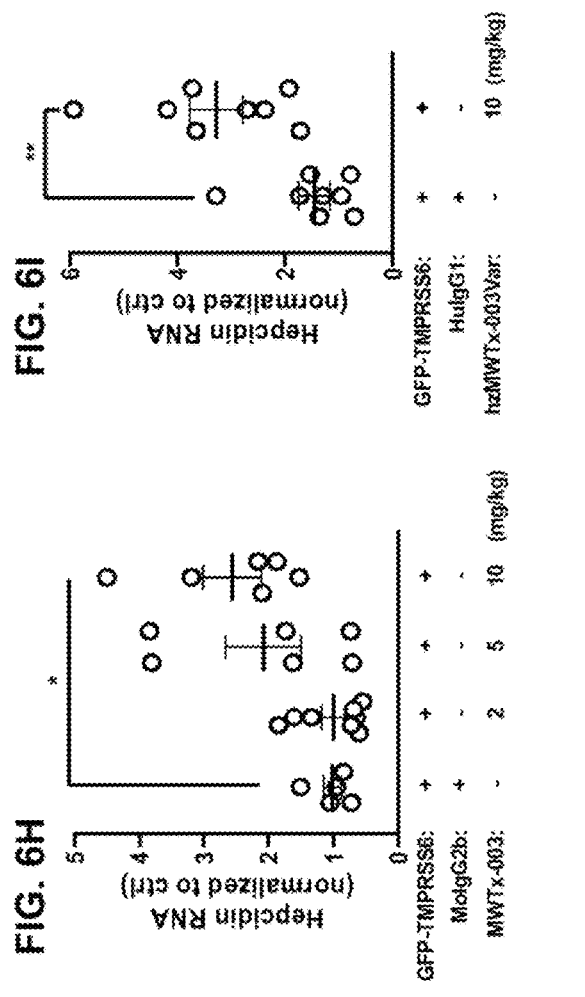
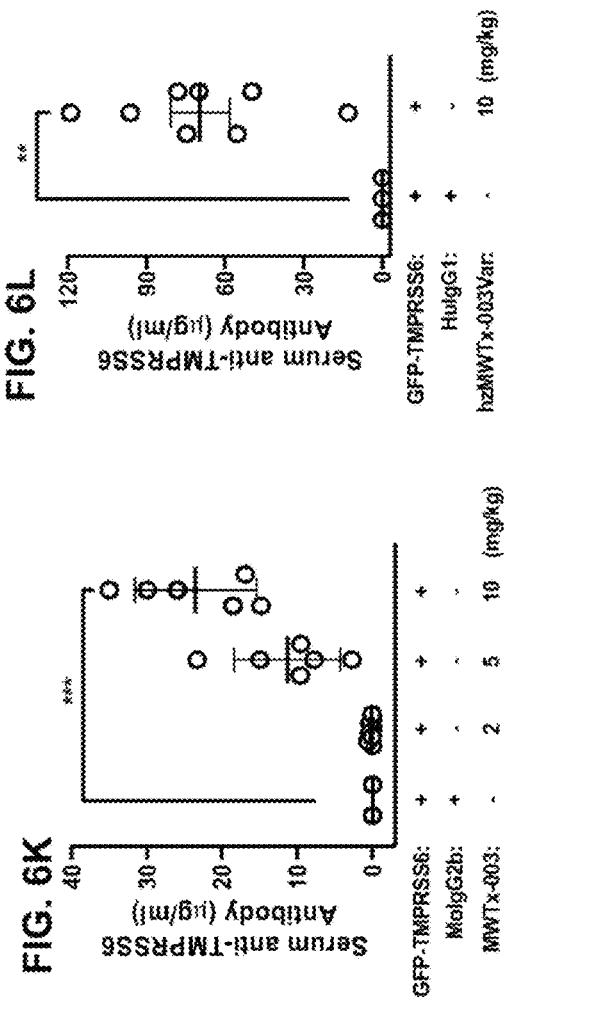

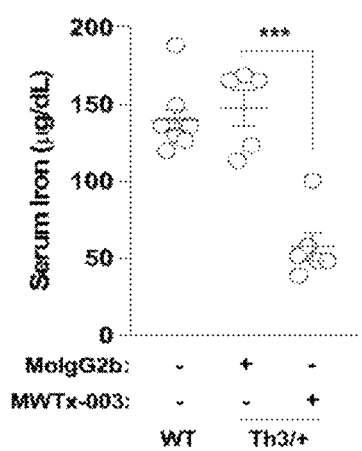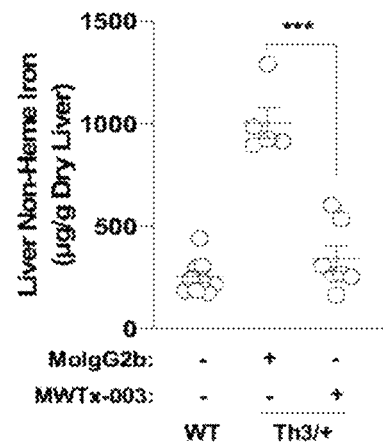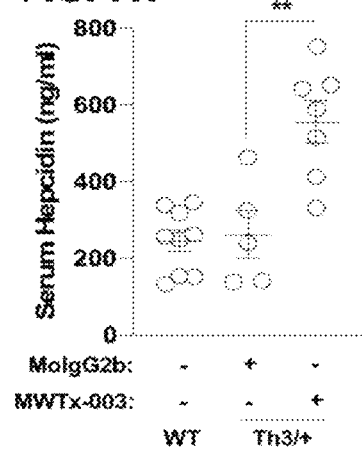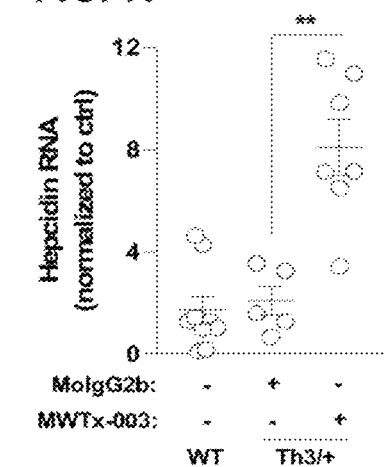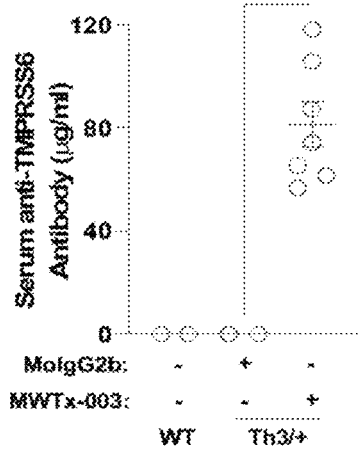

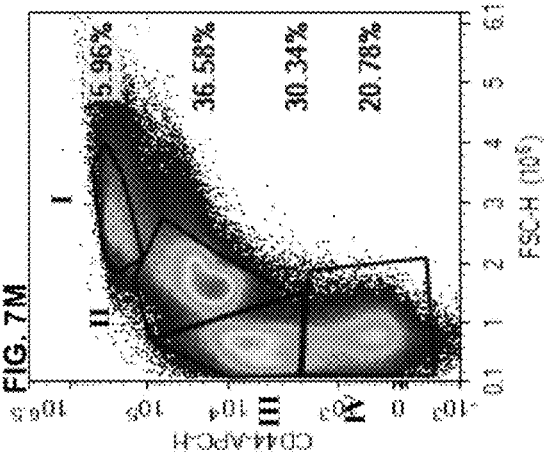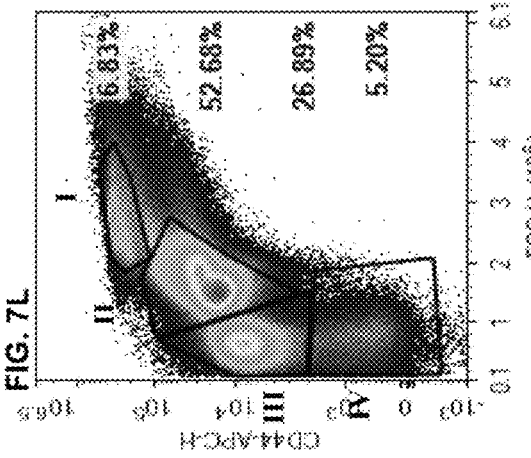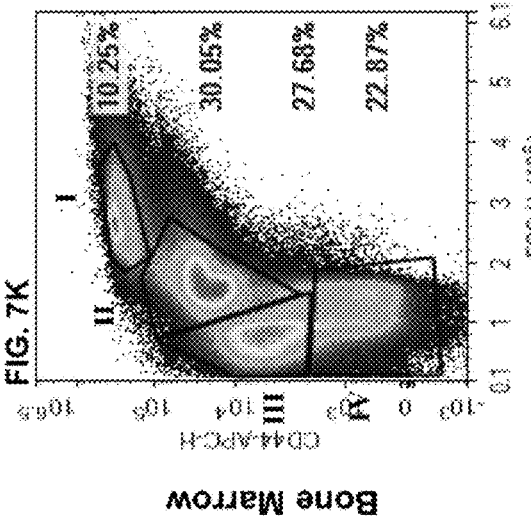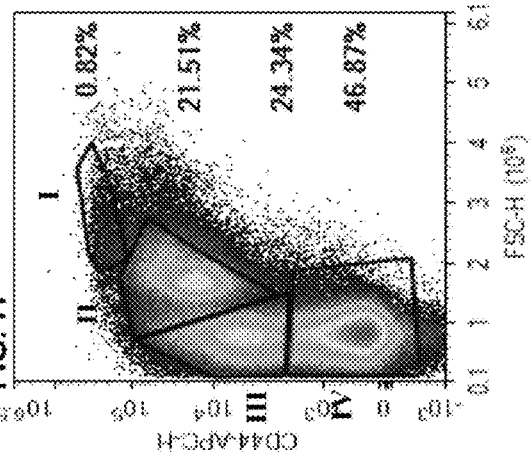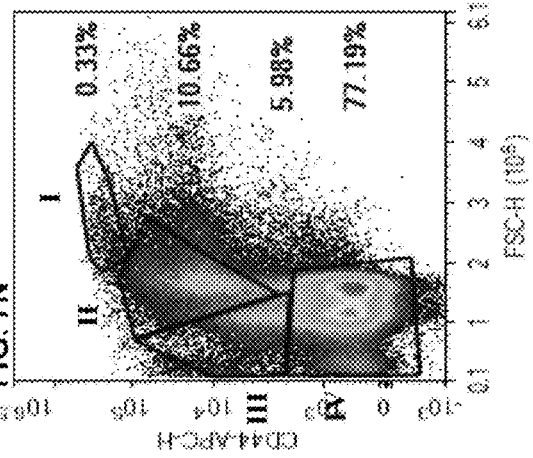

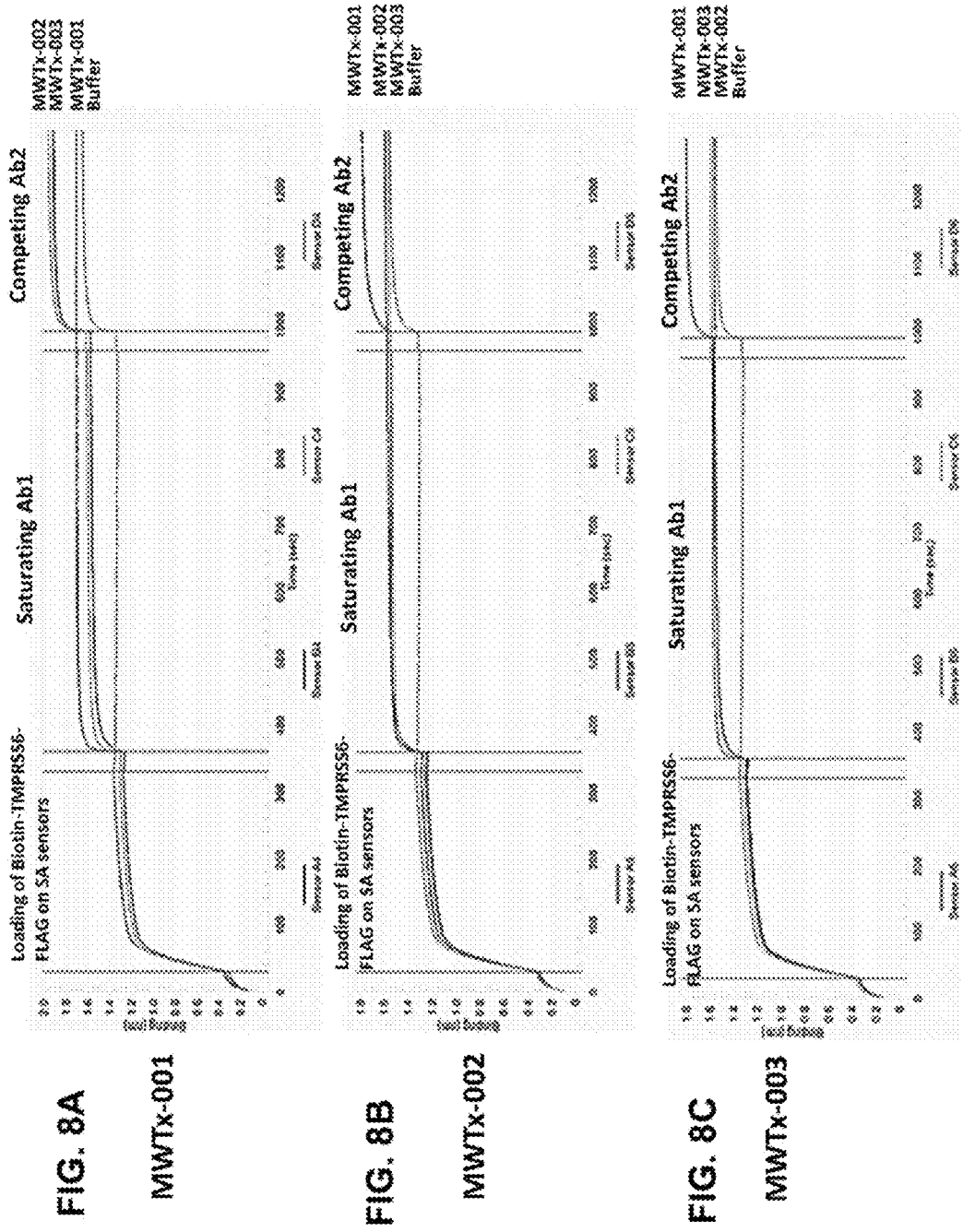

| Association Signal | MWTx-001 | MWTx-002 | MWTx-003 |
|---|---|---|---|
| MWTx-001 | 0.0065 | 0.2379 | 0.2327 |
| MWTx-002 | 0.3401 | 0.0100 | 0.0163 |
| MWTx-003 | 0.3391 | 0.0235 | 0.0190 |
| Buffer | 0.3017 | 0.2319 | 0.2369 |

FIG. 8D

ANTI-TMPRSS6 ANTIBODIES AND USES THEREOF

CROSS-REFERENCE TO RELATED APPLICATIONS

This application is a continuation of U.S. patent application Ser. No. 17/916,008, filed Sep. 29, 2022, as a national stage entry of International Application Number PCT/US2021/025775, filed on Apr. 5, 2021, which claims priority to U.S. Patent Application No. 63/158,265, filed Mar. 8, 2021, and U.S. Patent Application No. 63/006,695, filed Apr. 7, 2020. The contents of the aforementioned applications are incorporated herein by reference in their entireties.

SEQUENCE LISTING

The instant application contains a Sequence Listing which has been submitted electronically in XML format and is hereby incorporated by reference in its entirety. Said XML copy, created on Jun. 1, 2023, is named "033399-8011 Sequence Listing.xml" and is 137,190 bytes in size.

FIELD OF THE INVENTION

The present disclosure relates to antibodies and antigen-binding fragments that bind TMPRSS6, and treating disorders of iron metabolism using antibodies and antigen-binding fragments that bind TMPRSS6.

BACKGROUND

Type II transmembrane serine protease 6 (TMPRSS6) is encoded by the TMPRSS6 gene and primarily expressed in liver. The structure of TMPRSS6 includes a type II transmembrane domain, followed by a sea urchin sperm protein, enteropeptidase and agrin (SEA) domain, a stem region containing two complement factor C1r/C1s, urchin embryonic growth factor and bone morphogenetic protein (CUB) domains and three low-density lipoprotein receptor (LDLR) class A repeats, and a C-terminal trypsin-like serine protease domain (Wang, C.-Y. et al., *Front. Pharmacol*, 2014. 5:114). Aliases for TMPRSS6 (EC 3.4.21) include: matriptase-2; transmembrane protease serine 6; membrane-bound mosaic serine proteinase matriptase-2; and MT2.

TMPRSS6 plays a significant role in iron homeostasis through the BMP-SMAD signaling pathway that regulates the expression of hepcidin, a hormone that controls iron absorption and mobilization from iron stores. Hepcidin (also known as: HAMP (hepcidin anti-microbial protein or peptide), encoded by HAMP in humans and non-human primates, and Hamp in mice and rats) regulates systemic iron homeostasis by controlling the functional activity of the sole iron efflux channel ferroportin. Hepcidin can lower plasma iron levels by binding to ferroportin and causing internalization and degradation of the complex, thereby preventing iron absorption at the small intestine and release of stored iron. Chronic elevation of hepcidin levels causes systemic iron deficiency, and hepcidin deficiency causes systemic iron overload.

TMPRSS6 negatively regulates the production of hepcidin through a transmembrane signaling pathway that is triggered by iron deficiency and suppresses HAMP activation (Du, X. et al., *Science* 2008. 320: 1088-1092; Wang, C.-Y. et al., *Front. Pharmacol*, 2014. 5:114). Low blood iron levels trigger this pathway to reduce hepcidin production, which allows more iron from the diet to be absorbed through the intestines and transported out of storage sites into the bloodstream. In rats under acute iron deprivation, hepatic TMPRSS6 protein levels are upregulated, leading to suppressed hepcidin expression and production (Wang, C.-Y. et al., *Front. Pharmacol*. 2014. 5:114). Mutations throughout the TMPRSS6 molecule, and especially in the extracellular domain, have been identified in subjects with iron deficiency anemia, in particular iron-refractory iron deficiency anemia (IRIDA) that is unresponsive to oral iron treatment and only partially responsive to parenteral iron therapy (Wang, C.-Y. et al., *Front. Pharmacol*. 2014. 5:114). Loss-of-function mutations in TMPRSS6 in humans result in elevated levels of hepcidin and iron-deficiency anemia (Camaschella, C., *N Engl Journal Med* 2013. 168:24) as overproduction of hepcidin leads to defective iron absorption and utilization.

Iron overload disorders result when excess iron accumulates in tissues and organs to an extent that their normal functions are disrupted. Iron toxicity is a common complication of iron overload disorders, leading to high rates of mortality as a result of iron accumulation in major organs. β-thalassemia is an iron overload disorder that occurs when mutations in the HBB gene cause reduced or absent production of β-globin (beta globin) that lead to apoptosis of erythroblasts and a shortage of mature red blood cells, resulting in ineffective erythropoiesis that causes anemia and hyperabsorption of iron leading to iron toxicity. In patients with β-thalassemia, hepcidin is abnormally suppressed in relation to the patient's state of iron loading, creating a hepcidin deficiency that in turn allows excessive iron absorption and development of systemic iron overload. Ineffective erythropoiesis in other disorders such as MDS (myelodysplastic syndrome), dyserythropoietic anemia, sideroblastic anemia, is likewise characterized by low hepcidin leading to iron overload. Hemochromatosis, e.g., hemochromatosis type 1 or hereditary hemochromatosis is an iron overload disorder characterized by excess intestinal absorption of dietary iron and a pathological increase in total body iron stores. Current standards of care for treating iron overload disorders include blood transfusions for ineffective erythropoiesis that can further exacerbate iron overload, iron chelation with poor patient compliance, and phlebotomy or splenectomy to manage symptoms. Therapeutic approaches currently under development include gene therapy targeting the HBB gene, gene therapy and gene editing targeting other relevant genes, hepcidin mimetics, Fc-fusion proteins that target TGF superfamily ligands to inhibit SMAD signaling, antisense RNA drugs targeting TMPRSS6 (e.g., El-Beshlawy A., et al., *Blood Cells, Molecules and Diseases* 2019. 76: 53-58), and iRNA drugs targeting TMPRSS6.

SUMMARY

The invention relates to novel antibodies and antigen-binding fragments thereof that bind TMPRSS6, and methods of making and using antibodies and antigen-binding fragments thereof that bind TMPRSS6.

The present disclosure provides anti-TMPRSS6 antibodies, nucleic acids encoding anti-TMPRSS6 antibodies, and methods of making and using anti-TMPRSS6 antibodies. Anti-TMPRSS6 antibodies as disclosed herein encompass anti-TMPRSS6 antibodies and fragments thereof that are capable of binding TMPRSS6. Anti-TMPRSS6 antibodies as disclosed herein are capable of binding to human TMPRSS6 on the surface of a cell expressing human TMPRSS6. The present disclosure provides anti-TMPRSS6 antibodies for therapeutic and diagnostic uses. Anti-TMPRSS6 antibodies as disclosed herein can be used to treat disorders of iron metabolism such as iron overload disorders, in particular β-thalassemias including but not limited to non-transfusion dependent thalassemia, and other disorders of ineffective erythropoiesis.

In one aspect, anti-TMPRSS6 antibodies are provided that are capable of binding to TMPRSS6 on the surface of a cell expressing TMPRSS6 and modulating the activity of at least one component involved in iron metabolism, where a component may be a molecule or a biological process associated with the function of TMPRSS6. In certain embodiments, anti-TMPRSS6 antibodies disclosed herein are capable of modulating the activity of at least one component involved in regulating hepcidin expression. In certain embodiments, anti-TMPRSS6 antibodies disclosed herein are capable of substantially inhibiting TMPRSS6 suppression of hepcidin expression. In certain embodiments, anti-TMPRSS6 antibodies disclosed herein are capable of increasing hepcidin expression. In certain embodiments, anti-TMPRSS6 antibodies disclosed herein are capable of increasing the activity of the hepcidin promoter. In certain embodiments, anti-TMPRSS6 antibodies disclosed herein are capable of substantially inhibiting TMPRSS6 suppression of the BMP/SMAD pathway-induced expression of hepcidin. Anti-TMPRSS6 antibodies disclosed herein may modulate hepcidin expression, including but not limited to substantially inhibiting TMPRSS6 suppression of hepcidin expression, increasing hepcidin expression, increasing hepcidin promoter activity, or substantially inhibiting TMPRSS6 suppression of the BMP/SMAD pathway-induced expression of hepcidin, in a dose-dependent manner. In certain embodiments, anti-TMPRSS6 antibodies disclosed herein are capable of modulating hepcidin expression in a dose-dependent manner. In certain embodiments, anti-TMPRSS6 antibodies disclosed herein are capable of increasing serum hepcidin levels in a dose-dependent manner when administered to a subject.

In certain embodiments, anti-TMPRSS6 antibodies disclosed herein are capable of reducing serum iron levels in a dose-dependent manner when administered to a subject. In certain embodiments, anti-TMPRSS6 antibodies disclosed herein are capable of increasing liver hepcidin RNA levels in a dose-dependent manner when administered to a subject. In certain embodiments, anti-TMPRSS6 antibodies disclosed herein are capable of reducing liver non-heme iron, increasing serum hepcidin, increasing liver hepcidin RNA, reducing splenomegaly, increasing red blood count (RBC), increasing hematocrit (HCT), reducing red cell distribution width (RDW), and increased production of mature red cells (increased erythropoiesis) when administered to a subject known or suspected to have an iron overload disorder, in particular a β-thalassemia.

In another aspect, anti-TMPRSS6 antibodies disclosed herein show cross-reactivity with at least one non-human TMPRSS6. In certain embodiments, anti-TMPRSS6 antibodies disclosed herein are capable of binding to at least one non-human TMPRSS6 on the surface of a cell expressing the at least one non-human TMPRSS6. Anti-TMPRSS6 antibodies disclosed herein may be capable of binding human TMPRSS6 and mouse TMPRSS6. Anti-TMPRSS6 antibodies disclosed herein may be capable of binding to human TMPRSS6 and cynomolgus monkey TMPRSS6. Anti-TMPRSS6 antibodies disclosed herein may be capable of binding to each of human TMPRSS6, mouse TMPRSS6, and cynomolgus monkey TMPRSS6.

In another aspect, anti-TMPRSS6 antibodies disclosed herein specifically bind to TMPRSS6 (matriptase-2). In certain embodiments, anti-TMPRSS6 antibodies disclosed herein bind to TMPRSS6 (matriptase-2) and do not show detectable binding to matriptase homologues. In certain embodiments, anti-TMPRSS6 antibodies disclosed herein bind to human TMPRSS6 (matriptase-2) and do not show detectable binding to human matriptase-1 (ST14). In certain embodiments, anti-TMPRSS6 antibodies disclosed herein bind to human TMPRSS6 (matriptase-2) and do not show detectable binding to human matriptase-3 (TMPRSS7). In certain embodiments, anti-TMPRSS6 antibodies disclosed herein bind to human TMPRSS6 (matriptase-2) and do not show detectable binding to either of human matriptase-1 (ST14) or human matriptase-3 (TMPRSS7).

An anti-TMPRSS6 antibody disclosed herein may be a monoclonal antibody, a humanized antibody, a chimeric antibody, a single chain antibody, a Fab fragment, a single-chain variable fragment (scFv), a recombinant antibody, an aptamer, a single-domain antibody (VHH, nanobody), or other TMPRSS6-binding fragment or variant. In certain embodiments, an anti-TMPRSS6 antibody disclosed herein may comprise a framework in which amino acids have been substituted into an existing antibody framework, in particular to influence properties such as antigen-binding ability. In certain embodiments, an anti-TMPRSS6 antibody disclosed herein may comprise complementarity determining regions (CDRs) from a source (parental) antibody that have been grafted (fused) into a framework from a different type (class) of antibody and/or from a different organism than the parental antibody, in particular an acceptor human framework. In certain embodiments, an anti-TMPRSS6 antibody disclosed herein may comprise a framework in which amino acids have been substituted, mutated, or replaced in regions outside of the CDRs to influence properties such as antigen-binding or antibody structure, e.g., in the variable region framework surrounding the CDRs and/or in a constant region, in particular the Fc region. In certain embodiments, one or more of the CDRs have been substituted, mutated, or replaced. In certain embodiments, an anti-TMPRSS6 antibody disclosed herein may be a humanized anti-TMPRSS6 antibody variant.

In certain embodiments, anti-TMPRSS6 antibodies disclosed herein comprise at least one polypeptide having an amino acid sequence as set forth in Table 1, Table 2, or Table 3, or a sequence substantially identical (e.g., at least 85%, 90%, 92%, 95%, 97%, or 98%, 99% identical) to an amino acid sequence as set forth in Table 1, Table 2, or Table 3. Anti-TMPRSS6 antibodies disclosed herein may comprise at least one polypeptide having an amino acid sequence selected from the following, or a sequence substantially identical (e.g., at least 85%, 90%, 92%, 95%, 97%, or 98%, 99% identical) to at least one polypeptide having an amino acid sequence selected from the following: SEQ ID NO: 1; SEQ ID NO: 2; SEQ ID NO: 3; SEQ ID NO: 4; SEQ ID NO: 6; SEQ ID NO: 7; SEQ ID NO: 8; SEQ ID NO: 9; SEQ ID NO: 11; SEQ ID NO: 12; SEQ ID NO: 13; SEQ ID NO: 14; SEQ ID NO: 16; SEQ ID NO: 17; SEQ ID NO: 18; SEQ ID NO: 19; SEQ ID NO: 21; SEQ ID NO: 22; SEQ ID NO: 23; SEQ ID NO: 24; SEQ ID NO: 26; SEQ ID NO: 27; SEQ ID NO: 28; SEQ ID NO: 29; SEQ ID NO: 31; SEQ ID NO: 32; SEQ ID NO: 33; SEQ ID NO: 34; SEQ ID NO: 36; SEQ ID NO: 37; SEQ ID NO: 38; SEQ ID NO: 39; SEQ ID NO: 41; SEQ ID NO: 42; SEQ ID NO: 43; SEQ ID NO: 44; SEQ ID NO: 46; SEQ ID NO: 47; SEQ ID NO: 48; SEQ ID NO: 49; SEQ ID NO: 51; SEQ ID NO: 52; SEQ ID NO: 53; SEQ ID NO: 54; SEQ ID NO: 56; SEQ ID NO: 57; SEQ ID NO: 58; SEQ ID NO: 59; SEQ NO: 61; SEQ ID NO: 63; SEQ ID NO: 65; SEQ ID NO: 67; SEQ ID NO: 69; SEQ ID NO: 71;

SEQ ID NO: 73; SEQ ID NO: 75; SEQ ID NO: 77; SEQ ID NO: 79; SEQ ID NO: 81; or SEQ ID NO: 83.

In one embodiment, an anti-TMPRSS6 antibody disclosed herein comprises a heavy chain (HC) variable region polypeptide of the amino acid sequence set forth in SEQ ID NO: 1 or a sequence substantially identical to SEQ ID NO: 1, and a light chain (LC) variable region polypeptide of the amino acid sequence set forth in SEQ ID NO: 6 or a sequence substantially identical to SEQ ID NO: 6. In one embodiment, an anti-TMPRSS6 antibody disclosed herein comprises a heavy chain complementarity determining region 1 (HC CDR1) of the amino acid sequence set forth in SEQ ID NO: 2, a heavy chain complementarity determining region 2 (HC CDR2) of the amino acid sequence set forth in SEQ ID NO: 3, a heavy chain complementarity determining region 3 (HC CDR3) of the amino acid sequence set forth in SEQ ID NO: 4; a light chain complementarity determining region 1 (LC CDR1) of the amino acid sequence set forth in SEQ ID NO: 7, a light chain complementarity determining region 2 (LC CDR2) of the amino acid sequence set forth in SEQ ID NO: 8, and a light chain complementarity determining region 3 (LC CDR3) of the amino acid sequence set forth in SEQ ID NO: 9; or a variant of said antibody comprising 1, 2, 3, 4, 5, or 6 amino acid substitutions in the CDR regions. In one non-limiting embodiment, an anti-TMPRSS6 antibody disclosed herein is the antibody identified herein as MWTx-001, comprising an HC polypeptide having the amino acid sequence set forth in SEQ ID NO: 61 and an LC polypeptide having the amino acid sequence set forth in SEQ ID NO: 63.

In one embodiment, an anti-TMPRSS6 antibody disclosed herein comprises an HC variable region polypeptide of the amino acid sequence set forth in SEQ ID NO: 11 or a sequence substantially identical to SEQ ID NO: 11, and an LC variable region polypeptide of the amino acid sequence set forth in SEQ ID NO: 16 or a sequence substantially identical to SEQ ID NO: 16. In one embodiment, an anti-TMPRSS6 antibody disclosed herein comprises an HC CDR1 of the amino acid sequence set forth in SEQ ID NO: 12, an HC CDR2 of the amino acid sequence set forth in SEQ ID NO: 13, an HC CDR3 of the amino acid sequence set forth in SEQ ID NO: 14; an LC CDR1 of the amino acid sequence set forth in SEQ ID NO: 17, an LC CDR2 of the amino acid sequence set forth in SEQ ID NO: 18, and an LC CDR3 of the amino acid sequence set forth in SEQ ID NO: 19, or a variant of said antibody comprising 1, 2, 3, 4, 5, or 6 amino acid substitutions in the CDR regions. In one non-limiting embodiment, an anti-TMPRSS6 antibody disclosed herein is of the antibody identified herein as MWTx-002, comprising an HC polypeptide having the amino acid sequence set forth in SEQ ID NO: 65 and an LC polypeptide having the amino acid sequence set forth in SEQ ID NO: 67.

In one embodiment, an anti-TMPRSS6 antibody disclosed herein comprises an HC variable region polypeptide of the amino acid sequence set forth in SEQ ID NO: 21 or a sequence substantially identical to SEQ ID NO: 21, and an LC variable region polypeptide of the amino acid sequence set forth in SEQ ID NO: 26 or a sequence substantially identical to SEQ ID NO: 26. In one embodiment, an anti-TMPRSS6 antibody disclosed herein comprises an HC CDR1 of the amino acid sequence set forth in SEQ ID NO: 22, an HC CDR2 of the amino acid sequence set forth in SEQ ID NO: 23, an HC CDR3 of the amino acid sequence set forth in SEQ ID NO: 24; an LC CDR1 of the amino acid sequence set forth in SEQ ID NO: 27, an LC CDR2 of the amino acid sequence set forth in SEQ ID NO: 28, and an LC CDR3 of the amino acid sequence set forth in SEQ ID NO: 29, or a variant of said antibody comprising 1, 2, 3, 4, 5, or 6 amino acid substitutions in the CDR regions. In one non-limiting embodiment, an anti-TMPRSS6 antibody disclosed herein is the antibody identified herein as MWTx-003, comprising an HC polypeptide having the amino acid sequence set forth in SEQ ID NO: 69 and an LC polypeptide having the amino acid sequence set forth in SEQ ID NO: 71.

In one embodiment, an anti-TMPRSS6 antibody disclosed herein comprises an HC variable region polypeptide of the amino acid sequence set forth in SEQ ID NO: 31 or a sequence substantially identical to SEQ ID NO: 31, and an LC variable region polypeptide of the amino acid sequence set forth in SEQ ID NO: 36 or a sequence substantially identical to SEQ ID NO: 36. In one embodiment, an anti-TMPRSS6 antibody disclosed herein comprises an HC CDR1 of the amino acid sequence set forth in SEQ ID NO: 32, an HC CDR2 of the amino acid sequence set forth in SEQ ID NO: 33, an HC CDR3 of the amino acid sequence set forth in SEQ ID NO: 34; an LC CDR1 of the amino acid sequence set forth in SEQ ID NO: 37, an LC CDR2 of the amino acid sequence set forth in SEQ ID NO: 38, and an LC CDR3 of the amino acid sequence set forth in SEQ ID NO: 39, or a variant of said antibody comprising 1, 2, 3, 4, 5, or 6 amino acid substitutions in the CDR regions. In one non-limiting embodiment, an anti-TMPRSS6 antibody disclosed herein is the antibody identified herein as humanized anti-TMPRSS6 antibody variant hzMWTx-001Var, comprising an HC polypeptide having the amino acid sequence set forth in SEQ ID NO: 73 and an LC polypeptide having the amino acid sequence set forth in SEQ ID NO: 75.

In one embodiment, an anti-TMPRSS6 antibody disclosed herein comprises an HC variable region polypeptide of the amino acid sequence set forth in SEQ ID NO: 41 or a sequence substantially identical to SEQ ID NO: 41, and an LC variable region polypeptide of the amino acid sequence set forth in SEQ ID NO: 46 or a sequence substantially identical to SEQ ID NO: 46. In one embodiment, an anti-TMPRSS6 antibody disclosed herein comprises an HC CDR1 of the amino acid sequence set forth in SEQ ID NO: 42, an HC CDR2 of the amino acid sequence set forth in SEQ ID NO: 43, an HC CDR3 of the amino acid sequence set forth in SEQ ID NO: 44; an LC CDR1 of the amino acid sequence set forth in SEQ ID NO: 47, an LC CDR2 of the amino acid sequence set forth in SEQ ID NO: 48, and an LC CDR3 of the amino acid sequence set forth in SEQ ID NO: 49, or a variant of said antibody comprising 1, 2, 3, 4, 5, or 6 amino acid substitutions in the CDR regions. In one non-limiting embodiment, an anti-TMPRSS6 antibody disclosed herein is the antibody identified herein as humanized anti-TMPRSS6 antibody variant hzMWTx-002Var, comprising an HC polypeptide having the amino acid sequence set forth in SEQ ID NO: 77 and an LC polypeptide having the amino acid sequence set forth in SEQ ID NO: 79.

In one embodiment, an anti-TMPRSS6 antibody disclosed herein comprises an HC variable region polypeptide of the amino acid sequence set forth in SEQ ID NO: 51 or a sequence substantially identical to SEQ ID NO: 51, and an LC variable region polypeptide of the amino acid sequence set forth in SEQ ID NO: 56 or a sequence substantially identical to SEQ ID NO: 56. In one embodiment, an anti-TMPRSS6 antibody disclosed herein comprises an HC CDR1 of the amino acid sequence set forth in SEQ ID NO: 52, an HC CDR2 of the amino acid sequence set forth in SEQ ID NO: 53, an HC CDR3 of the amino acid sequence set forth in SEQ ID NO: 54; an LC CDR1 of the amino acid sequence set forth in SEQ ID NO: 57, an LC CDR2 of the amino acid sequence set forth in SEQ ID NO: 58, and an LC CDR3 of the amino acid sequence set forth in SEQ ID NO: 59, or a variant of said antibody comprising 1, 2, 3, 4, 5, or 6 amino acid substitutions in the CDR regions. In one non-limiting embodiment, an anti-TMPRSS6 antibody disclosed herein is the antibody identified herein as humanized anti-TMPRSS6 antibody variant hzMWTx-003Var, comprising an HC polypeptide having the amino acid sequence set forth in SEQ ID NO: 81 and an LC polypeptide having the amino acid sequence set forth in SEQ ID NO: 83.

In another aspect, anti-TMPRSS6 antibodies (including variants and fragments as disclosed herein) are provided that can be used to treat disorders of iron metabolism such as iron overload disorders, in particular β-thalassemia and other disorders of ineffective erythropoiesis. Methods and compositions are provided for using anti-TMPRSS6 antibodies as disclosed herein for therapeutic uses including, but not limited to, treating disorders of iron metabolism such as iron overload disorders, in particular β-thalassemia and other disorders of ineffective erythropoiesis. In certain embodiments, pharmaceutical compositions comprising an anti-TMPRSS6 antibody disclosed herein and a suitable carrier and/or excipient are provided.

In another aspect, methods for treating a disorder of iron metabolism are provided, such methods comprising administering an effective amount of an anti-TMPRSS6 antibody disclosed herein to a subject in need thereof, wherein administration of the effective amount of anti-TMPRSS6 antibody modulates the activity of a component involved in iron metabolism. In certain embodiments, methods for treating an iron overload disorder comprise administering an effective amount of an anti-TMPRSS6 antibody disclosed herein, wherein administration of the effective amount of anti-TMPRSS6 antibody modulates the activity of a component involved in iron metabolism. In certain embodiments, methods for treating an iron overload disorder comprise administering an effective amount of an anti-TMPRSS6 antibody disclosed herein, wherein administration of the effective amount of anti-TMPRSS6 antibody modulates the activity of at least one component involved in regulating hepcidin expression. In certain embodiments, methods comprise administration of an effective amount of anti-TMPRSS6 antibody that inhibits TMPRSS6 suppression of hepcidin expression. In certain embodiments, administration of the effective amount of anti-TMPRSS6 antibody increases hepcidin expression. In certain embodiments, methods comprise administration of an effective amount of anti-TMPRSS6 antibody that increases the activity of the hepcidin promoter. In certain embodiments, methods comprise administration of an effective amount of anti-TMPRSS6 antibody that inhibits TMPRSS6 suppression of the BMP/SMAD pathway-induced expression of hepcidin. In certain embodiments, methods comprise administration of an effective amount of anti-TMPRSS6 antibody to a subject that results in one or more biological effects associated with an iron overload disorder including but not limited to reducing serum iron, reducing liver non-heme iron, increasing serum hepcidin, increasing liver hepcidin RNA, reducing splenomegaly, increasing red blood count (RBC), increasing hematocrit (HCT), reducing red cell distribution width (RDW), and/or increased production of mature red cells (increased erythropoiesis).

In another aspect, methods for treating a disease or disease state in which abnormal suppression of hepcidin expression is involved are provided, such methods comprising administering an effective amount of an anti-TMPRSS6 antibody disclosed herein to a subject in need thereof, wherein administration of the effective amount of anti-TMPRSS6 antibody modulates the activity of at least one component involved in abnormal suppression of hepcidin expression and reduces abnormal suppression of hepcidin expression. In particular embodiments, the method results in increased hepcidin expression.

In another aspect, methods for treating a disorder of iron metabolism associated with suppressed hepcidin levels are provided, such methods comprising administering an effective amount of an anti-TMPRSS6 antibody disclosed herein to a subject in need thereof, wherein administration of the effective amount of anti-TMPRSS6 antibody modulates the activity of at least one component involved in suppression of hepcidin levels. In certain embodiments, methods comprise administration of an effective amount of anti-TMPRSS6 antibody that increases serum hepcidin levels, increases liver hepcidin RNA, and lowers serum iron levels.

In another aspect, methods are provided for treating disorders of iron metabolism including disorders related to and/or characterized by ineffective erythropoiesis that may include but are not limited to β-thalassemia. In accordance with this aspect, such methods comprise administering an effective amount of an anti-TMPRSS6 antibody disclosed herein to a subject that is known or suspected of having a disorder of iron metabolism related to and/or characterized by ineffective erythropoiesis, wherein administration results in one or more changes related to iron metabolism and/or erythropoiesis in the subject. In certain embodiments, methods are provided wherein administration of the effective amount of anti-TMPRSS6 antibody treats or ameliorates at least one biological effect or symptom associated with the disorder. In particular embodiments, practicing the method results in one or more changes including but not limited to reducing liver non-heme iron, increasing serum hepcidin, increasing liver hepcidin RNA, reducing splenomegaly, increasing red blood count (RBC), increasing hematocrit (HCT), reducing red cell distribution width (RDW), and increased production of mature red cells (increased erythropoiesis).

In another aspect, methods for diagnosing or screening for an iron overload disorder in a subject are provided. In certain embodiments, methods comprise administering anti-TMPRSS6 antibody to a subject known or suspected to have an iron overload disorder and measuring one or more biological effect or symptom associated with an iron overload disorder.

In another aspect, one or more isolated nucleic acid molecules are provided that encode at least a portion of at least one of the anti-TMPRSS6 antibodies disclosed herein. In certain embodiments, isolated nucleic acid molecules that encode at least a portion of at least one of the anti-TMPRSS6 antibodies disclosed herein comprise a nucleotide sequence as set forth in Table 1, Table 2, or Table 3, or a sequence substantially identical (e.g., at least 85%, 90%, 92%, 95%, 97%, or 98%, 99% identical) to a nucleotide sequence as set forth in Table 1, Table 2, or Table 3. In certain embodiments, isolated nucleic acid molecules that encode at least one of the heavy chain (HC) sequences of the anti-TMPRSS6 antibodies disclosed herein may comprise a nucleotide sequence selected from at least one of: SEQ ID NO: 5 or a sequence substantially identical to SEQ ID NO: 5; SEQ ID NO: 15 or a sequence substantially identical to SEQ ID NO: 15; SEQ ID NO. 25 or a sequence substantially identical to SEQ ID NO: 25: SEQ ID NO: 35 or a sequence substantially identical to SEQ ID NO: 35; SEQ ID NO: 45 or a sequence substantially identical to SEQ ID NO: 45; SEQ ID NO: 55 or a sequence substantially identical to SEQ ID NO: 55; SEQ ID NO: 62 or a sequence substantially identical to SEQ ID NO: 62; SEQ ID NO: 66 or a sequence substantially identical to SEQ ID NO: 66; SEQ ID NO: 70 or a sequence substantially identical to SEQ ID NO: 70; SEQ ID NO: 74 or a sequence substantially identical to SEQ ID NO: 74; SEQ ID NO: 78 or a sequence substantially identical to SEQ ID NO: 78, or SEQ ID NO: 82 or a sequence substantially identical to SEQ ID NO: 82. In certain embodiments, isolated nucleic acid molecules that encode at least one of the light chain (LC) sequences of the anti-TMPRSS6 antibodies or antigen-binding fragments thereof disclosed herein may comprise a nucleotide sequence selected from at least one of: SEQ ID NO: 10 or a sequence substantially identical to SEQ ID NO: 10; SEQ ID NO: 20 or a sequence substantially identical to SEQ ID NO: 20; or SEQ ID NO: 30 or a sequence substantially identical to SEQ ID NO: 30; SEQ ID NO: 40 or a sequence substantially identical to SEQ ID NO: 40; SEQ ID NO: 50 or a sequence substantially identical to SEQ ID NO: 50; SEQ ID NO: 60 or a sequence substantially identical to SEQ ID NO: 60; SEQ ID NO: 64 or a sequence substantially identical to SEQ ID NO: 64; SEQ ID NO: 68 or a sequence substantially identical to SEQ ID NO: 68; SEQ ID NO: 72 or a sequence substantially identical to SEQ ID NO: 72; SEQ ID NO: 76 or a sequence substantially identical to SEQ ID NO: 76; SEQ ID NO: 80 or a sequence substantially identical to SEQ ID NO: 80, or SEQ ID NO: 84 or a sequence substantially identical to SEQ ID NO: 84.

In another aspect, vector is provided comprising one or more nucleic acid molecules that encode at least one amino acid sequence of the anti-TMPRSS6 antibodies disclosed herein. In certain embodiments, a vector is provided comprising one or more nucleic acid molecules that encode at least one of the heavy chain (HC) or light chain (LC) sequences of the anti-TMPRSS6 antibodies disclosed herein. In certain embodiments, a vector is provided comprising nucleic acid molecules that encode at least a portion of at least one of the amino acid sequences as set forth in Table 1, Table 2, or Table 3, or at least a portion of an amino acid sequence substantially identical to an amino acid sequence as set forth in Table 1, Table 2, or Table 3. In certain embodiments, a vector is provided comprising nucleic acid molecules that encode at least a portion of at least one of the HC or LC sequences as set forth in Table 1, Table 2, or Table 3, or at least a portion of an amino acid sequence substantially identical to at least one of the HC or LC sequences as set forth in Table 1, Table 2, or Table 3.

In another aspect, at least one host cell is provided containing a vector comprising one or more nucleic acid molecules that encode amino acid sequences of the anti-TMPRSS6 antibodies disclosed herein. In certain embodiments, a host cell is provided containing a vector comprising nucleic acid molecules that encode at least a portion of at least one of the HC or LC sequences as set forth in Table 1, Table 2, or Table 3, or at least a portion of an amino acid sequence substantially identical to at least one of the HC or LC sequences as set forth in Table 1, Table 2, or Table 3. In certain embodiments, at least one host cell is capable of supporting vector expression and recombinant production of anti-TMPRSS6 antibodies or antigen-binding fragments thereof encoded by the vector. In certain embodiments, at least one host cell is capable of supporting vector expression and recombinant production of anti-TMPRSS6 antibodies or antigen-binding fragments thereof encoded by a vector comprising nucleic acid molecules that encode at least a portion of at least one of the HC or LC sequences as set forth in Table 1, Table 2, or Table 3, or at least a portion of an amino acid sequence substantially identical to at least one of the HC or LC sequences as set forth in Table 1, Table 2, or Table 3. In certain embodiments, host cells are transiently transfected with a vector comprising one or more nucleic acid molecules that encode amino acid sequences of the anti-TMPRSS6 antibodies or antigen-binding fragments thereof disclosed herein, wherein the host cells are capable of supporting vector expression and recombinant production of anti-TMPRSS6 antibodies or antigen-binding fragments thereof encoded by the vector.

BRIEF DESCRIPTION OF THE FIGURES

FIG. 1 shows results from cascade screening of anti-TMPRSS6 antibodies, where antibodies that bind to human TMPRSS6 were assessed using an in vitro functional assay for HAMP promoter activity, and antibodies that showed effects on HAMP promoter activity were assessed for cross-reactivity with non-human TMPRSS6.

FIGS. 2A-2F show effects of anti-TMPRSS6 antibodies on HAMP promoter activity measured by a dual luciferase reporter assay carried out in HepG2 cells, for a range of antibody concentrations. In each plot, open circles represent results using an anti-TMPRSS6 antibody, and open squares represents results using the same concentration of mouse IgG or human IgG1 as a negative (nonspecific binding) control. FIG. 2A shows effects of the MWTx-001 anti-TMPRSS6 antibody on HAMP promoter activity over a range of antibody concentrations. FIG. 2B shows effects of the MWTx-002 anti-TMPRSS6 antibody on HAMP promoter activity over a range of antibody concentrations. FIG. 2C shows effects of the MWTx-003 anti-TMPRSS6 antibody on HAMP promoter activity over a range of antibody concentrations. FIG. 2D shows effects of the hzMWTx-001Var anti-TMPRSS6 antibody on HAMP promoter activity over a range of antibody concentrations. FIG. 2E shows effects of the hzMWTx-002Var anti-TMPRSS6 antibody on HAMP promoter activity over a range of antibody concentrations. FIG. 2F shows effects of the hzMWTx-003Var anti-TMPRSS6 antibody on HAMP promoter activity over a range of antibody concentrations.

FIGS. 3A-3M show results of determinations of binding affinity of anti-TMPRSS6 antibodies. FIGS. 3A-3F show results of determinations of anti-TMPRSS6 antibody binding affinity for human TMPRSS6 expressed on HEK293T cells using two different methods. In each plot, open circles represent results using an anti-TMPRSS6 antibody over a range of concentrations, and open squares represents results using the same concentration of mouse IgG as a negative control. FIGS. 3A-3C show results using cell surface ELISA (measuring HRP-labelled secondary antibody) to measure binding of MWTx-001 (FIG. 3A), MWTx-002 (FIG. 3B), and MWTx-003 (FIG. 3C) to human TMPRSS6, with calculated EC50 values for each antibody used as an estimate of binding affinity. FIGS. 3D-3F show results using FACS (measuring APC-conjugated secondary antibody) to measure binding of MWTx-001 (FIG. 3D), MWTx-002 (FIG. 3E), and MWTx-003 (FIG. 3F) to human TMPRSS6, with calculated EC50 values for each antibody used as an estimate of binding affinity. FIGS. 3G-3M show results of determinations of anti-TMPRSS6 antibody affinity and binding kinetics for human ecto-TMPRSS6-FLAG using the Octet® RED96e with analyte concentrations of 50 nM, 25 nM, 12.5 nM, 6.25 nM, 3.13 nM, 1.56 nM and 0.78 nM. FIG. 3G shows binding kinetics of MWTx-001 anti-TMPRSS6 antibody towards ecto-TMPRSS6-FLAG. FIG. 3H shows binding kinetics of MWTx-002 anti-TMPRSS6 antibody towards ecto-TMPRSS6-FLAG. FIG. 3I shows binding kinetics of MWTx-003 anti-TMPRSS6 antibody towards ecto-TMPRSS6-FLAG. FIG. 3J shows binding kinetics of hzMWTx-001Var anti-TMPRSS6 antibody towards ecto-TMPRSS6-FLAG. FIG. 3K shows binding kinetics of hzMWTx-002Var anti-TMPRSS6 antibody towards ecto-TMPRSS6-FLAG. FIG. 3L shows binding kinetics of hzMWTx-003Var anti-TMPRSS6 antibody towards ecto-TMPRSS6-FLAG. FIG. 3M summaries affinity measurements of all anti-TMPRSS6 antibodies.

FIGS. 4A-4U show results of determinations of cross-reactivity of anti-TMPRSS6 antibodies. FIGS. 4A-4I show results of determinations of the cross-reactivity of anti-TMPRSS6 antibodies MWTx-001, MWTx-002, and MWTx-003 to human TMPRSS6 and non-human TMPRSS6 expressed on HEK293T cells. Each histogram plot shows FACS results for a single antibody incubated with HEK293T cells expressing a TMPRSS6 target (thinner line and lighter fill; indicated with antibody name) and the same antibody incubated with control HEK293T cells that do not express a TMPRSS6 protein (thicker line, darker fill; indicated with Ctrl). FIGS. 4A-4C show results using HEK293T cells stably expressing human TMPRSS6 (HuTMPRSS6-(His)$_6$) with MWTx-001 (FIG. 4A), MWTx-002 (FIG. 4B), and MWTx-003 (FIG. 4C). FIGS. 4D-4F show results using HEK293T cells stably expressing mouse TMPRSS6 (MoTMPRSS6-(His)$_6$) with MWTx-001 (FIG. 4D), MWTx-002 (FIG. 4E), and MWTx-003 (FIG. 4F). FIGS. 4G-4I show results using HEK293T cells transiently expressing cynomolgus monkey TMPRSS6 (CynoTMPRSS6-(His)$_6$) with MWTx-001 (FIG. 4G), MWTx-002 (FIG. 4H), and MWTx-003 (FIG. 4I). FIGS. 4J-4U show results of cross-reactivity of anti-TMPRSS6 antibodies to non-human (mouse (FIGS. 4J, 4L, 4N, 4P, 4R, 4T) or cynomolgus monkey (FIGS. 4K, 4M, 4O, 4Q, 4S, 4U)) TMPRSS6 expressed on HEK293T cells using cell surface ELISA (measuring HRP-labelled secondary antibody) to measure binding of MWTx-001 anti-TMPRSS6 antibody (FIGS. 4J-4K), MWTx-002 anti-TMPRSS6 antibody (FIGS. 4L-4M), MWTx-003 anti-TMPRSS6 antibody (FIGS. 4N-4O), hzMWTx-001Var anti-TMPRSS6 antibody (FIGS. 4P-4Q), hzMWTx-002Var anti-TMPRSS6 antibody (FIGS. 4R-4S) and hzMWTx-003Var anti-TMPRSS6 antibody (FIG. 4T-4U) to non-human TMPRSS6. In each plot, open circles represent results using an anti-TMPRSS6 antibody, and open squares represents results of mouse IgG or human IgG1 as a negative (nonspecific binding) control, with calculated EC50 values for each antibody used as an estimate of binding affinity.

FIGS. 5A-5R. show results of FACS analysis of binding of anti-TMPRSS6 monoclonal antibodies MWTx-001 (FIGS. 5A-5C), MWTx-002 (FIGS. 5D-5F), MWTx-003 (FIGS. 5G-5I) anti-TMPRSS6 antibodies and their humanized variants hzMWTx-001Var (FIGS. 5J-5L), hzMWTx-002Var (FIGS. 5M-5O), hzMWTx-003Var (FIGS. 5P-5R) anti-TMPRSS6 antibodies to HEK293T cells expressing homologous matriptases. HEK293T cells stably expressing human TMPRSS6 (matriptase-2) (FIGS. 5A, 5D, 5G, 5J, 5M, 5P) were used as a positive control, and HEK293T cells over-expressing matriptase (ST14) (FIGS. 5B, 5E, 5H, 5K, 5N, 5Q) and/or matriptase-3 (TMPRSS7) (FIGS. 5C, 5F, 5I, 5L, 5O, 5R) proteins were used to test binding to homologous matriptases. In each panel (FIGS. 5A-5R) HEK293T cells not expressing matriptase (HEK293T) were used as a negative control, with control (Ctrl) results clearly indicated.

FIGS. 6A-6L show anti-TMPRSS6 antibody treatment increases hepcidin expression in mouse in a dose-dependent manner. FIGS. 6A-6C show effects of MWTx-003 anti-TMPRSS6 antibody (FIGS. 6A-6B) or its humanized variant hzMWTx-003Var anti-TMPRSS6 antibody (FIG. 6C) on serum iron. FIG. 6D shows effect of GFP-TMPRSS6 on serum hepcidin. FIGS. 6D-6F show effects of MWTx-003 anti-TMPRSS6 antibody (FIGS. 6D-6E) or its humanized variant hzMWTx-003Var anti-TMPRSS6 antibody (FIG. 6F) on serum hepcidin. FIG. 6G shows effect of GFP-TMPRSS6 on liver hepcidin RNA. FIGS. 6G-6I show effects of MWTx-003 anti-TMPRSS6 antibody (FIGS. 6G-6H) or its humanized variant hzMWTx-003Var anti-TMPRSS6 antibody (FIG. 6I) on liver hepcidin RNA. FIGS. 6J-6L show serum concentrations of MWTx-003 anti-TMPRSS6 antibody (FIGS. 6J-6K) or its humanized variant hzMWTx-003Var anti-TMPRSS6 antibody (FIG. 6L). Mouse IgG2b (MoIG2b) (FIGS. 6A-6B, 6D-6E, 6G-6H, 6J-6K) or human IgG1 (HuIGg1)(FIGS. 6C, 6F, 6I, 6L) was used as an isotype control, PBS was used as a vehicle control, and GFP vector was used as a vector control (FIGS. 6A, 6D, 6G, 6J).

FIGS. 7A-7D show effects of MWTx-003 anti-TMPRSS6 antibody on RBC (FIG. 7A), HGB (FIG. 7B), HCT (FIG. 7C) and RDW (FIG. 7D) using Th3/+ mice. FIG. 7F shows effect of MWTx-003 anti-TMPRSS6 antibody on serum iron using Th3/+ mice. FIG. 7G shows effect of MWTx-003 anti-TMPRSS6 antibody on liver non-heme iron using Th3/+ mice. FIG. 7H shows effect of MWTx-003 anti-TMPRSS6 antibody on serum hepcidin using Th3/+ mice. FIG. 7I shows effect of MWTx-003 anti-TMPRSS6 antibody on liver hepcidin RNA using Th3/+ mice. FIG. 7J shows serum concentration of MWTx-003 anti-TMPRSS6 antibody using Th3/+ mice. FIGS. 7L-7M show effect of MWTx-003 anti-TMPRSS6 antibody on erythropoiesis using bone marrow from Th3/+ mice. FIGS. 7O-7P show effect of MWTx-003 anti-TMPRSS6 antibody on erythropoiesis using splenocytes from Th3/+ mice. Representative plots in FIGS. 7K-7P show with four distinct cell clusters (I: basophilic erythroblasts; II: polychromatic erythroblasts; III: orthochromatic erythroblasts and nonnucleated reticulocytes and IV: mature red cells) and their corresponding percentages of cell numbers are highlighted. Wildtype mice were used as a positive control (FIGS. 7A-7J, 7K, 7N), and mouse IgG2b (MoIgG2b) was used as isotype control in the treatment (FIGS. 7A-7J, 7L, 7O). Bar graphs in FIGS. 7Q-7R show average results for cell clusters I, II, III, and IV in bone marrow (FIG. 7Q) and spleen (FIG. 7R) for each treatment regime (WT, Th3/+ w/MoIgG2b, Th3/+ w/MWTx-003) after 4 weeks, where comparisons allow identification of shifts in each population, most notably a shift to mature red blood cells (cluster IV) after MWTx-003 treatment.

FIGS. 8A-8D show results of epitope binning of MWTx-001, MWTx-002 and MWTx-003 anti-TMPRSS6 antibodies for human ecto-TMPRSS6-FLAG using the Octet® RED96e. FIG. 8A shows epitope binning of MWTx-001 anti-TMPRSS6 antibody towards ecto-TMPRSS6-FLAG. FIG. 8B shows epitope binning of MWTx-002 anti-TMPRSS6 antibody towards ecto-TMPRSS6-FLAG. FIG. 8C shows epitope binning of MWTx-003 anti-TMPRSS6 antibody towards ecto-TMPRSS6-FLAG. FIG. 8D summarizes association signals for MWTx-001, MWTx-002 and MWTx-003 anti-TMPRSS6 antibodies.

DETAILED DESCRIPTION

Figure 2D:
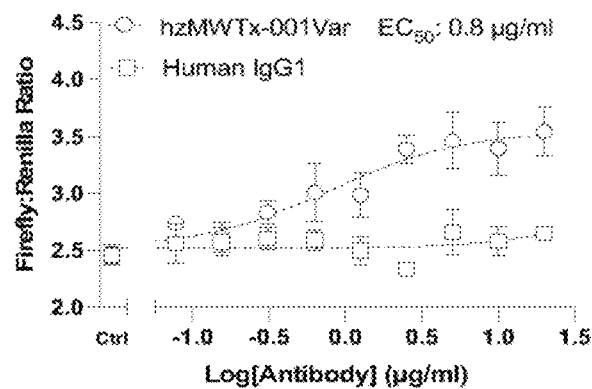

The invention relates to novel antibodies and antigen-binding fragments thereof that bind TMPRSS6, and methods of making and using the same.

Terminology/Definitions

Scientific and technical terms used in connection with the present invention shall have the meanings that are commonly understood by those of ordinary skill in the art, unless otherwise defined. Use of singular terms ("a" or "an" or "the" or other use of a term in the singular) include plural reference, and plural terms shall include the singular, unless the context clearly dictates otherwise. Thus, for example, reference to "an antibody" includes "one or more" antibodies or a "plurality" of such antibodies.

Generally, nomenclature and techniques of molecular biology, microbiology, cell and tissue culture, protein and nucleotide chemistry, and recombinant DNA techniques available to one of skill of the art can be employed for the antibodies, antigen-binding fragments, compositions, and methods disclosed herein. Techniques and procedures described herein are generally performed according to conventional methods well known in the art and as described in various general and more specific references, inter alia, Sambrook et al. (1989) MOLECULAR CLONING: A LABORATORY MANUAL (2nd ed., Cold Spring Harbor Laboratory Press, Cold Spring Harbor, N.Y.) and Ausubel et al. (1994) CURRENT PROTOCOLS IN MOLECULAR BIOLOGY, Volumes I-III (John Wiley & Sons, N.Y.). Enzymatic reactions and purification techniques are performed according to manufacturer's specifications or as commonly accomplished in the art or as described herein, unless otherwise specified herein. Techniques and methods for pharmaceutical preparation and formulation, and treatment of subjects, are described herein using conventional nomenclature.

"Antibody" refers in the broadest sense to a polypeptide or combination of polypeptides that recognizes and binds to an antigen through one or more immunoglobulin variable regions, where the immunoglobulin variable regions may be naturally occurring or non-naturally occurring, e.g., as a result of engineering, chimerization, humanization, optimization, CDR-grafting, or affinity maturation.

An "antibody" as disclosed herein can be a whole (intact, full length) antibody, a single chain antibody, or an antigen binding fragment with one or two chains, and can be naturally occurring and non-naturally occurring. An antibody comprises at least sufficient complementarity determining regions (CDR), interspersed with framework regions (FR), for the antibody to recognize and bind to an antigen. An anti-TMPRSS6 antibody disclosed herein may be, but is not limited to, at least one of a monoclonal antibody, a polyclonal antibody, a humanized antibody, a chimeric antibody, a single chain antibody, a Fab fragment, a single-chain variable fragment (scFv), an aptamer, a single-domain antibody (VHH or nanobody), a recombinant antibody, a modified antibody having peptide/other moieties attached to antibody and/or additional amino acids added the N- or C-terminus, or other TMPRSS6-binding fragment or variant. Whole antibody, full length antibody, intact antibody, naturally occurring antibody, or equivalent terms are understood to refer to a polypeptide, in particular a glycoprotein, comprising at least two heavy chains (HCs) and two light chains (LCs) interconnected by disulfide bonds. Each HC is comprised of a heavy chain variable region (VH) and an HC constant region (CH), and each light chain is comprised of a light chain variable region (VL) and an LC constant region (CL). The HC and LC variable regions, VH and VL, include a binding domain that interacts with an antigen. The VH and VL regions can be further subdivided into CDR regions characterized by hypervariability, interspersed with FR regions that are typically more conserved. Each VH and VL is typically composed of three CDRs and four FRs arranged from amino-terminus to carboxy-terminus in the following order: FR1, CDR1, FR2, CDR2, FR3, CDR3, FR4. The constant regions of the antibodies may mediate the binding of the immunoglobulin to host tissues or factors, including various cells of the immune system and the classical complement system. Typically, an antibody comprises at least heavy chain (HC) CDR1, CDR2, and CDR3 and light chain (LC) CDR1, CDR2, and CDR3 sequences, where any one of these sequences may be naturally or non-naturally occurring. An antibody may comprise fewer CDR sequences, as long as the antibody can recognize and bind an antigen.

An anti-TMPRSS6 antibody disclosed herein may be a variant comprising at least one altered CDR or framework sequence, wherein CDR and/or framework sequences may by optimized by mutating a nucleic acid molecule encoding such framework sequence. Variants may be constructed with HC and LC portions derived independently from different sources. Techniques for generating variants include but are not limited to conservative amino acid substitution, computer modeling, screening candidate polypeptides alone or in combinations, and codon optimization, and it is understood that a skilled person is capable of generating antibody variants as may be needed. An anti-TMPRSS6 antibody disclosed herein may be a fragment. Antigen binding functions of an antibody can be performed by fragments such as: a Fab fragment; a monovalent fragment consisting of the VL, VH, CL and CH1 domains; a F(ab)$_2$ fragment; a bivalent fragment comprising two Fab fragments linked by a disulfide bridge at the hinge region; an Fd fragment consisting of the VH and CH1 domains; a single-chain variable fragment (scFv) consisting of the VL and VH domains of a single arm of an antibody; a single domain antibody (dAb) fragment which consists of a VH domain; and an isolated CDR (VHH, nanobody), or an aptamer. Antigen binding portions can be incorporated into single domain antibodies, maxibodies, minibodies, nanobodies, intrabodies, diabodies, triabodies, tetrabodies, v-NAR and bis-scFv (see, e.g., Hollinger and Hudson, 2005, Nature Biotechnology, 23, 9, 1126-1136). Antigen binding portions of antibodies can be grafted into scaffolds based on polypeptides to form monobodies (see, e.g., U.S. Pat. No. 6,703,199, which describes fibronectin polypeptide monobodies).

The term antibody encompasses various broad classes of polypeptides that can be distinguished biochemically. The "class" of an antibody refers to the type of constant domain or constant region possessed by its heavy chain. Those skilled in the art understand that there are five major classes of antibodies, viz., IgA, IgD, IgE, IgG, and IgM, and several of these may be further divided into subclasses (isotypes), e.g., IgG1, IgG2, IgG3, IgG4, IgA1, and IgA2, each of which is well characterized and known to confer functional specialization. Modified versions of each of these classes and isotypes are readily discernable and within the scope of the instant disclosure. While all immunoglobulin classes are within the scope of the present disclosure, the present disclosure will be directed largely to the IgG class of immunoglobulin molecules.

The term "chimeric" antibody refers to an antibody in which a portion of the heavy chain (HC) and/or light chain (LC) involved in forming the immunoreactive site is derived from a particular source or species, while the remainder of the HC and/or LC is derived from a different source or species. In certain embodiments the target binding region or site will be from a non-human source (e.g., mouse or non-human primate) and the constant region is human.

As used herein, the phrase "humanized antibody" refers to an antibody or antibody variant derived from a non-human antibody, typically a mouse monoclonal antibody, where CDRs from the parental, non-human antibody are grafted (fused) in a framework comprising variable regions derived from a human immunoglobulin framework, in particular an acceptor human framework or a human consensus framework. Techniques and principles for designing, making, and testing humanized antibodies are known (Jones P T, Dear P H, Foote J, Neuberger M S, Winter G. Replacing the complementarity-determining regions in a human antibody with those from a mouse. *Nature.* 1986 May 29-Jun. 4; 321(6069):522-5; Almagro J C, Fransson J. Humanization of antibodies. *Front Biosci.* 2008 Jan. 1; 13:1619-33). It is understood that changes can be made to an acceptor framework at multiple locations in order to develop a humanized antibody having improved features according to the desired use, e.g., high affinity for target, low clearance, low toxicity, etc. An anti-TMPRSS6 antibody disclosed herein may be a humanized variant.

"Affinity" refers to the strength of the sum total of noncovalent interactions between a single binding site of a molecule (e.g., an antibody) and its binding partner (e.g., an antigen). Unless indicated otherwise, binding affinity as used herein refers to intrinsic binding affinity which reflects a 1:1 interaction between members of a binding pair (e.g., antibody and antigen). Affinity can be measured by common methods known in the art, including those described herein. The calculated concentration at which approximately 50% of maximal binding (the calculated EC50) can be used as an estimate of affinity. The affinity of a molecule X for its partner Y can generally be represented by the dissociation constant (Kd or KD, representing $k_{off}/k_{on}$ measured for the interaction).

A "subject" is a mammal, where mammals include but are not limited to primates (e.g., humans and non-human primates such as monkeys), domesticated animals (e.g., cows, sheep, cats, dogs, pigs, llamas, and horses), rabbits, and rodents (e.g., mice and rats). In certain embodiments, the subject is a human. The phrases "to a subject in need thereof" or "to a patient in need thereof" or "to a patient in need of treatment" or "a subject in need of treatment" may include subjects that would benefit from administration of the anti-TMPRSS6 antibodies disclosed herein, for treatment of an iron overload disorder. It is understood that administration of anti-TMPRSS6 antibodies encompasses administration to "a subject in need thereof" can be interpreted as referring to a subject known or suspected to have an iron overload disorder, in particular a β-thalassemia, based on indicators such as symptoms, family history, or genotype. It is further understood that anti-TMPRSS6 antibodies can be administered to a subject that is not known or suspected to have a disorder of iron metabolism, for purposes that may include but are not limited to, preventative or prophylactic purposes, for screening, for diagnostics, for research purposes, or to achieve results distinct from treating a disorder.

An "effective amount" of an anti-TMPRSS6 antibody, e.g., in a pharmaceutical formulation, refers to an amount effective, at dosages and for periods of time necessary, to achieve the desired therapeutic or prophylactic result. It is understood that "effective amount" is intended to refer to the amount of an anti-TMPRSS6 antibody or a pharmaceutical composition comprising an anti-TMPRSS6 antibody that will elicit the biological response of, or desired therapeutic effect on, a cell, a tissue, a system, a non-human animal subject, a non-human mammal subject, or a human subject that is being measured. The terms "therapeutically effective amount", "pharmacologically effective amount", and "physiologically effective amount" are used interchangeably to refer to the amount of an anti-TMPRSS6 antibody that is needed to provide a threshold level of active agents in the bloodstream or in the target tissue. The precise amount will depend upon numerous factors, e.g., the particular anti-TMPRSS6 antibody (active agent), the components and physical characteristics of the composition, intended population of subjects/patients to be treated, considerations such as the disease state, age, sex, and weight of a subject, and the like, and can readily be determined by one skilled in the art, based upon the information provided herein or otherwise available in the relevant literature. The terms, "improve", "increase" or "reduce", as used in this context, indicate values or parameters relative to a baseline measurement, such as a measurement in the same subject prior to initiation of the treatment described herein, or a measurement in a control individual (or multiple control individuals) in the absence of the treatment described herein.

The term "pharmaceutical composition" or "pharmaceutical formulation" refers to a preparation which is in such form as to permit the biological activity of an active ingredient contained therein to be effective, in particular an anti-TMPRSS6 antibody. It is understood that a pharmaceutical composition may contain more than one active ingredient, e.g., more than one anti-TMPRSS6 antibody, or a combination of an anti-TMPRSS6 antibody with another active ingredient that acts on a different target, where such combinations can be but are not limited to, a combination of an antiTMPRSS6 antibody with another active ingredient having a desired effect on hematopoietic processes, in particular erythropoiesis, a combination of an anti-TMPRSS6 antibody with gene therapy agents such as agents to carry out gene therapy targeting the HBB gene, or a combination of an anti-TMPRSS6 antibody with Fc-fusion proteins that target TGF superfamily ligands to stimulate erythropoiesis. A "pharmaceutically acceptable carrier" refers to an ingredient in a pharmaceutical formulation, other than an active ingredient, which is nontoxic to a subject. It is understood that a pharmaceutically acceptable carrier can be, but is not limited to, a buffer, excipient, stabilizer, an adjuvant, or preservative.

The term "treat" or "treating" or similar terms as used herein, can refer to an outcome that is deemed beneficial for a particular subject in a defined set of circumstances. Treating a disorder of iron metabolism may refer non-exclusively to any of reducing, ameliorating, slowing, interrupting, arresting, alleviating, stopping, or reversing the progression or severity of an existing symptom, disorder, condition, or disease, and may further encompass prevention or delay of the onset of one or more symptoms of an iron overload disorder, and/or lessening of the severity or frequency of one or more symptoms of an iron overload disorder. The terms "treating" or "method of treating" or equivalents can encompass one or more uses of anti-TMPRSS6 antibodies disclosed herein, including but not limited to therapeutic, prophylactic, preventive, diagnostic, imaging, and screening uses.

The term "vector," as used herein, refers to a nucleic acid molecule capable of propagating a nucleic acid to which the vector sequence is linked, in a host cell in which the vector is introduced. Vectors capable of directing the expression of nucleic acids to which they are operatively linked are referred to herein as "expression vectors."

Anti-TMPRSS6 Antibodies

Antibodies and antigen-binding fragments are provided that are capable of binding TMPRSS6 on the surface of a cell and modulating the activity of at least one component involved in iron metabolism, in particular at least one component involved in iron overload disorders associated with abnormal suppression of hepcidin expression. Anti-TMPRSS6 antibodies that are capable of binding TMPRSS6 on the surface of a cell and modulating the activity of at least one component involved in regulating hepcidin expression can be used in methods for treating iron overload disorders associated with abnormal suppression of hepcidin expression. Anti-TMPRSS6 antibodies that are capable of binding TMPRSS6 on the surface of a cell and modulating TMPRSS6 suppression of hepcidin expression can be used to therapeutically target TMPRSS6 in methods for treating iron overload disorders associated with abnormal suppression of hepcidin expression.

Once antibodies or fragments specific for TMPRSS6, in particular human TMPRSS6 expressed on the surface of a cell, have been obtained, the desired biological activity of modulating the activity of at least one component involved in iron metabolism thereof can be tested by several methods known to the skilled person.

It is understood that "modulate" or "modulating" or similar terms as used herein can refer to one or more effects that can result when an anti-TMPRSS6 antibody disclosed herein binds its target. "Modulating" and its equivalents can refer to different modes of action and effects depending on the component under consideration, i.e., modulating can refer to neutralizing, reversing, inhibiting, blocking, reducing, antagonizing, or otherwise interfering with the activity of certain components involved in iron metabolism, while for other components involved in iron metabolism the term modulating can refer to increasing, enhancing, or having an agonist effect on these components.

It is understood that the term "component" can refer not only to target molecule TMPRSS6, but also to a downstream process or pathway involved in iron metabolism. Thus, a component within the meaning of a process or pathway can be, but is not limited to, regulation of hepcidin expression, TMPRSS6 suppression of hepcidin expression, the process of hepcidin expression, regulation of hepcidin levels, increasing hepcidin levels, the activity of the hepcidin promoter, or TMPRSS6 suppression of the BMP/SMAD pathway-induced expression of hepcidin, regulation of liver non-heme iron levels, one or more processes involved in splenomegaly, or one or more hematopoietic processes involved in regulation of red blood count (RBC), hematocrit (HCT), red cell distribution width (RDW), and erythropoiesis, in particular production of mature red cells.

Anti-TMPRSS6 antibodies as disclosed herein can be used to therapeutically target at least one component involved in iron metabolism, in particular at least one component involved in iron overload disorders. In certain embodiments, anti-TMPRSS6 antibodies as disclosed herein can be used to therapeutically target at least one component involved in regulating hepcidin expression, and modulate the activity of the component to achieve increased hepcidin expression. In certain embodiments, anti-TMPRSS6 antibodies as disclosed herein can be used to modulate the activity of the hepcidin promoter to achieve increased hepcidin expression. It is understood that anti-TMPRSS6 antibodies as disclosed herein can be used to therapeutically target TMPRSS6 and thereby modulate the downstream activity of other components of hepcidin expression, including but not limited to, regulation of liver non-heme iron levels, one or more processes involved in splenomegaly, or one or more hematopoietic processes involved in regulation of red blood count (RBC), hematocrit (HCT), red cell distribution width (RDW), and erythropoiesis, in particular production of mature red cells.

Using anti-TMPRSS6 antibodies as disclosed herein to therapeutically target at least one component involved in iron metabolism, allows precise modulation of the targeted component. It is understood that by using anti-TMPRSS6 antibodies as disclosed herein to precisely target TMPRSS6 and its downstream effects on at least one component involved in regulating hepcidin expression, it is possible to avoid undesirable effects, difficulties with delivery and/or effectiveness, and regulatory hurdles associated with other approaches to treating iron overload disorders that are currently in use or under development, e.g., blood transfusions that can further exacerbate iron overload, iron chelation with poor patient compliance, intrusive phlebotomy or splenectomy that only manage symptoms, gene therapy targeting the HBB gene with potential permanent pleiotropic effects in multiple systems, gene therapy and gene editing with unknown off-target effects, Fc-fusion proteins targeting TGF superfamily ligands to inhibit SMAD signaling that do not reduce the need for iron chelation therapy to manage iron overload, and other approaches that are difficult to control or deliver such as hepcidin mimetics, and antisense or iRNA drugs targeting TMPRSS6. It is understood that using anti-TMPRSS6 antibodies for precise therapeutic targeting does not exclude the possibility of using anti-TMPRSS6 antibodies in methods and compositions for combination treatments, e.g., in combination with another active ingredient that acts on a different target, in combination with an antibody that binds a different target, in combination with gene therapy agents and methods for targeting the HBB gene, or in combination with Fc-fusion proteins that target TGF superfamily ligands to stimulate erythropoiesis.

Anti-TMPRSS6 antibodies disclosed herein allow the development of treatments that can be tailored to each subject (e.g., dosage, frequency of administration), where they can be continued and discontinued with ease, and combined with other therapies. In certain strategic embodiments, anti-TMPRSS6 antibodies disclosed herein can be combined with other therapies that may address multiple therapeutic targets and/or address deficits or undesirable effects of one of the therapies in the combination therapy.

Exemplary Embodiments of Anti-TMPRSS6 Antibodies and Uses Thereof

Non-limiting exemplary embodiments of anti-TMPRSS6 antibodies of the invention are presently disclosed, in particular in the Examples, Tables, and Figures.

Antibodies Capable of Binding TMPRSS6

As demonstrated in the Examples, a functional cascade can be used to identify and characterize anti-TMPRSS6 antibodies of the present invention, where a first step in the cascade involves screening for antibodies capable of binding to human TMPRSS6 on the surface of a cell expressing TMPRSS6 (Example 1, FIG. 1), followed by a second step to identify antibodies capable of binding to human TMPRSS6 on the surface of a cell expressing TMPRSS6 and modulating the activity of a component involved in iron metabolism, in this case testing for the ability to increase hepcidin (HAMP) promoter activity (Example 2). As demonstrated by exemplary embodiments shown in FIG. 1, the first step identified 143 antibodies (clones) capable of binding to human TMPRSS6 on the surface of a cell expressing TMPRSS6, and the second step identified ten (10) of the antibodies (out of 143 screened) as "active" antibodies (clones) that were able to increase hepcidin (HAMP) promoter activity.

In a third step of the functional cascade (FIG. 1), the ten (10) "active" antibodies were tested for cross-reactivity with non-human TMPRSS6 targets from sources that would be relevant for further studies, viz., testing for cross-reactivity with mouse TMPRSS6 relevant to preclinical efficacy studies in a mouse model, and testing for cross-reactivity with cynomolgus monkey TMPRSS6 relevant to toxicity (safety) trials. As demonstrated by exemplary embodiments shown in FIG. 1, demonstrated in Example 4 and illustrated in FIG. 4, three (3) clones (out of 10 screened) showed cross-reactivity with at least one non-human TMPRSS6 and were designated MWTx-001, MWTx-002, and MWTx-003. Each of the monoclonal antibodies was sequenced and CDRs on each HC and LC were identified (Kabat numbering). HC and LC sequences were identified as follows for: MWTx-001 (SEQ ID NOs: 61(HC) and 63(LC)); MWTx-002 (SEQ ID NOs: 65 (HC) and 67 (LC)); and MWTx-003 9SEQ ID NOs: 69(HC) and 71 (LC)). A hybridoma cell line producing the MWTx-001 monoclonal antibody has been deposited under ATCC Accession No. PTA-126759. A hybridoma cell line producing the MWTx-002 monoclonal antibody has been deposited under ATCC Accession No. PTA-126760. A hybridoma cell line producing the MWTx-003 monoclonal antibody has been deposited under ATCC Accession No. PTA-126761.

Humanized Variants

Humanized antibodies comprising CDRs derived from a non-human source grafted into a human-derived antibody framework are expected to be non-immunogenic when administered to a human subject. As demonstrated by exemplary embodiments disclosed in Example 2, humanized anti-TMPRSS6 antibody variants were successfully generated, tested, optimized, and selected. Multiple candidate HC and LC variants were developed wherein each HC or LC variant had the same CDR sequences but the variable region frameworks sequences could vary at over 90% of the framework positions, and these variants tested in different HC/LC combinations to identify combinations having desired features. After initial design and testing, variants that showed desired antigen binding affinity were selected for further evaluation and development, including but not limited to modification of some parental CDR sequences to avoid potential unwanted events such as aspartate isomerization, and modification of some constant regions (Fc) to achieve desired functions such as minimizing antibody-dependent cellular cytotoxicity (ADCC), to arrive at humanized variants hzMWTx-001Var (SEQ ID NOs: 73 (HC) and 75 (LC)), hzMWTx-002Var (SEQ ID NOs: 77(HC) and 79 (LC)), and hzMWTx-003Var (SEQ ID NOs: 81(HC) and 83(LC)).

Anti-TMPRSS6 Antibodies that Increase Hepcidin Promoter Activity

As disclosed herein, antibodies for use in treating iron overload disorders characterized by reduced hepcidin expression may modulate the activity of at least one component involved in hepcidin expression, where the component may be activity of the hepcidin promoter. As demonstrated by exemplary embodiments using an in vitro assay disclosed in Example 2, anti-TMPRSS6 antibodies MWTx-001, MWTx-002, MWTx-003, hzMWTx-001Var, hzMWTx-002Var, and hzMWTx-003Var increased HAMP promoter activity in a dose-dependent manner (FIGS. 2A-2F), while isotype controls at the same concentrations did not increase HAMP promoter activity.

Anti-TMPRSS6 Antibodies Having High Affinity for a Target in a Relevant Biological Context Anti-TMPRSS6 antibodies showed high affinity for a biologically appropriate target, i.e., human TMPRSS6 expressed on the surface of a cell. As demonstrated by exemplary embodiments of affinity measurements using three different methods disclosed in Example 3 and FIG. 3M, monoclonal antibodies MWTx-001, MWTx-002, and MWTx-003, and humanized variants hzMWTx-001Var, hzMWTx-002Var, and hzMWTx-003Var consistently exhibited favorable affinity characteristics for therapeutically effective antibodies or antibody fragments.

Anti-TMPRSS6 Antibodies Having Cross-Reactivity with Non-Human Targets

It is desirable for therapeutically useful antibodies or antibody fragments to have sufficient cross-reactivity with non-human targets (non-human homologues) from sources that would be relevant for further studies such as preclinical efficacy studies, animal models of disease, toxicology studies, etc., such that the antibodies or antibody fragments should recognize, e.g., a mouse homologue and/or a primate homologue such as from cynomolgus monkey. As demonstrated by exemplary embodiments disclosed in Example 4, MWTx-001, hzMWTx-001Var, MWTx-003, and hzMWTx-003Var showed detectable cross-reactivity with mouse TMPRSS6, while MWTx-001, MWTx-002, MWTx-003, hzMWTx-001Var, hzMWTx-002Var, and hzMWTx-003Var showed detectable cross-reactivity with cynomolgus monkey TMPRSS6.

Anti-TMPRSS6 Antibodies Specifically Bind TMPRSS6 (Matriptase-2)

Antibodies with a high level of specific binding to a target protein and low cross-reactivity with homologous proteins in the same organism, are expected to have reduced or no off-target effects. Anti-TMPRSS6 antibodies provided here show high specificity for human TMPRSS6 (matriptase-2), making them suitable for use in targeted compositions and methods. As demonstrated by exemplary embodiments disclosed in Example 5 and illustrated in FIGS. 5A-R, monoclonal antibodies MWTx-001, MWTx-002, and MWTx-003, and their humanized variants hzMWTx-001Var, hzMWTx-002Var, and hzMWTx-003Var show specific binding to human TMPRSS6 (matriptase-2) and did not show detectable cross-reactivity with homologous human matriptases, i.e., these antibodies did not show detectable binding to matriptase-1 (ST14) or matriptase-3 (TMPRSS7).

Anti-TMPRSS6 Antibodies Having In Vivo Dose-Dependent Effects on Hormones and Symptoms Associated with Iron Overload Disorder Antibodies that can increase the level of serum hepcidin, a hormone that controls iron absorption and mobilization from iron stores, are expected to reduce, ameliorate, or prevent symptoms of iron overload disorder, in particular to reduce, ameliorate, or prevent symptoms of elevated levels of serum iron. As demonstrated by exemplary embodiments shown in Example 6, administration of anti-TMPRSS6 monoclonal antibody MWTx-003 or humanized variant hzMWTx-003Var to wildtype subjects, i.e., subject that is not known or suspected to have an iron overload, resulted in an increase in serum hepcidin levels (FIGS. 6A-6C), a decrease in serum iron levels (FIGS. 6D to 6F), and an increase in liver hepcidin RNA levels (FIGS. 6G-6I) compared with isotype controls. These effects were dose-dependent, which can be interpreted as indicating, without wishing to be bound by a mechanism of action, that the dose-dependent in vivo effects of anti-TMPRSS6 antibodies indicate that a skilled person can determine an effective amount (dosage) for a given subject.

Anti-TMPRSS6 Antibodies Having In Vivo Efficacy in a β-Thalassemia Disease Model Antibodies and antibody fragments that can relieve one or more symptoms of an iron overload disorder in vivo when administered to a subject exhibiting an animal model of the disease, i.e., a subject that is known or suspected to have an iron overload disorder, are expected to have therapeutic effectiveness for clinical use. As demonstrated by exemplary embodiments shown in Example 7 using the Th3/+ mouse model of β-thalassemia, administration of the anti-TMPRSS6 monoclonal antibody MWTx-003 resulted in multiple effects including but not limited to reducing liver non-heme iron, increasing serum hepcidin, increasing liver hepcidin RNA, reducing splenomegaly, increasing red blood count (RBC), increasing hematocrit (HCT), reducing red cell distribution width (RDW), and increased production of mature red cells (increased erythropoiesis), compared with isotype controls. Each of these effects can be understood as an amelioration of a symptom of the disorder. Symptoms of the disorder are manifested in multiple biological systems that include but are not limited to effects in the liver (effects on liver non-heme iron, liver hepcidin RNA), in the blood (effects on serum iron levels, circulating hormone levels in particular serum hepcidin levels, RBC, HCT, RDW), spleen size and function (splenomegaly), and erythropoiesis in multiple sites including but not limited to bone marrow and spleen (effects on abundance of different precursor cell types and abundance of mature red cells in erythropoietic sites). Administration of anti-TMPRSS6 antibodies ameliorated multiple symptoms throughout the disease model subject, shifting the measured symptom levels away from levels seen in isotype controls for the disease model (untreated disease) and towards the levels seen in wildtype littermates that represent normal levels in a genetically similar subject that is not known or suspected to have the disease. Without wishing to be bound by a theory or mechanism of action, it is understood that ineffective erythropoiesis is a driving force for abnormal hepcidin suppression leading to increased iron absorption and iron overload, such that a treatment that improves erythroblast differentiation and maturation into red cells should be therapeutically beneficial for treating an iron overload disorder. The present non-limiting exemplary embodiment discloses an anti-TMPRSS6 antibody therapy that increased erythroblast differentiation and maturation into red cells and also decreased iron loading.

Compositions

Compositions are provided that comprise the anti-TMPRSS6 antibody of the present invention with safe and effective amounts and pharmaceutically acceptable carrier (s) or excipient (s) suitable for the intended use(s) of each composition. Such carriers include but are not limited to: saline, buffer, glucose, water, glycerol, ethanol, excipient, stabilizer, preservative, or combinations thereof. It is understood that the pharmaceutical preparation should match the administration mode.

Anti-TMPRSS6 antibodies disclosed herein can be administered by any suitable means, including but not limited to injection or parenteral infusion. Parenteral infusion can include intramuscular, intravenous, intraarterial, intraperitoneal, subcutaneous administration, or parenteral delivery to the liver. Anti-TMPRSS6 antibodies disclosed herein can be formulated for introduction into hepatic tissue or vasculature for delivery localized to target tissues. Anti-TMPRSS6 antibodies disclosed herein can be administered using a device, or as a depot, or in a sustained-release preparations (e.g., semipermeable matrices of solid hydrophobic polymers containing the antibody, or microcapsules) to allow slow and/or measured and/or localized delivery. Anti-TMPRSS6 antibodies disclosed herein can be formulated and administered using colloidal drug delivery systems (for example, liposomes, albumin microspheres, microemulsions, nano-particles and nanocapsules) or in macroemulsions.

Methods

Methods are provided for treating a disorder of iron metabolism using an effective amount of an anti-TMPRSS6 antibody disclosed herein. Without wishing to be bound by a particular mechanism of action, methods provided for targeting TMPRSS6 using anti-TMPRSS6 antibodies disclosed herein result in multiple downstream effects, in particular effects on components (molecules, systems, processes) involved in iron metabolism and erythropoiesis. Without wishing to be bound by a particular mechanism of action, methods are provided for treating a disorder of iron metabolism using an effective amount of an anti-TMPRSS6 antibody disclosed herein to modulate the activity of a component involved in iron metabolism. In particular, methods are provided for treating iron overload disorders associated with excess iron accumulation in tissues and organs, including disorders related to or characterized by ineffective erythropoiesis that may include but are not limited to β-thalassemia, in particular non-transfusion dependent thalassemia, MDS (myelodysplastic syndrome), dyserythropoietic anemia, and sideroblastic anemia. Without being limited to a single mechanism of action, methods are provided for treating an iron overload disorders associated with low hepcidin levels, in particular disorders associated with suppressed hepcidin expression, including a disease or state in which abnormal suppression of hepcidin expression is involved, by administering anti-TMPRSS6 antibodies capable of increasing hepcidin expression.

Methods for treating a disorder of iron metabolism as provided herein comprise administering an effective amount of an anti-TMPRSS6 antibody disclosed herein to a subject in need thereof, wherein administration of the effective amount of anti-TMPRSS6 antibody ameliorates at least one biological effect (symptom) associated with the disorder. Methods for treating a disorder of iron metabolism associated with suppressed hepcidin levels are provided wherein administration of an effective amount of an anti-TMPRSS6 antibody disclosed herein to a subject in need thereof, results in at least one of increased hepcidin promoter activity, increased hepcidin transcription, increased hepcidin RNA levels, and increased hepcidin levels, in particular serum hepcidin levels. Methods for treating a subject known or suspected to have an iron overload disorder are provided wherein administration of an effective amount of anti-TMPRSS6 antibody results in one or more biological effects including but not limited to reducing liver non-heme iron, increasing serum hepcidin, increasing liver hepcidin RNA, reducing splenomegaly, increasing red blood count (RBC), increasing hematocrit (HCT), reducing red cell distribution width (RDW), and increased production of mature red cells (increased erythropoiesis). Methods for treating a subject known or suspected to have an iron overload disorder characterized by ineffective erythropoiesis are provided wherein administration of an effective amount of anti-TMPRSS6 antibody results in one or more biological effects including but not limited to reducing liver non-heme iron, increasing serum hepcidin, increasing liver hepcidin RNA, reducing splenomegaly, increasing red blood count (RBC), increasing hematocrit (HCT), reducing red cell distribution width (RDW), and increased production of mature red cells (increased erythropoiesis).

Methods and compositions are provided for treating a disorder of iron metabolism, in particular an iron overload disorder, even more particularly an iron overload disorder characterized by ineffective erythropoiesis, wherein administration of an effective amount of an anti-TMPRSS6 antibody results in treating or ameliorating more than one biological effect or symptom associated with the disorder. Without wishing to be bound by a theory or mechanism of action, it is understood that ineffective erythropoiesis characterized by erythroid precursor apoptosis resulting in few mature red cells produced in the bone marrow, is a driving force for abnormal hepcidin suppression leading to increased iron absorption and iron overload. In accordance with this understanding, a treatment that improves erythroblast differentiation and maturation into red cells should be therapeutically beneficial for treating an iron overload disorder. The effectiveness of anti-TMPRSS6 antibody therapy to increase erythroblast differentiation and maturation into red cells, decrease iron loading, increase hepcidin expression, etc., maximizes the therapeutic benefit of the methods and compositions using anti-TMPRSS6 antibodies disclosed herein.

The following examples are offered to illustrate, but not to limit, the claimed invention.

EXAMPLES

Example 1: Antibody Production and Identification of Antibodies that Bind TMPRSS6

The production of novel monoclonal antibodies against TMPRSS6 was carried out under contract by the LakePharma Discovery Immunology group (LakePharma, Inc. San Carlos, CA), utilizing in vivo rodent immunization and hybridoma technology. DNA-based immunization via hydrodynamic gene transfer tail vein injection was performed in B6; SJL mice (The Jackson Laboratories) using a mixture of pLEV113_huTMPRSS6 and pLEV113_moTMPRSS6-TCE plasmid DNA (cloned at LakePharma, Inc). Sufficient plasma titers as determined by fluorescence-activated cell sorting (FACS) were obtained, triggering downstream antibody recovery and screening activities. Electrofusion using a NEPA GENE ECFG21 Super Electro Cell Fusion Generator (Nepa Gene Co., Ltd., Ichikawa-City, Chiba, Japan) was performed with pooled splenocytes from 2 immunized mice and a myeloma fusion partner. Fusion material was plated in a total of ten (10) 384-well plates in hypoxanthine-aminopterin-thymidine medium, which specifically selects for hybridomas over unfused myeloma partner cells. Hybridoma supernatants were initially screened for HuTMPRSS6 reactivity by FACS measurement to detect supernatants that gave a positive staining signal on TMPRSS6-expressing HEK293T cells (a plasmid encoding huTMPRSS6-(His)$_6$ (SEQ ID NO: 97) was transfected in HEK293T cells, TMPRSS6-expressing HEK293T cells were selected) and negative staining on parentals (HEK293T) on day 10 post-fusion. Hybridoma supernatants giving a positive staining signal on TMPRSS6-expressing HEK293 cells and negative staining on parentals were designated as "hits" for further screening. 192 hits were identified in the primary FACS screen and 143 hits were confirmed in secondary and tertiary FACS screens.

Example 2. Functional Screening of Anti-TMPRSS6 Antibodies; Identification, Generation, and Sequencing of Monoclonal Anti-TMPRSS6 Antibodies and Humanized Variants HAMP-Luciferase Reporter Assay A hepcidin promoter-luciferase reporter assay was used to measure responses of the HAMP promoter to various anti-TMPRSS6 antibodies (Du, X. et al., 2008. *Science* 320: 1088-1092; modified to use human HAMP promoter instead of mouse Hamp promoter as originally disclosed). For the HAMP-luciferase report assay, a 2.5 kb HAMP promoter fragment (Reference Genome GRCh38) was spliced upstream from a sequence encoding firefly luciferase. A control construct encoding *Renilla* luciferase, driven by a thymidine kinase promoter (Promega, E6931) was used as an internal control. These constructs were co-transfected into HepG2 cells (ATCC, HB-8065), together with constructs encoding TMPRSS6. Transfected HepG2 cells expressing TMPRSS6 were pre-treated with various concentrations of purified mAb diluted in starvation medium containing minimum essential medium (MEM, ATCC)+1% heat inactivated fetal bovine serum (FBS, Gibco)+1 mM sodium pyruvate+non-essential amino acids solution (Gibco)+10 mM HEPES (Gibco)+1% Pen/Strep (Gibco) for about 3 hrs before treatment with recombinant hBMP6 (R&D Systems) at a final concentration of 25-60 ng/ml to trigger BMP-SMAD-mediated signaling. Purified mouse IgG (Sigma-Aldrich) or human IgG1 (BioXcell) was used as a control. Upon an overnight treatment of hBMP6, cells were lysed and luciferase substrate were added. Luminescence readings from firefly luciferase and *Renilla* luciferase were each recorded by measuring total luminescence. Activity was calculated as the ratio of firefly luciferase luminescence to *Renilla* luciferase luminescence (control). Results for these assays are shown in FIGS. 2A-2F.

Functional Screening In Vitro

To screen for functionally active hybridomas, the HAMP-luciferase reporter assay described above was used to test all 143 HuTMPRSS6 binding hybridomas ("hits"). Supernatants of ten (10) out of 143 HuTMPRSS6 binding hybridomas increased HAMP promoter activity (data not shown), and were identified as "active clones" to undergo further testing. These ten (10) active clones were tested for cross reactivity against murine target MoTMPRSS6 as described in Example 4 below, and three (3) showed binding towards both HuTMPRSS6 and MoTMPRSS6 as measured by FACS. These three cross-reactive clones were further plated at a density of 1 cell/well in 192 wells of 384-well plates to generate monoclonal hybridoma clones, the resulting subclones that exhibited desired functional activity and cross-reactivity against non-human targets, e.g. murine TMPRSS6 (moTMPRSS6) and/or cynomolgus monkey TMPRSS6 (cynoTMPRSS6) were identified as MWTx-001, MWTx-002, and MWTx-003.

Sequences of Anti-TMPRSS6 Antibodies MWTx-001, MWTx-002, and MWTx-003

Sequences of MWTx-001, MWTx-002, and MWTx-003 were determined by isolating mRNAs from each hybridoma sample, carrying out reverse transcription polymerase chain reaction (RT-PCR) with unique mouse IgG-specific primer sets to amplify the target variable regions for sequencing. A unique heavy chain and a unique light chain were identified for each anti-TMPRSS6 antibody. The nucleotide sequence of each heavy chain and each light chain was determined. Amino acid sequences encoded by the nucleotide sequences were determined, CDR regions were identified using the Kabat numbering system. Table 1 presents heavy chain and light chain variable region amino acid sequences, and amino acid sequences of identified CDRs (based on Kabat numbering) and heavy chain and light chain variable region nucleotide sequences for each of MWTx-001, MWTx-002, and MWTx-003.

TABLE 1

Sequences of variable regions of anti-TMPRSS6 monoclonal antibodies MWTx-001, MWTx-002, and MWTx-003

MWTx-001
Heavy chain of MWTx-001:
Protein sequence of the variable region:
QVQLQQPGAELAKPGASVKMSCKASGYTFTSYWITWVKQRPGQDLEWIGNIYPGSGST
YYNEKFKSKATLTVDTSSRTAYMQLSSLTSADSAVYYCAPYDSDYAMDYWGQGTSVT
VSS (SEQ ID NO: 1)

| HC CDR-1 | HC CDR-2 | HC CDR-3 |
| --- | --- | --- |
| GYTFTSYW (SEQ ID NO: 2) | IYPGSGST (SEQ ID NO: 3) | APYDSDYAMDY (SEQ ID NO: 4) |

Nucleotide sequence of the variable region:
CAGGTCCAACTGCAGCAGCCTGGGGCTGAGCTTGCGAAGCCTGGGGCTTCAGTGAA
GATGTCCTGCAAGGCTTCTGGCTACACCTTCACCAGCTACTGGATAACCTGGGTGA
AGCAGAGGCCTGGACAAGACCTTGAGTGGATTGGAAATATTTATCCTGGTAGTGGT
AGTACTTACTACAATGAGAAGTTCAAGAGCAAGGCCACACTGACTGTAGACACATC
CTCCAGAACAGCCTACATGCAGCTCAGCAGTCTGACATCTGCGGACTCTGCGGTCT
ATTACTGTGCCCCCTATGATTCCGACTATGCTATGGACTACTGGGGTCAAGGAACCT
CAGTCACCGTCTCCTCA (SEQ ID NO: 5)

Light chain of MWTx-001:
Protein sequence of the variable region:
DIKMTQSPSSMYASLGERVTITCKASQDINNYLSWFQQKPGKSPKTLIYRANRLVDGVP
SRVSGSGSGQDYSLTISSLEYEDVGIYFCLQYDEFPLTFGAGTKLELK (SEQ ID NO: 6)

| LC CDR-1 | LC CDR-2 | LC CDR-3 |
| --- | --- | --- |
| QDINNY (SEQ ID NO: 7) | RAN (SEQ ID NO: 8) | LQYDEFPLT (SEQ ID NO: 9) |

Nucleotide sequence of the variable region
GACATCAAGATGACCCAGTCTCCATCTTCCATGTATGCATCTCTAGGAGAGAGAGT
CACTATCACTTGCAAGGCGAGTCAGGACATTAATAACTATTTAAGCTGGTTCCAGC
AGAAACCAGGGAAATCTCCTAAGACCCTGATCTATCGTGCAAACAGATTGGTAGAT
GGGGTCCCATCAAGGGTCAGTGGCAGTGGATCTGGGCAAGATTATTCTCTCACCAT
CAGCAGCCTGGAGTATGAAGATGTGGGAATTTATTTTTGTCTACAGTATGATGAGTT
TCCTCTCACGTTCGGTGCTGGGACCAAGCTGGAGCTGAAA (SEQ ID NO: 10)

MWTx-002
Heavy chain of MWTx-002:
Protein sequence of the variable region:
EVQLQQSGAELVKPGASVKLSCTASGFNIKDYYIHWVKERTEQGLEWFGRIDPEDGES
EYAPKFQGKATLTADTSSNTAYLQLSSLTSEDTAVYYCTRGDSMMVTYFDYWGQGTT
LTVSSE (SEQ ID NO: 11)

| HC CDR-1 | HC CDR-2 | HC CDR-3 |
| --- | --- | --- |
| GFNIKDYY (SEQ ID NO: 12) | IDPEDGES (SEQ ID NO: 13) | TRGDSMMVTYFDY (SEQ ID NO: 14) |

Nucleotide sequence of the variable region:
GAGGTTCAGCTGCAGCAGTCTGGGGCAGAACTTGTGAAGCCAGGGGCCTCAGTCAA
GTTGTCCTGCACAGCCTCTGGCTTCAACATTAAAGACTACTATATACACTGGGTGAA
AGAGAGGACTGAACAGGGCCTGGAGTGGTTTGGAAGGATTGATCCTGAGGATGGT
GAAAGTGAATATGCCCCGAAATTCCAGGGCAAGGCCACTTTAACAGCAGACACATC
CTCCAATACAGCCTACCTGCAGCTCAGCAGCCTGACATCTGAGGACACTGCCGTCT
ATTACTGTACTAGAGGAGACTCTATGATGGTTACCTACTTTGACTACTGGGGCCAA
GGCACCACTCTCACGGTCTCCTCA (SEQ ID NO: 15)

Light chain of MWTx-002:
Protein sequence of the variable region:
DIVMTQSHKFMSTSVGDRVSITCKASQDVSTAVAWYQQKPGQSPKLLIYWAFTRHTGV
PDRFTSTGSGTDYALTISSVQAEDLALYYCQQHYRSPWTFGGGTKLEIK (SEQ ID NO: 16)

TABLE 1-continued

Sequences of variable regions of anti-TMPRSS6 monoclonal
antibodies MWTx-001, MWTx-002, and MWTx-003

| LCCDR-1 | LC CDR-2 | LC CDR-3 |
|---|---|---|
| QDVSTA (SEQ ID NO: 17) | WAF (SEQ ID NO: 18) | QQHYRSPWT (SEQ ID NO: 19) |

Nucleotide sequence of the variable region:
GACATTGTGATGACCCAGTCTCACAAATTCATGTCCACATCAGTAGGAGACAGGGT
CAGCATCACCTGCAAGGCCAGTCAGGATGTGAGTACTGCTGTAGCCTGGTATCAAC
AAAAACCAGGGCAATCTCCTAAACTACTGATTTACTGGGCTTTCACCCGTCACACT
GGAGTCCCTGATCGCTTCACAAGCACTGGATCTGGGACAGATTATGCTCTCACCAT
CAGCAGTGTGCAGGCTGAAGACCTGGCACTTTATTACTGTCAGCAACATTATCGCA
GTCCGTGGACGTTCGGTGGAGGCACCAAACTGGAAATCAAA (SEQ ID NO: 20)

MWTx-003
Heavy chain of MWTx-003:
Protein sequence of the variable region:
EVQLQQSGAELVKPGASVKLSCTASGFNIEDYYIHWVKERTEQGLEWIGRIDPEDGETT
YAPQFQGKATIIPDTSSNTAYMQLSSLTSEDAAVYYCARSIYLDPMDYWGQGTSVTVSS
(SEQ ID NO: 21)

| HC CDR-1 | HC CDR-2 | HC CDR-3 |
|---|---|---|
| GFNIEDYY (SEQ ID NO: 22) | IDPEDGET (SEQ ID NO: 23) | ARSIYLDPMDY (SEQ ID NO: 24) |

Nucleotide sequence of the variable region:
GAAGTTCAGCTGCAGCAGTCTGGGGCAGAACTTGTGAAGCCAGGGGCCTCAGTCAA
GTTGTCCTGCACAGCTTCTGGCTTCAACATTGAAGACTACTATATACACTGGGTGAA
GGAGAGGACTGAACAGGGCCTGGAGTGGATTGGAAGGATTGATCCTGAGGATGGT
GAAACTACATATGCCCCGCAGTTCCAGGGCAAGGCCACTATAATACCAGACACATO
CTCCAACACAGCCTACATGCAGCTCAGCAGCCTGACATCTGAGGACGCTGCCGTCT
ATTACTGTGCTAGATCGATCTACCTTGATCCTATGGACTACTGGGGTCAAGGAACCT
CAGTCACCGTCTCCTCA (SEQ ID NO: 25)

Light chain of MWTx-003:
Protein sequence of the variable region:
DIVMTQSHKFMSTSVGDRVSITCKASQDVTTAVAWYQQKPGQSPKILIYWATTRHTGV
PDRFTGSISGTTYILTISSVQAEDLALYYCQQHYSTPYTFGGGTKLEIK (SEQ ID NO: 26)

| LC CDR-1 | LC CDR-2 | LC CDR-3 |
|---|---|---|
| QDVTTA (SEQ ID NO: 27) | WAT (SEQ ID NO: 28) | QQHYSTPYT (SEQ ID NO: 29) |

Nucleotide sequence of the variable region:
GACATTGTGATGACCCAGTCTCACAAATTCATGTCCACATCAGTAGGAGACAGGGT
CAGCATCACCTGCAAGGCCAGTCAGGATGTGACTACTGCTGTCGCCTGGTATCAAC
AAAAACCAGGACAGTCTCCTAAAATACTGATTTACTGGGCAACCACCCGGCACACT
GGAGTCCCTGATCGCTTCACAGGCAGTATATCTGGGACAACTTATATTCTCACCATC
AGTAGTGTGCAGGCTGAAGACCTGGCACTTTATTACTGTCAGCAACATTATAGCAC
TCCGTACACGTTCGGAGGGGGGACCAAGCTGGAAATAAAA (SEQ ID NO: 30)

Generation and Screening of Humanized Anti-TMPRSS6 Antibody Variants

Humanization of the parental antibody was performed utilizing CDR grafting onto human antibody frameworks. Homology modeling of the parental antibody's 3-dimensional structure was first performed to establish a structural model of the parental antibody. Amino acid sequences for the variable fragment framework were identified based on the overall sequence identity, matching VH-VL interface positions, similarly classed CDR canonical positions, and removal of potential N-glycosylation sites. Humanized antibodies were designed by creating multiple hybrid sequences that fuse selected parts of the parental antibody sequence with the human framework sequences. The isotypes chosen to format humanized antibody were IgG1 for the heavy chain and IgG1 kappa for the light chain. Using the 3D model, these humanized sequences were methodically analyzed by eye and computer modeling to isolate the sequences that would most likely retain antigen binding. The goal was to maximize the amount of human sequence in the final humanized antibodies while retaining the original antibody specificity. Humanized variants, pairing the humanized VH and VL were then expressed and purified for affinity analysis.

In one round of designing, generating, and testing variants as part of an affinity analysis, four VH variants were generated with the VH-CDRs of the parental antibody MWTX-003 in corresponding positions in four different human IgG1-derived frameworks (SEQ ID NOS: 89-92), and four VL (VK) variants were generated with the VL-CDRs of the parental antibody MWTX-003 in corresponding positions in four different human IgG1 kappa-derived frameworks (SEQ ID NOS: 93-96). A total of sixteen (16) humanized variants representing every combination of the VH and VL (VK) variants were prepared according to a 4VH×4VK matrix, evaluated for antigen binding characteristics ($k_{on}$, $k_{off}$, KD) and found to have KD values in the nanomolar range, from 4.16E-07 (to 1.09E-08.

Variants that showed desired antigen binding affinity were selected for further evaluation and development. In some cases, parental CDR sequences were modified to avoid potential unwanted events such as aspartate isomerization.

To silence antibody effector function, in particular to silence antibody-dependent cellular cytotoxicity (ADCC), critical amino acid residues in the Fc region were identified and mutated (substituted) for all of the humanized antibody variants. Guidance available in the published literature concerning Fc mutations to achieve the goal of abolishing ADCC was used to inform the present mutations, for example removal of the native Fc N-linked glycosylation site (N297A mutation) in hIgG1, or substitutions of leucine at positions 234 and 235 of the lower hinge region in the Fc (LALA double mutation) as described by (Tamm A, Schmidt R E. IgG binding sites on human Fc gamma receptors. *Int Rev Immunol.* 1997; 16(1-2):57-85. doi: 10.3109/08830189709045703; Jefferis R, Lund J. Interaction sites on human IgG-Fc for FcgammaR: current models. Immunol Lett. 2002 Jun. 3; 82(1-2):57-65. doi: 10.1016/s0165-2478(02)00019-6). In the present variants, the N297A mutation was introduced in the Fc of the hzMWTx-001Var and hzMWTx-002Var antibodies, and the LALA mutation was introduced into the Fc of the hzMWTx-003Var antibody, to achieve the same goal of reducing or silencing ADCC (Table 3, SEQ ID NOs: 73, 77, 81).

After evaluation, humanized anti-TMPRSS6 antibody variants hzMWTx-001Var, hzMWTx-002Var, and hzMWTx-003Var were selected for further testing. Sequences and features of humanized variants are shown in Tables 2 and 3 below.

Recombinant Production of Humanized Anti-TMPRSS6 Antibody Variants

Expression constructs for humanized anti-TMPRSS6 antibody variants were engineered with internal ribosome entry site (IRES) between LC- and HC-coding DNA sequences, codon optimized by Geneart DNA synthesis and cloned into pcDNA3.4 mammalian expression vector (ThermoFisher). The sequences of DNA inserts were verified by sequencing. For recombinant antibody production, the expression constructs were used for transient transfection using ExpiCHO expression system (ThermoFisher) following manufacturer's instruction. The expressed antibodies were purified by Protein A affinity chromatography. The yield of antibody production from transient transfection ranged from 50 mg to 300 mg per liter, with purity >95% and <1 EU/ml endotoxin level.

Sequences of Humanized Anti-TMPRSS6 Antibody Variants hzMWTx-001Var, hzMWTx-002Var, and hzMWTx-003Var Humanized anti-TMPRSS6 antibody variants hzMWTx-001Var, hzMWTx-002Var, and hzMWTx-003Var were selected for further testing. Sequences of the variable region of each variable region are shown in Table 2 below, where identified CDRs are indicated by underlining and changes made in the humanized variant CDR sequences relative to the parental antibody are indicated and discussed.

TABLE 2

Amino acid and nucleotide sequences of variable regions of humanized anti-TMPRSS6 antibody variants hzMWTx-001Var, hzMWTx-002Var, and hzMWTx-003Var hzMWTx-001Var
Heavy chain of hzMWTx-001Var:
Protein sequence of variable region (CDR residues that differ from parental sequence in bold):
EVQLVQSGAEVKKPGASVKVSCKASGYTFTSYWITWVRQAPGQRLEWIGNIYPGSGST
YYNEKFKSKATITRDTSSRTAYMELSSLRSEDTAVYYCAPYDADYAMDYWGQGTLVT
VSS (SEQ ID NO: 31)

| hzMWTx-001Var HC CDR-1 | hzMWTx-001Var HC CDR-2 | hzMWTx-001Var HC CDR-3 |
|---|---|---|
| GYTFTSYW (SEQ ID NO: 32) | IYPGSGST (SEQ ID NO: 33) | APYDADYAMDY (SEQ ID NO: 34) |

Comment on underlined sequence DA in hzMWTx-001Var HC CDR-2:
Original sequence in parental antibody is DS here. It was determined that DS is a critical combination that could result in aspartate isomerization, so S (Serine) at this position was changed to A (Alanine).

Nucleotide sequence of the variable region:
GAAGTGCAGCTGGTGCAATCTGGCGCCGAAGTGAAGAAACCTGGCGCCTCTGTGAA
GGTGTCCTGCAAGGCTTCCGGCTACACCTTTACCAGCTACTGGATCACCTGGGTCCG
ACAGGCTCCTGGCCAGAGACTGGAATGGATCGGCAACATCTACCCTGGCTCCGGCT
CCACCTACTACAACGAGAAGTTCAAGTCCAAGGCCACAATCACCCGGGACACCTCT
TCCAGAACCGCCTACATGGAACTGTCCAGCCTGAGATCTGAGGACACCGCCGTGTA
CTACTGCGCCCCTTACGACGCCGACTACGCCATGGATTATTGGGGCCAGGGCACCC
TGGTCACCGTGTCCTCT (SEQ ID NO: 35)

Light chain of hzMWTx-001Var:
Protein sequence of variable region (CDR residues that differ from parental sequence in bold):
DIQMTQSPSSLSASVGDRVTITCKASQDISNYLSWFQQKPGKAPKLLIYRANRLVEGVPS
RFSGSGSGTDFTLTISSLQPEDFATYFCLQYDEFPLTFGGGTKVEIK (SEQ ID NO: 36)

TABLE 2-continued Amino acid and nucleotide sequences of variable regions of humanized anti-TMPRSS6 antibody variants hzMWTx-001Var, hzMWTx-002Var, and hzMWTx-003Var

| hzMWTx-001Var LC CDR-1 | hzMWTx-001Var LC CDR-2 | hzMWTx-001Var LC CDR-3 |
|---|---|---|
| QDI<u>SN</u>Y (SEQ ID NO: 37) | RAN (SEQ ID NO: 38) | LQYDEFPLT (SEQ ID NO: 39) |

Comment on underlined sequence <u>SN</u> in hzMWTx-001Var LC CDR-1: Original sequence in parental antibody is NN here. It was determined that NN is a critical combination that could result in asparagine deamidation, so N (Asparagine) at this position was changed to S (Serine).

Nucleotide sequence of the variable region:
GACATCCAGATGACCCAGTCTCCATCCTCTCTGTCCGCCTCTGTGGGCGACAGAGTG
ACCATCACATGCAAGGCCAGCCAGGACATCTCCAACTACCTGTCCTGGTTCCAGCA
GAAGCCTGGCAAGGCTCCCAAGCTGCTGATCTACAGAGCCAACAGACTGGTGGAA
GGCGTGCCCTCCAGATTCTCCGGATCTGGCTCTGGCACCGACTTTACCCTGACAATC
TCCAGCCTGCAGCCTGAGGACTTCGCTACCTACTTCTGCCTGCAATACGACGAGTTC
CCTCTGACCTTTGGCGGAGGCACCAAGGTGGAAATCAAG (SEQ ID NO: 40)

hzMWTx-002Var
Heavy chain of hzMWTx-002Var:
Protein sequence of variable region (CDR residues that differ from parental sequence in bold):
EVQLVQSGAEVKKPGASVKVSCKASG<u>FNIKDYY</u>IHWVRQATGQGLEWMGR<u>IDPEDAE
S</u>EYAPKFQGRVTITADTSTDTAYMELSSLRSEDTAVYYC<u>TRGDSMMVTYFDY</u>WGQGT
LVTVSS (SEQ ID NO: 41)

| hzMWTx-002Var HC CDR-1 | hzMWTx-002Var HC CDR-2 | hzMWTx-002Var HC CDR-3 |
|---|---|---|
| GFNIKDYY (SEQ ID NO: 42) | IDPED<u>A</u>ES (SEQ ID NO: 43) | TRGDSMMVTYFDY (SEQ ID NO: 44) |

Comment on underlined sequence <u>DA</u> in hzMWTx-002Var HC CDR-2: Original sequence in parental antibody is DG here. It was determined that DG is a critical combination that could likely result in aspartate isomerization, so G (Glycine) at this position was changed to A (Alanine).

Nucleotide sequence of the variable region:
GAAGTGCAGCTGGTGCAATCTGGCGCCGAAGTGAAGAAACCTGGCGCCTCTGTGAA
GGTGTCCTGCAAGGCCTCTGGCTTCAACATCAAGGACTACTACATCCACTGGGTCC
GACAGGCTACCGGACAGGGACTTGAGTGGATGGGCAGAATCGACCCTGAGGACGC
CGAGTCTGAGTACGCCCCTAAGTTTCAGGGCAGAGTGACCATCACCGCCGACACCT
CTACCGACACCGCCTACATGGAACTGTCCAGCCTGAGATCTGAGGACACCGCCGTG
TACTACTGCACCAGAGGCGACTCCATGATGGTTACCTACTTCGACTACGGGGCCA
GGGCACCCTGGTCACAGTTTCTTCC (SEQ ID NO: 45)

Light chain of hzMWTx-002Var:
Protein sequence of variable region:
DIQMTQSPSSLSASVGDRVTITCKASQDVSTAVAWYQQKPGKAPKLLIYWAFTRHTGV
PSRFSGSGSGTDYALTISSLQPEDFATYYCQQHYRSPWTFGGGTKVEIK (SEQ ID NO: 46)

| hzMWTx-002Var LC CDR-1 | hzMWTx-002Var LC CDR-2 | hzMWTx-002Var LC CDR-3 |
|---|---|---|
| QDVSTA (SEQ ID NO: 47) | WAF (SEQ ID NO: 48) | QQHYRSPWT (SEQ ID NO: 49) |

Nucleotide sequence of the variable region:
GACATCCAGATGACCCAGTCTCCATCCTCTCTGTCCGCCTCTGTGGGCGACAGAGTG
ACCATCACATGCAAGGCCTCTCAGGACGTGTCCACCGCCGTTGCTTGGTATCAGCA
GAAGCCTGGCAAGGCCCCTAAGCTGCTGATCTACTGGGCCTTCACCAGACACACCG
GCGTGCCCTCTAGGTTCTCCGGCTCTGGCTCTGGCACCGATTACGCTCTGACAATCT
CCAGCCTGCAGCCTGAGGACTTCGCCACCTACTACTGCCAGCAGCACTACAGAAGC
CCCTGGACATTTGGCGGAGGCACCAAGGTGGAAATCAAG (SEQ ID NO: 50)

TABLE 2-continued

Amino acid and nucleotide sequences of variable regions of humanized anti-TMPRSS6 antibody variants hzMWTx-001Var, hzMWTx-002Var, and hzMWTx-003Var hzMWTx-003Var
Heavy chain of hzMWTx-003Var:
Protein sequence of variable region (CDRs indicated by underlining; CDR residues that differ from parental CDR sequence indicated in bold):
QVQLVQSGAEVKKPGASVKVSCKAS<u>GFNIEDYY</u>MHWVRQAPGQRLEWMG<u>RIDPEDA</u>
ETTYSPKFQGRVTIIPDTSANTAYMELSSLRSEDTAVYYC<u>ARSIYLDPMDY</u>WGQGTLVT
VSS (SEQ ID NO: 51)

| hzMWTx-003Var HC CDR-1 | hzMWTx-003Var HC CDR-2 | hzMWTx-003Var HC CDR-3 |
|---|---|---|
| GFNIEDYY (SEQ ID NO: 52) | IDPEDAET (SEQ ID NO: 53) | ARSIYLDPMDY (SEQ ID NO: 54) |

Comment on underlined sequence DA in hzMWTx-003Var HC CDR-2:
Original sequence in parental antibody is DG here. It was determined that DG is a critical combination that could likely result in aspartate isomerization, so G (Glycine) at this position was changed to A (Alanine).

Nucleotide sequence of the variable region:
CAGGTGCAGCTGGTGCAGTCTGGCGCCGAAGTGAAAAAGCCTGGCGCCTCTGTGAA
GGTGTCCTGCAAGGCCTCTGGCTTCAACATCGAGGACTACTACATGCACTGGGTCC
GACAGGCCCCTGGCCAGAGATTGGAATGGATGGGCAGAATCGACCCCGAGGACGC
CGAGACAACCTACTCTCCTAAGTTCCAGGGCCGCGTGACAATCATCCCTGACACCT
CTGCCAACACCGCCTACATGGAACTGTCCAGCCTGAGATCTGAGGACACCGCCGTG
TACTACTGCGCCCGGTCTATCTACCTGGACCCTATGGACTATTGGGGCCAGGGCAC
CCTGGTCACAGTGTCCTCT (SEQ ID NO: 55)

Light chain of hzMWTx-003Var:
Protein sequence of variable region:
DIQMTQSPKSLSASVGDRVTITCRAS<u>QDVTTA</u>LAWYQQKPGQSPKLLIY<u>WAT</u>TRHSGV
PSRFSGSGSGTDFTLTISSLQPEDFATYYC<u>QQHYSTPYT</u>FGQGTKLEIK (SEQ ID NO: 56)

| hzMWTx-003Var LC CDR-1 | hzMWTx-003Var LC CDR-2 | hzMWTx-003Var LC CDR-3 |
|---|---|---|
| QDVTTA (SEQ ID NO: 57) | WAT (SEQ ID NO: 58) | QQHYSTPYT (SEQ ID NO: 59) |

Nucleotide sequence of the variable region:
GACATCCAGATGACCCAGTCTCCAAAGTCTCTGTCCGCCTCCGTGGGCGACAGAGT
GACCATCACCTGTAGAGCCTCTCAGGACGTGACCACCGCTCTGGCTTGGTATCAGC
AGAAGCCTGGCCAGTCTCCTAAGCTGCTGATCTACTGGGCCACCACCAGACACTCT
GGCGTGCCCTCTAGATTCTCCGGCTCTGGCTCTGGCACCGACTTTACCCTGACAATC
TCCAGCCTGCAGCCTGAGGACTTCGCCACCTACTACTGCCAGCAGCACTACAGCAC
CCCTTACACCTTTGGCCAGGGCACCAAGCTGGAAATCAAG (SEQ ID NO: 60)

Table 3 shows complete heavy chain and light chain protein and nucleotide sequences of anti-TMPRSS6 monoclonal antibodies MWTx-001, MWTx-002, and MWTx-003, and humanized anti-TMPRSS6 antibody variants hzMWTx-001Var, hzMWTx-002Var, and hzMWTx-003Var. Heavy chain protein sequences of humanized anti-TMPRSS6 antibody variants hzMWTx-001Var, hzMWTx-002Var, and hzMWTx-003Var show the location of mutations (changes) introduced to reduce ADCC as described above.

TABLE 3

Heavy chain and light chain sequences of anti-TMPRSS6 monoclonal antibodies MWTx-001, MWTx-002, and MWTx-003, and humanized anti-TMPRSS6 antibody variants hzMWTx-001Var, hzMWTx-002Var, and hzMWTx-003Var Anti-TMPRSS6 monoclonal antibodies
MWTx-001
Heavy chain of MWTx-001:
Protein sequence (Constant region indicated by italics):
QVQLQQPGAELAKPGASVKMSCKASGYTFTSYWITWVKQRPGQDLEWIGNIYPGSGST
YYNEKFKSKATLTVDTSSRTAYMQLSSLTSADSAVYYCAPYDSDYAMDYWGQGTSVT
VSS*AKTTAPSVYPLAPVCGDTTGSSVTLGCLVKGYFPEPVTLTWNSGSLSSGVHTFPAVLQSD*

TABLE 3-continued

Heavy chain and light chain sequences of anti-TMPRSS6 monoclonal antibodies MWTx-001, MWTx-002, and MWTx-003, and humanized anti-TMPRSS6 antibody variants hzMWTx-001Var, hzMWTx-002Var, and hzMWTx-003Var

*LYTLSSSVTVTSSTWPSQSITCNVAHPASSTKVDKKIEPRGPTIKPCPPCK-
CPAPNLLGGPSVFI
FPPKIKDVLMISLSPIVTCVVVDVSEDDPDVQISWFVNNVEVHTAQTQTHREDYNSTLRVVSA
LPIQHQDWMSGKEFKCKVNNKDLPAPIERTISKPKGSVRAPQVYVLPPPEEEMTKKQVTLTC
MVTDFMPEDIYVEWTNNGKTELNYKNTEPVLDSDGSYFMYSKLRVEKKNWVERNSYSCSVV
HEGLHNHHTTKSFSRTPG* (SEQ ID NO: 61)

Nucleotide sequence:
CAGGTCCAACTGCAGCAGCCTGGGGCTGAGCTTGCGAAGCCTGGGGCTTCAGTGAAGA
TGTCCTGCAAGGCTTCTGGCTACACCTTCACCAGCTACTGGATAACCTGGGTGAAGCAG
AGGCCTGGACAAGACCTTGAGTGGATTGGAAATATTTATCCTGGTAGTGGTAGTACTTA
CTACAATGAGAAGTTCAAGAGCAAGGCCACACTGACTGTAGACACATCCTCCAGAACA
GCCTACATGCAGCTCAGCAGTCTGACATCTGCGGACTCTGCGGTCTATTACTGTGCCCCC
TATGATTCCGACTATGCTATGGACTACTGGGGTCAAGGAACCTCAGTCACCGTCTCCTC
AGCTAAAACAACAGCCCCATCGGTCTATCCACTGGCCCCTGTGTGTGGAGATACAACTG
GCTCCTCGGTGACTCTAGGATGCCTGGTCAAGGGTTATTTCCCTGAGCCAGTGACCTTG
ACCTGGAACTCTGGTTCCCTGTCCAGTGGTGTGCACACCTTCCCAGCTGTCCTGCAGTCT
GACCTCTACACCCTCAGCTCAAGCGTGACTGTAACCAGCTCGACCTGGCCCAGCCAGTC
CATCACCTGCAATGTGGCCCACCCGGCAAGCAGCACCAAGGTGGACAAGAAAATTGAG
CCCAGAGGGCCCACAATCAAGCCCTGTCCTCCATGCAAATGCCCAGCACCTAACCTCTT
GGGTGGACCATCCGTCTTCATCTTCCCTCCAAAGATCAAGGATGTACTCATGATCTCCCT
GAGCCCCATAGTCACATGTGTAGTCGTTGATGTGAGCGAGGATGACCCAGATGTCCAGA
TCAGCTGGTTTGTGAACAACGTGGAAGTGCACACTGCTCAGACACAGACGCATAGAGA
GGATTACAACAGTACTCTCCGGGTTGTCAGTGCCCTCCCCATCCAGCACCAGGACTGGA
TGAGTGGCAAGGAGTTCAAATGCAAGGTCAACAACAAAGACCTCCCAGCGCCCATCGA
GAGAACCATCTCAAAACCCAAAGGGTCAGTAAGAGCTCCACAGGTATATGTCTTGCCTC
CACCAGAAGAGGAGATGACTAAGAAACAGGTCACTCTGACCTGCATGGTCACAGACTT
CATGCCTGAAGACATTTACGTGGAGTGGACCAACAACGGGAAAACAGAGCTAAACTAC
AAGAACACTGAACCAGTCCTGGACTCTGATGGTTCTTACTTCATGTACAGCAAGCTGAG
AGTGGAAGAAGAACTGGGTGGAGAGAAATAGCTACTCCTGTTCAGTGGTCCACGAG
GGTCTGCACAATCACCACACGACTAAGAGCTTCTCCCGGACTCCGGGTTAGTAA (SEQ ID NO: 62)

Light chain of MWTx-001:
Protein sequence (Constant region indicated by italics):
DIKMTQSPSSMYASLGERVTITCKASQDINNYLSWFQQKPGKSPKTLIYRANRLVDGVP
SRVSGSGSGQDYSLTISSLEYEDVGIYFCLQYDEFPLTFGAGTKLELK*RADAAPTVSIFPPS
SEQLTSGGASVVCFLNNFYPKDINVKWKIDGSERQNGVLNSWTDQDSKDSTYSMSSTLTLTK
DEYERHNSYTCEATHKTSTSPIVKSFNRNEC* (SEQ ID NO: 63)

Nucleotide sequence:
GACATCAAGATGACCCAGTCTCCATCTTCCATGTATGCATCTCTAGGAGAGAGAGTCAC
TATCACTTGCAAGGCGAGTCAGGACATTAATAACTATTTAAGCTGGTTCCAGCAGAAAC
CAGGGAAATCTCCTAAGACCCTGATCTATCGTGCAAACAGATTGGTAGATGGGGTCCCA
TCAAGGGTCAGTGGCAGTGGATCTGGGCAAGATTATTCTCTCACCATCAGCAGCCTGGA
GTATGAAGATGTGGGAATTTATTTTTGTCTACAGTATGATGAGTTTCCTCTCACGTTCGG
TGCTGGGACCAAGCTGGAGCTGAAAAGAGCTGACGCCGCTCCTACCGTGTCCATCTTTC
CACCTAGCAGCGAGCAGCTGACAAGCGGCGGAGCCAGCGTCGTGTGCTTCCTGAACAA
CTTCTACCCCAAGGACATCAACGTGAAGTGGAAGATCGACGGCAGCGAGAGACAGAAC
GGCGTGCTGAATAGCTGGACCGACCAGGACAGCAAGGACTCCACCTACAGCATGTCCA
GCACACTGACCCTGACCAAGGACGAGTACGAGCGGCACAACAGCTACACATGCGAGGC
CACACACAAGACCAGCACAAGCCCCATCGTGAAGTCCTTCAACCGGAACGAGTGC (SEQ ID NO: 64)

MWTx-002
Heavy chain of MWTx-002:
Protein sequence (Constant region indicated by italics):
EVQLQQSGAELVKPGASVKLSCTASGFNIKDYYIHWVKERTEQGLEWFGRIDPEDGESE
YAPKFQGKATLTADTSSNTAYLQLSSLTSEDTAVYYCTRGDSMMVTYFDYWGQGTTL
TVSS*KTTPPSVY-
PLAPGCGDTTGSSVTLGCLVKGYFPESVTVTWNSGSLSSSVHTFPALLQSGL
YTMSSSVTVPSSTWPSQTVTCSVAHPASSTTVDKKLEPSGPISTINPCPPCKE-
CHKCPAPNLEG
GPSVFIFPPNIKDVLMISLTPKVTCVVVDVSEDDPDVQISWFVNNVEVHTAQTQTHREDYNST
IRVVSTLPIQHQDWMSGKEFKCKVNNKDLPSPIERTISKIKGLVRAPQVYILPP-
PAEQLSRKDV
SLTCLVVGFNPGDISVEWTSNGHTEENYKDTAPVLDSDGSYFIYSKLNMKTSKWEKTDSFSCN
VRHEGLKNYYLKKTISRSPGK* (SEQ ID NO: 65)

Nucleotide sequence:
GAGGTTCAGCTGCAGCAGTCTGGGGCAGAACTTGTGAAGCCAGGGGCCTCAGTCAAGT
TGTCCTGCACAGCCTCTGGCTTCAACATTAAAGACTACTATATACACTGGGTGAAAGAG
AGGACTGAACAGGGCCTGGAGTGGTTTGGAAGGATTGATCCTGAGGATGGTGAAAGTG
AATATGCCCCGAAATTCCAGGGCAAGGCCACTTTAACAGCAGACACATCCTCCAATACA

TABLE 3-continued

Heavy chain and light chain sequences of anti-TMPRSS6 monoclonal antibodies MWTx-001, MWTx-002, and MWTx-003, and humanized anti-TMPRSS6 antibody variants hzMWTx-001Var, hzMWTx-002Var, and hzMWTx-003Var GCCTACCTGCAGCTCAGCAGCCTGACATCTGAGGACACTGCCGTCTATTACTGTACTAG
AGGAGACTCTATGATGGTTACCTACTTTGACTACTGGGGCCAAGGCACCACTCTCACGG
TCTCCTCAAAGACCACACCTCCTAGCGTGTACCCTCTGGCTCCTGGCTGTGGCGATACA
ACAGGCAGCTCTGTGACACTGGGCTGCCTGGTCAAGGGCTACTTTCCTGAGAGCGTGAC
AGTGACCTGGAACAGCGGCAGCCTGTCTAGCAGCGTGCACACCTTTCCAGCTCTGCTCC
AGAGCGGCCTGTACACCATGTCCTCTAGTGTGACCGTGCCTAGCAGCACCTGGCCTAGC
CAGACAGTGACATGTAGCGTGGCCCATCCTGCCAGCAGCACAACCGTGGACAAGAAGC
TGGAACCTAGCGGCCCCATCAGCACCATCAATCCCTGTCCTCCATGCAAAGAATGCCAC
AAGTGCCCCGCTCCTAACCTGGAAGGTGGCCCAAGCGTGTTCATCTTCCCACCTAACAT
CAAGGACGTGCTGATGATCAGCCTGACACCTAAAGTGACCTGCGTGGTGGTGGACGTGT
CCGAGGATGATCCCGATGTGCAGATCAGTTGGTTCGTGAACAACGTGGAAGTGCACAC
AGCCCAGACACAGACCCACAGAGAGGACTACAATAGCACCATTCGCGTGGTGTCCACA
CTGCCTATCCAGCACCAGGATTGGATGAGCGGCAAAGAGTTCAAGTGCAAAGTGAACA
ACAAGGACCTGCCTTCTCCAATCGAGCGGACCATCAGCAAGATCAAGGGACTCGTCAG
AGCCCCTCAGGTGTACATCTTGCCTCCACCAGCCGAGCAGCTGAGCAGAAAGGATGTGT
CCCTGACCTGTCTGGTCGTGGGCTTCAACCCTGGCGACATCAGCGTGGAATGGACCAGC
AATGGCCACACCGAGGAAAACTACAAGGACACAGCCCCTGTGCTGGACAGCGACGGCA
GCTACTTCATCTACAGCAAGCTGAACATGAAGACCAGCAAGTGGGAGAAAACCGACAG
CTTCTCCTGCAACGTGCGGCACGAGGGCCTGAAGAACTACTACCTGAAGAAACCATCT
CTCGGAGCCCCGGCAAG (SEQ ID NO: 66)

Light chain of MWTx-002:
Protein sequence (Constant region indicated by italics):
DIVMTQSHKFMSTSVGDRVSITCKASQDVSTAVAWYQQKPGQSPKLLIYWAFTRHTGV
PDRFTSTGSGTDYALTISSVQAEDLALYYCQQHYRSPWTFGGGTKLEIK*RADAAPTVSIF*
*PPSSEQLTSGGASVVCFLNNFYPKDINVKWKIDGSERQNGVLNSWTDQDSKDSTYSMSSTLTL*
*TKDEYERHNSYTCEATHKTSTSPIVKSFNRNEC* (SEQ ID NO: 67)

Nucleotide sequence:
GACATTGTGATGACCCAGTCTCACAAATTCATGTCCACATCAGTAGGAGACAGGGTCAG
CATCACCTGCAAGGCCAGTCAGGATGTGAGTACTGCTGTAGCCTGGTATCAACAAAAAC
CAGGGCAATCTCCTAAACTACTGATTTACTGGGCTTTCACCCGTCACACTGGAGTCCCTG
ATCGCTTCACAAGCACTGGATCTGGGACAGATTATGCTCTCACCATCAGCAGTGTGCAG
GCTGAAGACCTGGCACTTTATTACTGTCAGCAACATTATCGCAGTCCGTGGACGTTCGG
TGGAGGCACCAAACTGGAAATCAAAAGAGCTGACGCCGCTCCTACCGTGTCCATCTTTC
CACCTAGCAGCGAGCAGCTGACAAGCGGCGGAGCCAGCGTCGTGTGCTTCCTGAACAA
CTTCTACCCCAAGGACATCAACGTGAAGTGGAAGATCGACGGCAGCGAGAGACAGAAC
GGCGTGCTGAATAGCTGGACCGACCAGGACAGCAAGGACTCCACCTACAGCATGTCCA
GCACACTGACCCTGACCAAGGACGAGTACGAGCGGCACAACAGCTACACATGCGAGGC
CACACACAAGACCAGCACAAGCCCCATCGTGAAGTCCTTCAACCGGAACGAGTGC
(SEQ ID NO: 68)

MWTx-003
Heavy chain of MWTx-003:
Protein sequence (Constant region indicated by italics):
EVQLQQSGAELVKPGASVKLSCTASGFNIEDYYIHWVKERTEQGLEWIGRIDPEDGETT
YAPQFQGKATIIPDTSSNTAYMQLSSLTSEDAAVYYCARSIYLDPMDYWGQGTSVTVSS
*KTTPPSVYPLAPGCGDTTGSSVTLGCLVKGYFPESVTVTWNSGSLSSSVHTFPALLQSG-*
*LYTMS*
*SSVTVPSSTWPSQTVTCSVAHPASSTTVDKKLEPSGPISTINPCPPCKECHKCPAPN-*
*LEGGPSV*
*FIFPPNIKDVLMISLTPKVTCVVVDVSEDDPDVQISWFVNNVEVHTAQTQTHREDYNSTIRVV*
*STLPIQHQDWMSGKEFKCKVNNKDLPSPIERTISKIKGLVRAPQVYILPP-*
*PAEQLSRKDVSLTC*
*LVVGFNPGDISVEWTSNGHTEENYKDTAPVLDSDGSYFIYSKLNMKTSKWEKTDSFSCNVRH*
*EGLKNYYLKKTISRSPGK* (SEQ ID NO: 69)

Nucleotide sequence:
GAGGTTCAGCTGCAGCAGTCTGGCGCCGAGCTTGTGAAACCTGGCGCCTCTGTGAAGCT
GAGCTGTACCGCCAGCGGCTTCAACATCGAGGACTACTACATCCACTGGGTCAAAGAGC
GGACCGAGCAGGGACTCGAGTGGATCGGAAGAATCGACCCCGAGGACGGCGAGACAA
CATACGCCCCTCAGTTTCAGGGCAAAGCCACAATCATCCCCGACACCAGCAGCAACACC
GCCTACATGCAACTGAGCAGCCTGACCTCTGAAGATGCCGCCGTGTACTACTGCGCCCG
GTCCATCTATCTGGACCCCATGGATTATTGGGGCCAGGGCACAAGCGTGACCGTGTCCT
CTAAGACCACACCTCCTAGCGTGTACCCTCTGGCTCCTGGCTGTGGCGATACAACAGGC
AGCTCTGTGACACTGGGCTGCCTGGTCAAGGGCTACTTTCCTGAGAGCGTGACAGTGAC
CTGGAACAGCGGCAGCCTGTCTAGCAGCGTGCACACCTTTCCAGCTCTGCTCCAGAGCG
GCCTGTACACCATGTCCTCTAGTGTGACCGTGCCTAGCAGCACCTGGCCTAGCCAGACA
GTGACATGTAGCGTGGCCCATCCTGCCAGCAGCACAACCGTGGACAAGAAGCTGGAAC
CTAGCGGCCCCATCAGCACCATCAATCCCTGTCCTCCATGCAAAGAATGCCACAAGTGC
CCCGCTCCTAACCTGGAAGGTGGCCCAAGCGTGTTCATCTTCCCACCTAACATCAAGGA
CGTGCTGATGATCAGCCTGACACCTAAAGTGACCTGCGTGGTGGTGGACGTGTCCGAGG
ATGATCCCGATGTGCAGATCAGTTGGTTCGTGAACAACGTGGAAGTGCACACAGCCCAG TABLE 3-continued Heavy chain and light chain sequences of anti-TMPRSS6 monoclonal antibodies MWTx-001, MWTx-002, and MWTx-003, and humanized anti-TMPRSS6 antibody variants hzMWTx-001Var, hzMWTx-002Var, and hzMWTx-003Var

```
ACACAGACCCACAGAGAGGACTACAATAGCCACCATTCGCGTGGTGTCCACACTGCCTAT
CCAGCACCAGGATTGGATGAGCGGCAAAGAGTTCAAGTGCAAAGTGAACAACAAGGAC
CTGCCTTCTCCAATCGAGCGGACCATCAGCAAGATCAAGGGACTCGTCAGAGCCCCTCA
GGTGTACATCTTGCCTCCACCAGCCGAGCAGCTGAGCAGAAAGGATGTGTCCCTGACCT
GTCTGGTCGTGGGCTTCAACCCTGGCGACATCAGCGTGGAATGGACCAGCAATGGCCAC
ACCGAGGAAAACTACAAGGACACAGCCCCTGTGCTGGACAGCGACGGCAGCTACTTCA
TCTACAGCAAGCTGAACATGAAGACCAGCAAGTGGGAGAAAACCGACAGCTTCTCCTG
CAACGTGCGGCACGAGGGCCTGAAGAACTACTACCTGAAGAAAACCATCTCTCGGAGC
CCCGGCAAG (SEQ ID NO: 70)
```

Light chain of MWTx-003:
Protein sequence (Constant region indicated by italics):
DIVMTQSHKFMSTSVGDRVSITCKASQDVTTAVAWYQQKPGQSPKILIYWATTRHTGV
PDRFTGSISGTTYILTISSVQAEDLALYYCQQHYSTPYTFGGGTKLEIKR*ADAAPTVSIFPP*
*SSEQLTSGGASVVCFLNNFYPKDINVKWKIDGSERQNGVLNSWTDQDSKDSTYSMSSTLTLTK*
*DEYERHNSYTCEATHKTSTSPIVKSFNRNEC* (SEQ ID NO: 71)

Nucleotide sequence:
```
GACATCGTGATGACCCAGAGCCACAAGTTCATGAGCACCAGCGTGGGCGACAGAGTGT
CCATCACCTGTAAAGCCAGCCAGGACGTGACAACAGCCGTGGCCTGGTATCAGCAGAA
GCCTGGCCAGTCTCCTAAGATCCTGATCTACTGGGCCACCACCAGACACACCGGCGTGC
CAGATAGATTCACCGGCAGCATCAGCGGCACCACCTACATCCTGACAATCAGCTCTGTG
CAGGCCGAGGATCTGGCCCTGTACTACTGTCAGCAGCACTACAGCACCCCTTACACCTT
TGGCGGAGGCACCAAGCTGGAAATCAAGAGAGCTGACGCCGCTCCTACCGTGTCCATCT
TTCCACCTAGCAGCGAGCAGCTGACAAGCGGCGGAGCCAGCGTCGTGTGCTTCCTGAAC
AACTTCTACCCCAAGGACATCAACGTGAAGTGGAAGATCGACGGCAGCGAGAGACAGA
ACGGCGTGCTGAATAGCTGGACCGACCAGGACAGCAAGGACTCCACCTACAGCATGTC
CAGCACACTGACCCTGACCAAGGACGAGTACGAGCGGCACAACAGCTACACATGCGAG
GCCACACACAAGACCAGCACAAGCCCCATCGTGAAGTCCTTCAACCGGAACGAGTGC
(SEQ ID NO: 72)
```

Humanized anti-TMPRSS6 antibody variants
hzMWTx-001Var
Heavy chain of hzMWTx-001Var:
Protein sequence (Constant region indicated by italics; N297A mutation indicated by bold):
EVQLVQSGAEVKKPGASVKVSCKASGYTFTSYWITWVRQAPGQRLEWIGNIYPGSGST
YYNEKFKSKATITRDTSSRTAYMELSSLRSEDTAVYYCAPYDADYAMDYWGQGTLVT
VSS*ASTKGPSVFPLAPSSKSTSGGTAALGCLVKDYFPEPVTVSWNSGALTSGVHTFPAVLQSS*
*GLYSLSSVVTVPSSSLGTQTYICNVNHKPSNTKVDKKVEPKSCDKTHTCPPCPAPELLGGPSV*
*FLFPPKPKDTLMISRTPEVTCVVVDVSHEDPEVKFNWYVDGVEVHNAKTKPREEQYASTYRV*
*VSVLTVLHQDWLNGKEYKCKVSNKALPAPIEKTISKAKGQPREPQVYTLPPSRDELTKNQVSL*
*TCLVKGFYPSDIAVEWESNGQPENNYKTTPPVLDSDGSFFLYSKLTVDKSRWQQGNVFSCSV*
*MHEALHNHYTQKSLSLSPG* (SEQ ID NO: 73)

Nucleotide sequence:
```
GAAGTGCAGCTGGTGCAATCTGGCGCCGAAGTGAAGAAACCTGGCGCCTCTGTGAAGG
TGTCCTGCAAGGCTTCCGGCTACACCTTTACCAGCTACTGGATCACCTGGGTCCGACAG
GCTCCTGGCCAGAGACTGGAATGGATCGGCAACATCTACCCTGGCTCCGGCTCCACCTA
CTACAACGAGAAGTTCAAGTCCAAGGCCACAATCACCCGGGACACCTCTTCCAGAACC
GCCTACATGGAACTGTCCAGCCTGAGATCTGAGGACACCGCCGTGTACTACTGCGCCCC
TTACGACGCCGACTACGCCATGGATTATTGGGGCCAGGGCACCCTGGTCACCGTGTCCT
CTGCTTCTACCAAGGGACCCAGCGTGTTCCCTCTGGCTCCTTCCAGCAAGTCTACCTCTG
GCGGAACAGCTGCTCTGGGCTGCCTGGTCAAGGACTACTTTCCTGAGCCTGTGACCGTG
TCTTGGAACTCTGGCGCTCTGACATCCGGCGTGCACACATTTCCAGCTGTGCTGCAGTCC
TCCGGCCTGTACTCTCTGTCCTCTGTCGTGACCGTGCCTTCCTCTAGCCTGGGCACCCAG
ACCTACATCTGCAATGTGAACCACAAGCCTTCCAACACCAAGGTGGACAAGAAGGTGG
AACCCAAGTCCTGCGACAAGACCCACACCTGTCCTCCATGTCCTGCTCCAGAACTGCTC
GGCGGACCTTCCGTGTTCCTGTTTCCTCCAAAGCCTAAGGACACCCTGATGATCTCTCGG
ACCCCTGAAGTGACCTGCGTGGTGGTGGATGTGTCTCACGAGGACCCAGAAGTGAAGTT
CAATTGGTACGTGGACGGCGTGGAAGTGCACAACGCCAAGACCAAGCCTAGAGAGGAA
CAGTACGCCAGCACCTACAGAGTGGTGTCCGTGCTGACAGTGCTGCACCAGGATTGGCT
GAACGGCAAAGAGTACAAGTGCAAGGTGTCCAACAAGGCCCTGCCTGCTCCTATCGAA
AAGACCATCAGCAAGGCCAAGGGCCAGCCTAGAGAACCCCAGGTTTACACCTTGCCTC
CATCTCGGGACGAGCTGACCAAGAACCAGGTGTCCCTGACCTGTCTCGTGAAGGGCTTC
TACCCCTCCGACATCGCCGTGGAATGGGAGTCTAATGGCCAGCCAGAGAACAACTACA
AGACAACCCCTCCTGTGCTGGACTCCGACGGCTCATTCTTCCTGTACTCCAAGCTGACCG
TGGACAAGTCCAGATGGCAGCAGGGCAACGTGTTCTCCTGCTCCGTGATGCACGAGGCC
CTGCACAATCACTACACACAGAAGTCCCTGTCTCTGTCCCCTGGC (SEQ ID NO: 74)
```

TABLE 3-continued

Heavy chain and light chain sequences of anti-TMPRSS6 monoclonal antibodies MWTx-001, MWTx-002, and MWTx-003, and humanized anti-TMPRSS6 antibody variants hzMWTx-001Var, hzMWTx-002Var, and hzMWTx-003Var Light chain of hzMWTx-001Var:
Protein sequence (Constant region indicated by italics):
DIQMTQSPSSLSASVGDRVTITCKASQDISNYLSWFQQKPGKAPKLLIYRANRLVEGVPS
RFSGSGSGTDFTLTISSLQPEDFATYFCLQYDEFPLTFGGGTKVEIKRTV*AAPSVFIFPPSD*
*EQLKSGTASVVCLLNNFYPREAKVQWKVDNALQSGNSQESVTEQDSKDSTYSLSSTLTLSKAD*
*YEKHKVYACEVTHQGLSSPVTKSFNRGEC* (SEQ ID NO: 75)

Nucleotide sequence:
GACATCCAGATGACCCAGTCTCCATCCTCTCTGTCCGCCTCTGTGGGCGACAGAGTGAC
CATCACATGCAAGGCCAGCCAGGACATCTCCAACTACCTGTCCTGGTTCCAGCAGAAGC
CTGGCAAGGCTCCCAAGCTGCTGATCTACAGAGCCAACAGACTGGTGGAAGGCGTGCC
CTCCAGATTCTCCGGATCTGGCTCTGGCACCGACTTTACCCTGACAATCTCCAGCCTGCA
GCCTGAGGACTTCGCTACCTACTTCTGCCTGCAATACGACGAGTTCCCTCTGACCTTTGG
CGGAGGCACCAAGGTGGAAATCAAGCGGACAGTGGCCGCTCCTTCCGTGTTCATCTTCC
CACCTTCCGACGAGCAGCTGAAGTCCGGCACAGCTTCTGTCGTGTGCCTGCTGAACAAC
TTCTACCCTCGGGAAGCCAAGGTGCAGTGGAAGGTGGACAATGCCCTGCAGTCCGGCA
ACTCCCAAGAGTCTGTGACCGAGCAGGACTCCAAGGACAGCACCTACAGCCTGTCCTCC
ACACTGACCCTGTCCAAGGCCGACTACGAGAAGCACAAGGTGTACGCCTGCGAAGTGA
CCCATCAGGGCCTGTCTAGCCCTGTGACCAAGTCTTTCAACCGGGGCGAGTGT (SEQ ID NO: 76)

hzMWTx-002Var
Heavy chain of hzMWTx-002Var:
Protein sequence (Constant region indicated by italics; N297A mutation indicated by bold):
EVQLVQSGAEVKKPGASVKVSCKASGFNIKDYYIHWVRQATGQGLEWMGRIDPEDAE
SEYAPKFQGRVTITADTSTDTAYMELSSLRSEDTAVYYCTRGDSMMVTYFDYWGQGT
LVTVSS*ASTKGPSVFPLAPSSKSTSGGTAALGCLVKDYFPEPVTVSWNSGALTSGVHTFPAVL*
*QSSGLYSLSSVVTVPSSSLGTQTYICNVNHKPSNTKVDKKVEPKSCDKTHTCPPCPAPELLGG*
*PSVFLFPPKPKDTLMISRTPEVTCVVVDVSHEDPEVKFNWYVDGVEVHNAKTKPREEQYAST*
*YRVVSVLTVLHQDWLNGKEYKCKVSNKALPAPIEKTISKAKGQPREPQVYTLPPSRDELTKNQ*
*VSLTCLVKGFYPSDIAVEWESNGQPENNYKTTPPVLDSDGSFFLYSKLTVDKSRWQQGNVFS*
*CSVMHEALHNHYTQKSLSLSPG* (SEQ ID NO: 77)

Nucleotide sequence:
GAAGTGCAGCTGGTGCAATCTGGCGCCGAAGTGAAGAAACCTGGCGCCTCTGTGAAGG
TGTCCTGCAAGGCCTCTGGCTTCAACATCAAGGACTACTACATCCACTGGGTCCGACAG
GCTACCGGACAGGGACTTGAGTGGATGGGCAGAATCGACCCTGAGGACGCCGAGTCTG
AGTACGCCCCTAAGTTTCAGGGCAGAGTGACCATCACCGCCGACACCTCTACCGACACC
GCCTACATGGAACTGTCCAGCCTGAGATCTGAGGACACCGCCGTGTACTACTGCACCAG
AGGCGACTCCATGATGGTTACCTACTTCGACTACTGGGGCCAGGGCACCCTGGTCACGG
TTTCTTCCGCTTCCACCAAGGGACCCAGCGTGTTCCCTCTGGCTCCTTCCAGCAAGTCTA
CCTCTGGCGGAACAGCTGCTCTGGGCTGCCTGGTCAAGGATTACTTCCCTGAGCCTGTG
ACCGTGTCCTGGAACTCTGGCGCTCTGACATCCGGCGTGCACACCTTTCCAGCTGTGCTG
CAATCCTCCGGCCTGTACTCTCTGTCCTCCGTCGTGACCGTGCCTTCTAGCTCTCTGGGC
ACCCAGACCTACATCTGCAATGTGAACCACAAGCCTTCCAACACCAAGGTGGACAAGA
AGGTGGAACCCAAGTCCTGCGACAAGACCCACACCTGTCCTCCATGTCCTGCTCCAGAA
CTGCTCGGCGGACCTTCCGTGTTCCTGTTTCCTCCAAAGCCTAAGGACACCCTGATGATC
TCTCGGACCCCTGAAGTGACCTGCGTGGTGGTGGATGTGTCTCACGAGGACCCAGAAGT
GAAGTTCAATTGGTACGTGGACGGCGTGGAAGTGCACAACGCCAAGACCAAGCCTAGA
GAGGAACAGTACGCCTCCACCTACAGAGTGGTGTCCGTGCTGACAGTGCTGCACCAGG
ATTGGCTGAACGGCAAAGAGTACAAGTGCAAGGTGTCCAACAAGGCACTGCCCGCTCC
TATCGAAAAGACCATCTCCAAGGCCAAGGGCCAGCCTAGAGAACCCCAGGTTTACACC
TTGCCTCCATCTCGGGACGAGCTGACCAAGAACCAGGTGTCCCTGACCTGTCTCGTGAA
GGGCTTCTACCCCTCCGACATCGCCGTGGAATGGGAGTCTAATGGCCAGCCAGAGAACA
ACTACAAGACAACCCCTCCTGTGCTGGACTCCGACGGCTCATTCTTCCTGTACTCCAAGC
TGACCGTGGACAAGTCCAGATGGCAGCAGGGCAACGTGTTCTCCTGCTCCGTGATGCAC
GAGGCCCTGCACAATCACTACACACAGAAGTCTCTGTCCCTGTCTCCTGGC (SEQ ID NO: 78)

Light chain of hzMWTx-002Var:
Protein sequence (Constant region indicated by italics):
DIQMTQSPSSLSASVGDRVTITCKASQDVSTAVAWYQQKPGKAPKLLIYWAFTRHTGV
PSRFSGSGSGTDYALTISSLQPEDFATYYCQQHYRSPWTFGGGTKVEIKRTV*AAPSVFIFP*
*PSDEQLKSGTASVVCLLNNFYPREAKVQWKVDNALQSGNSQESVTEQDSKDSTYSLSSTLTLS*
*KADYEKHKVYACEVTHQGLSSPVTKSFNRGEC* (SEQ ID NO: 79)

Nucleotide sequence:
GACATCCAGATGACCCAGTCTCCATCCTCTCTGTCCGCCTCTGTGGGCGACAGAGTGAC
CATCACATGCAAGGCCTCTCAGGACGTGTCCACCGCCGTTGCTTGGTATCAGCAGAAGC
CTGGCAAGGCCCCTAAGCTGCTGATCTACTGGGCCTTCACCAGACACACCGGCGTGCCC
TCTAGGTTCTCCGGCTCTGGCTCTGGCACCGATTACGCTCTGACAATCTCCAGCCTGCAG TABLE 3-continued Heavy chain and light chain sequences of anti-TMPRSS6 monoclonal antibodies MWTx-001, MWTx-002, and MWTx-003, and humanized anti-TMPRSS6 antibody variants hzMWTx-001Var, hzMWTx-002Var, and hzMWTx-003Var

```
CCTGAGGACTTCGCCACCTACTACTGCCAGCAGCACTACAGAAGCCCCTGGACATTTGG
CGGAGGCACCAAGGTGGAAATCAAGCGGACAGTGGCCGCTCCTTCCGTGTTCATCTTCC
CACCTTCCGACGAGCAGCTGAAGTCCGGCACAGCTTCTGTCGTGTGCCTGCTGAACAAC
TTCTACCCTCGGGAAGCCAAGGTGCAGTGGAAGGTGGACAATGCCCTGCAGTCCGGCA
ACTCCCAAGAGTCTGTGACCGAGCAGGACTCCAAGGACAGCACCTACAGCCTGTCCTCC
ACACTGACCCTGTCCAAGGCCGACTACGAGAAGCACAAGGTGTACGCCTGCGAAGTGA
CCCATCAGGGCCTGTCTAGCCCTGTGACCAAGTCTTTCAACCGGGGCGAGTGT (SEQ ID
NO: 80)
``` hzMWTx-003Var
Heavy chain of hzMWTx-003Var:
Protein sequence (Constant region indicated by italics; LALA mutation indicated by bold):
QVQLVQSGAEVKKPGASVKVSCKASGFNIEDYYMHWVRQAPGQRLEWMGRIDPEDA
ETTYSPKFQGRVTIIPDTSANTAYMELSSLRSEDTAVYYCARSIYLDPMDYWGQGTLVT
*VSSASTKGPSVFPLAPSSKSTSGGTAALGCLVKDYFPEPVTVSWNSGALTSGVHTFPAVLQSS*
*GLYSLSSVVTVPSSSLGTQTYICNVNHKPSNTKVDKKVEPKSCDKTHTCPPCPAPEAAGGPSV*
*FLFPPKPKDTLMISRTPEVTCVVVDVSHEDPEVKFNWYVDGVEVHNAKTKPREEQYNSTYRV*
*VSVLTVLHQDWLNGKEYKCKVSNKALPAPIEKTISKAKGQPREPQVYTLPPSREEMTKNQVS*
*LTCLVKGFYPSDIAVEWESNGQPENNYKTTPPVLDSDGSFFLYSKLTVDKSRWQQGNVFSCS*
*VMHEALHNHYTQKSLSLSPG* (SEQ ID NO: 81)

```
Nucleotide sequence:
CAGGTGCAGCTGGTGCAGTCTGGCGCCGAAGTGAAAAAGCCTGGCGCCTCTGTGAAGG
TGTCCTGCAAGGCCTCTGGCTTCAACATCGAGGACTACTACATGCACTGGGTCCGACAG
GCCCCTGGCCAGAGATTGGAATGGATGGGCAGAATCGACCCCGAGGACGCCGAGACAA
CCTACTCTCCTAAGTTCCAGGGCCGCGTGACAATCATCCCTGACACCTCTGCCAACACC
GCCTACATGGAACTGTCCAGCCTGAGATCTGAGGACACCGCCGTGTACTACTGCGCCCG
GTCTATCTACCTGGACCCTATGGACTATTGGGGCCAGGGCACCCTGGTCACAGTGTCCT
CTGCTTCTACCAAGGGACCCAGCTGTGTTCCCTCTGGCTCCTTCCAGCAAGTCTACCTCTG
GCGGAACAGCTGCTCTGGGCTGCCTGGTCAAGGACTACTTTCCAGAGCCTGTGACCGTG
TCCTGGAACTCTGGCGCTCTGACATCTGGCGTGCACACCTTTCCAGCTGTGCTGCAGTCC
TCCGGCCTGTACTCTCTGTCCTCTGTCGTGACCGTGCCTTCCAGCTCTCTGGGAACCCAG
ACCTACATCTGCAATGTGAACCACAAGCCTTCCAACACCAAGGTGGACAAGAAGGTGG
AACCCAAGTCCTGCGACAAGACCCACACCTGTCCTCCATGTCCTGCTCCAGAAGCTGCT
GGCGGCCCTTCCGTGTTTCTGTTCCCTCCAAAGCCTAAGGACACCCTGATGATCTCTCGG
ACCCCTGAAGTGACCTGCGTGGTGGTGGATGTGTCTCACGAGGACCCAGAAGTGAAGTT
CAATTGGTACGTGGACGGCGTGGAAGTGCACAACGCCAAGACCAAGCCTAGAGAGGAA
CAGTACAACTCCACCTACAGAGTGGTGTCCGTGCTGACCGTGCTGCACCAGGATTGGCT
GAACGGCAAAGAGTACAAGTGCAAGGTGTCCAACAAGGCACTGCCCGCTCCTATCGAA
AAGACCATCTCCAAGGCCAAGGGCCAGCCTAGGGAACCCCAGGTTTACACCCTGCCTCC
AAGCCGGGAAGAGATGACCAAGAACCAGGTGTCCCTGACCTGCCTCGTGAAGGGCTTC
TACCCTTCCGACATCGCCGTGGAATGGGAGAGCAATGGCCAGCCAGAGAACAACTACA
AGACAACCCCTCCTGTGCTGGACTCCGACGGCTCATTCTTCCTGTACTCCAAGCTGACA
GTGGACAAGTCCAGATGGCAGCAGGGCAACGTGTTCTCCTGCTCCGTGATGCACGAGGC
CCTGCACAATCACTACACACAGAAGTCCCTGTCTCTGTCCCCTGGC (SEQ ID NO: 82)
```

Light chain of hzMWTx-003Var:
Protein sequence (Constant region indicated by italics):
DIQMTQSPKSLSASVGDRVTITCRASQDVTTALAWYQQKPGQSPKLLIYWATTRHSGV
PSRFSGSGSGTDFTLTISSLQPEDFATYYCQQHYSTPYTFGQGTKLEIK*RTVAAPSVFIFPP*
*SDEQLKSGTASVVCLLNNFYPREAKVQWKVDNALQSGNSQESVTEQDSKDSTYSLSSTLTLSK*
*ADYEKHKVYACEVTHQGLSSPVTKSFNRGEC* (SEQ ID NO: 83)

```
Nucleotide sequence:
GACATCCAGATGACCCAGTCTCCAAAGTCTCTGTCCGCCTCCGTGGGCGACAGAGTGAC
CATCACCTGTAGAGCCTCTCAGGACGTGACCACCGCTCTGGCTTGGTATCAGCAGAAGC
CTGGCCAGTCTCCTAAGCTGCTGATCTACTGGGCCACCACCAGACACTCTGGCGTGCCC
TCTAGATTCTCCGGCTCTGGCTCTGGCACCGACTTTACCCTGACAATCTCCAGCCTGCAG
CCTGAGGACTTCGCCACCTACTACTGCCAGCAGCACTACAGCACCCCTTACACCTTTGG
CCAGGGCACCAAGCTGGAAATCAAGCGGACAGTGGCCGCTCCTTCCGTGTTCATCTTCC
CACCTTCCGACGAGCAGCTGAAGTCCGGCACAGCTTCTGTCGTGTGCCTGCTGAACAAC
TTCTACCCTCGGGAAGCCAAGGTGCAGTGGAAGGTGGACAATGCCCTGCAGTCCGGCA
ACTCCCAAGAGTCTGTGACCGAGCAGGACTCCAAGGACAGCACCTACAGCCTGTCCTCC
ACACTGACCCTGTCCAAGGCCGACTACGAGAAGCACAAGGTGTACGCCTGCGAAGTGA
CCCATCAGGGCCTGTCTAGCCCTGTGACCAAGTCTTTCAACCGGGGCGAGTGT (SEQ ID
NO: 84)
```

Dose-Dependent Effects of Anti-TMPRSS6 Antibodies on HAMP Promoter Activity

FIGS. 2A-2F show the results from using the HAMP-luciferase report assay described above to test MWTx-001, MWTx-002, MWTx-003 and their humanized variants hzMWTx-001Var, hzMWTx-002Var, hzMWTx-003Var, respectively, at the indicated concentrations. Each of MWTx-001 (FIG. 2A), MWTx-002 (FIG. 2B), MWTx-003

Figure 2E:
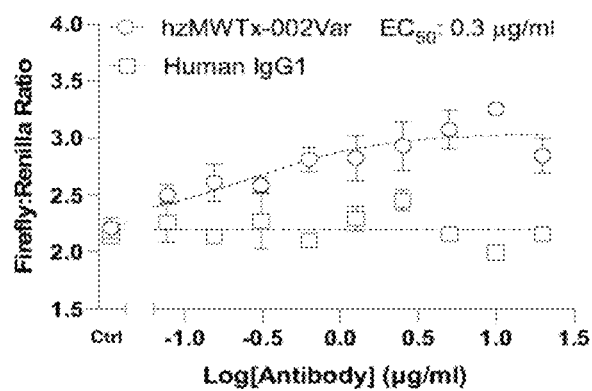
Figure 2F:
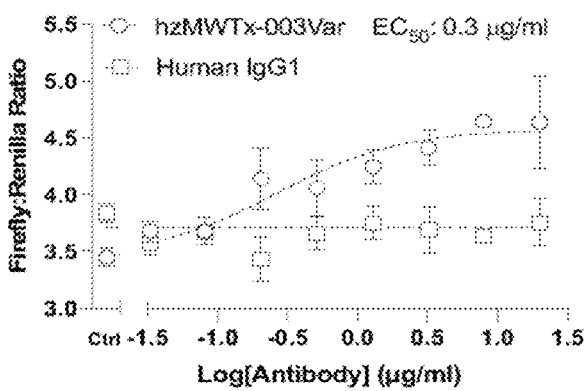

(FIG. 2C) and humanized variants hzMWTx-001Var (FIG. 2D), hzMWTx-002Var (FIG. 2E), hzMWTx-003Var (FIG. 2F) increases HAMP promoter activity in a dose-dependent manner. The $EC_{50}$ for MWTx-001 was calculated to be 3 µg/ml (FIG. 2A). The $EC_{50}$ for MWTx-002 was calculated to be 1 µg/ml (FIG. 2B). The $EC_{50}$ for MWTx-003 was calculated to be 2 µg/ml (FIG. 2C). The $EC_{50}$ for hzMWTx-001Var was calculated to be 0.8 µg/ml (FIG. 2D). The $EC_{50}$ for hzMWTx-002Var was calculated to be 0.3 µg/ml (FIG. 2E). The $EC_{50}$ for hzMWTx-003Var was calculated to be 0.3 µg/ml (FIG. 2F).

Example 3. Binding Affinity of Anti-TMPRSS6 Antibodies

The binding affinity of various anti-TMPRSS6 antibodies to human TMPRSS6 expressed on HEK293T cells was measured using three different methods: cell surface ELISA (FIGS. 3A-3C), FACS (FIGS. 3D-3F), and Bio-Layer Interferometry (FIGS. 3G-3M).

Anti-TMPRSS6 mAb Binding Affinity Measurement Using Cell Surface ELISA

Figure 3A:
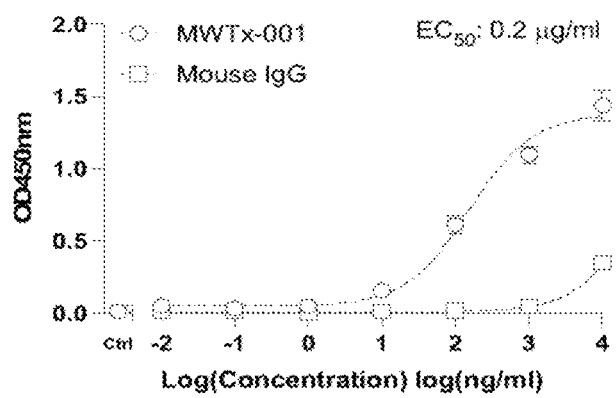
Figure 3B:
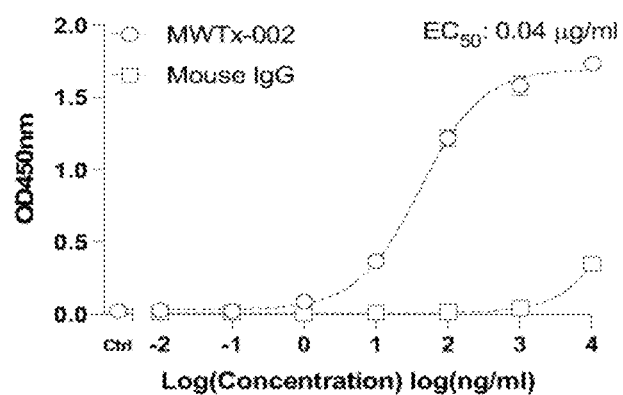
Figure 3C:
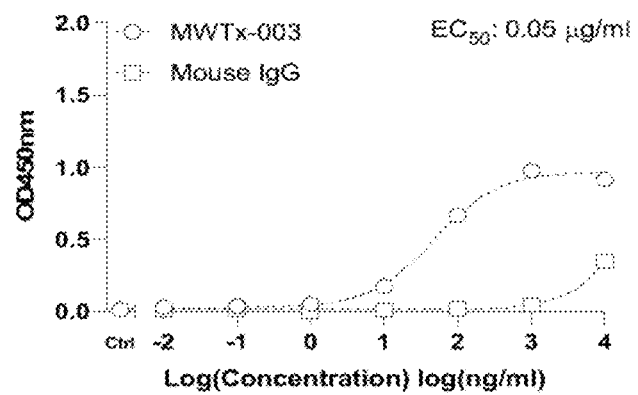

HEK293T cells stably expressing human TMPRSS6 (generated by LakePharma Inc as described above; SEQ ID NO: 97) were fixed with 4% paraformaldehyde (PFA), and washed with dPBS (Dulbecco's phosphate-buffered saline, Corning Cellgro) before incubation with various concentrations of anti-TMPRSS6 antibodies diluted in BSA medium (DMEM+1% Pen/Strep+10 mM HEPES+1 mg/ml BSA (Sigma-Aldrich). Purified mouse IgG was used as a control (Sigma-Aldrich). After incubation, cells were washed with BSA medium and then incubated with goat anti-mouse IgG conjugated with HRP as a 2° antibody (Invitrogen). At last, cells were washed with dPBS to remove unbound antibody and color developed with ELISA liquid substrate (Sigma-Aldrich), followed by stopping the reaction with addition of the same volume of ELISA liquid substrate of 1M H2SO4. Bound antibody was measured by absorbance at $OD_{450nm}$. Results for these assays are shown in FIGS. 3A-3C.

Anti-TMPRSS6 mAb Binding Affinity Measurement Using FACS

Figure 3D:
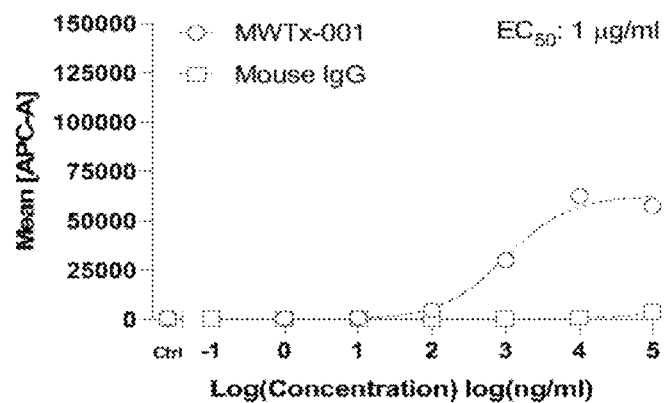
Figure 3E:
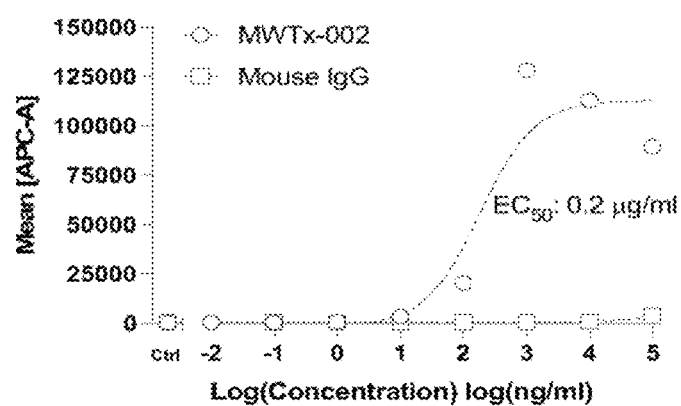
Figure 3F:
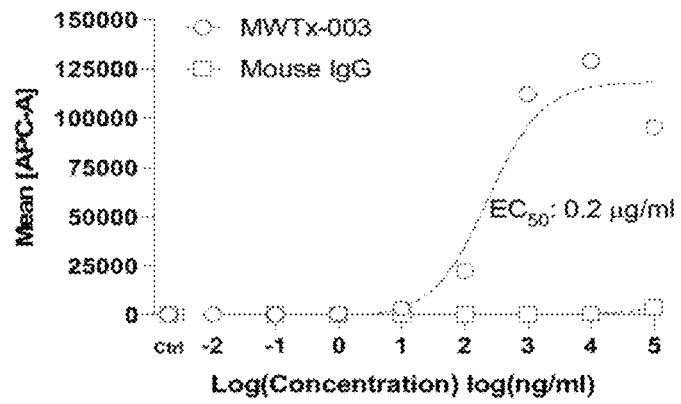
Figure 3G:
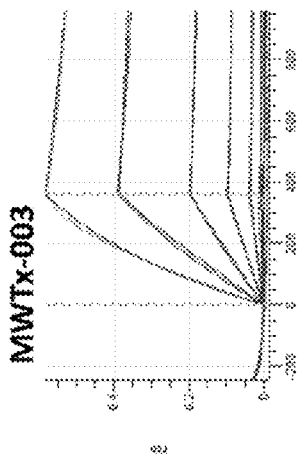
Figure 3H:
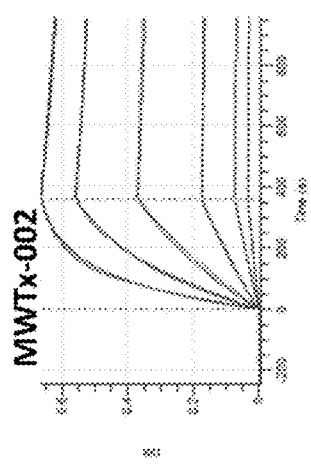
Figure 3I:
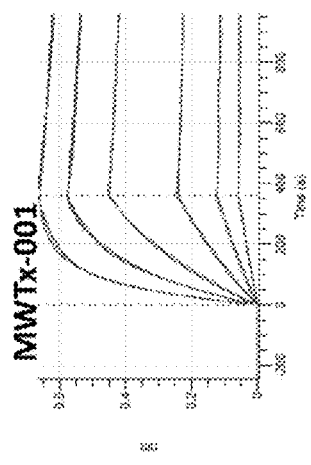
Figure 3J:
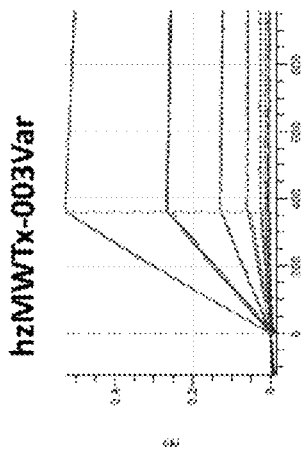
Figure 3K:
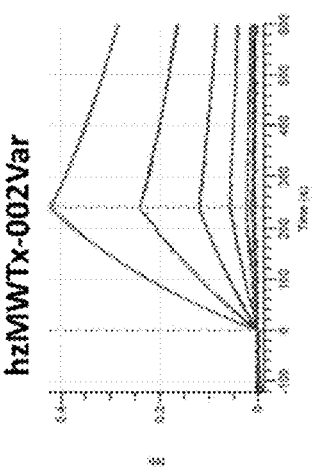
Figure 3L:
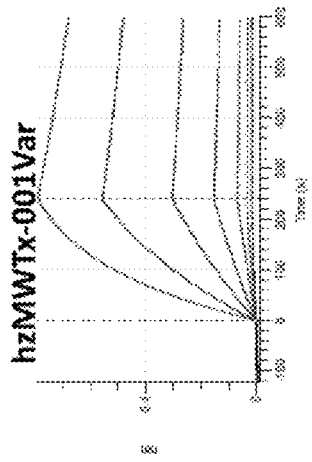

HEK293T cells stably expressing human TMPRSS6 were collected, and blocked with dPBS+3% BSA before incubation with various concentrations of anti-TMPRSS6 antibodies diluted in dPBS+3% BSA. Purified mouse IgG was used as a control. After incubation, cells were washed with dPBS and then incubated with goat anti-mouse IgG conjugated with APC as a 2° antibody (Jackson ImmunoResearch Inc). At last, cells were washed with dPBS to remove unbound antibody, re-suspended with dPBS+1 mM EDTA, and then subjected to FACS analysis using a NOVOCYTE® Flow Cytometer (ACEA Biosciences, Inc., San Diego CA). Bound antibody was determined by measuring mean APC intensity after excitation at 640 nm and measurement of emission (fluorescence) at 675 nm. Results for these assays are shown in FIGS. 3D-3F.

Anti-TMPRSS6 Antibody Affinity and Binding Kinetics Measurement Using Bio-Layer Interferometry Bio-Layer Interferometry technology was used for anti-TMPRSS6 antibody affinity measurement and binding kinetics determinations with Octet® RED96e system (Sartorius AG). Pre-hydrated Anti-Mouse IgG Fc Capture (AMC) biosensors (for MWTx-001, MWTx-002 and MWTx-003 anti-TMPRSS6 antibodies, FIGS. 3G-3I) or Anti-Human IgG Fc Capture (AHC) biosensors (for hzMWTx-001Var, hzMWTx-002Var and hzMWTx-003Var anti-TMPRSS6 antibodies, FIGS. 3J-3L) were first equilibrated in 1×KB (Kinetic Buffer, 1×PBS pH 7.4+0.02% Tween-20+0.1% BSA) for 120 sec for the first baseline, followed by loading with 10 mg/ml anti-TMPRSS6 antibody (MWTx-001, FIG. 3G; MWTx-002, FIG. 3H; MWTx-003, FIG. 3I; hzMWTx-001Var, FIG. 3J; hzMWTx-002Var, FIG. 3K; hzMWTx-003Var, FIG. 3L) onto AMC or AHC biosensors for 240 sec. Then, the second baseline signal was established for 120 sec before association with various concentrations of human ecto-TMPRSS6-FLAG (SEQ ID NO: 102) (generated in house by fusing extracellular domain of human TMPRSS6 with a FLAG-tag at C-terminus) for 240 sec. At last, analyte was dissociated in 1×KB for 360 sec. Data analysis was done using Octet Data Analysis H T Software. KD, $k_{on}$, $k_{off}$ and $R^2$ were summarized in FIG. 3M.

Example 4: Cross-Reactivity: Anti-TMPRSS6 Antibody Binding to Human TMPRSS6 and Non-Human TMPRSS6

Cross-Reactivity Determination by FACS

Selected anti-TMPRSS6 antibodies were tested to determine whether any are capable of binding to TMPRSS6 from mouse and/or cynomolgus monkey. HEK293T cells stably expressing human TMPRSS6 (HuTMPRSS6-(His)$_6$) (generated by LakePharma Inc as described above), HEK293T cells stably expressing mouse TMPRSS6 (MoTMPRSS6-(His)$_6$) (SEQ ID NO: 98) (generated by LakePharma Inc as described above) and HEK293T cells transiently expressing cynomolgus monkey TMPRSS6 (CynoTMPRSS6-(His)$_6$) (SEQ ID NO: 99) (generated in house) were collected. HEK293T cells stably expressing human TMPRSS6 were used as a positive control and HEK293T cells were used as a negative control (as described above). Cells were blocked with dPBS+3% BSA before incubation with anti-TMPRSS6 antibodies diluted in dPBS+3% BSA. After incubation, cells were washed with dPBS and followed by another incubation with goat anti-mouse IgG conjugated with AlexaFluor-488 as a 2° antibody (Invitrogen). At last, cells were washed with dPBS to remove unbound antibody, re-suspended with dPBS+1 mM EDTA, and then subjected to FACS analysis using a NOVOCYTE® Flow Cytometer (ACEA Biosciences, Inc., San Diego CA). Bound antibody was determined by excitation at 488 nm and measurement of emission (FITC-A) at 530 nm. Results for these assays are shown in histogram plots in FIGS. 4A-4I. Cross-reactivity with mouse TMPRSS6 was observed for MWTx-001 (FIG. 4D) and MWTx-003 (FIG. 4F), whereas MWTx-002 (FIG. 4E) did not show detectable cross-reactivity with mouse TMPRSS6. Cross-reactivity with cynomolgus monkey TMPRSS6 was observed for MWTx-001 (FIG. 4G), MWTx-002 (FIG. 4H) and MWTx-003 (FIG. 4I).

Cross-Reactivity Determination by Cell Surface ELISA

HEK293T cells stably expressing mouse TMPRSS6 (generated by LakePharma Inc as described above, FIGS. 4J, 4L, 4N, 4P, 4R, 4T) or cynomolgus monkey (generated in house as described above, FIGS. 4K, 4M, 4O, 4Q, 4S, 4U) were fixed with methanol (100%), and washed with dPBS (Dulbecco's phosphate-buffered saline, Corning Cellgro) before incubation with various concentrations of anti-TMPRSS6 antibodies and their humanized variants diluted in BSA medium (DMEM+1% Pen/Strep+10 mM HEPES+1 mg/ml BSA (Sigma-Aldrich)). Purified mouse IgG (FIGS. 4J-4O) or Human IgG1 (FIGS. 4P-4U) was used as a control. After incubation, cells were washed with BSA medium and then incubated with goat anti-mouse (Invitrogen, FIGS. 4J-4O) or anti-human (Millipore, FIGS. 4P-4U) IgG conjugated with HRP as a 2° antibody. Finally, cells were washed with dPBS to remove unbound antibody and color developed with ELISA liquid substrate (Sigma-Aldrich), followed by stopping the reaction with addition of the same volume of ELISA liquid substrate of 1M H2504. Bound antibody was measured by absorbance at $OD_{450nm}$. Results for these assays are shown in FIGS. 4J-4U. Cross-reactivity with mouse TMPRSS6 was observed for MWTx-001 (FIG. 4J) and MWTx-003 (FIG. 4N) anti-TMPRSS6 antibodies and their humanized variants hzMWTx-001Var (FIG. 4P), and hzMWTx-003Var (FIG. 4T) anti-TMPRSS6 antibodies, whereas MWTx-002 (FIG. 4L) anti-TMPRSS6 antibody or its humanized variant hzMWTx-002Var (FIG. 4R) anti-TMPRSS6 antibody did not show detectable cross-reactivity with mouse TMPRSS6. Cross-reactivity with cynomolgus monkey TMPRSS6 was observed for MWTx-001 (FIG. 4K), MWTx-002 (FIG. 4M), and MWTx-003 (FIG. 4O) anti-TMPRSS6 antibodies and their humanized variants hzMWTx-001Var (FIG. 4Q), hzMWTx-002Var (FIG. 4S), and hzMWTx-003Var (FIG. 4U) anti-TMPRSS6 antibodies.

Example 5: Target Specificity: Anti-TMPRSS6 Antibody Binding to Homologous Matriptases To determine if anti-TMPRSS6 antibodies bind to homologous matriptases, HEK293T cells over-expressing matriptase (ST14) (SEQ ID NO: 100) (FIGS. 5B, 5E, 5H, 5K, 5N, 5Q), and HEK293T cells over-expressing matriptase-3 (TMPRSS7) (SEQ ID NO: 101) (FIGS. 5C, 5F, 5I, 5L, 5O, 5R) were collected (generated in house). HEK293T cells stably expressing human TMPRSS6 (matriptase-2) (SEQ ID NO:97) (generated by LakePharma Inc as described above, FIGS. 5A, 5D, 5G, 5J, 5M, 5P) were used as a positive control and HEK293T cells (FIGS. 5A-5R) were used as a negative control (as described above). Cells were blocked and permeabilized with dPBS+ 3% BSA+0.1% Tween-20 before incubation with various anti-TMPRSS6 antibodies diluted in dPBS+3% BSA+0.1% Tween-20. Cells were incubated with anti-TMPRSS6 antibodies and their humanized variants at a concentration of roughly 1 µg/ml for 1 hr. After incubation, cells were washed with dPBS and incubated with goat anti-mouse IgG conjugated with AlexaFluor-488 (Invitrogen, FIGS. 5A-5I) or goat anti-human IgG conjugated with Allophycocyanin (APC) (Jackson Immuno Research, FIGS. 5J-5R) as a 2° antibody. At last, cells were washed with dPBS and re-suspended with dPBS+1 mM EDTA, and then subjected to FACS analysis using a NOVOCYTE® Flow Cytometer. Bound antibody was determined by excitation at 488 nm and measurement of emission (FITC-A) at 530 nm (FIGS. 5A-5I) or by excitation at 640 nm and measurement of emission (APC-A) at 675 nm (FIGS. 5J-5R). Results for these assays are shown in histogram plots in FIGS. 5A-5R. All of the antibodies showed binding to human TMPRSS6 (matriptase-2) (FIGS. 5A, 5D, 5G, 5J, 5M, 5P) and none of the antibodies showed binding to homologous matriptases ST14 (FIGS. 5B, 5E, 5H, 5K, 5N, 5Q) or TMPRSS7 (FIGS. 5C, 5F, 5I, 5L, 5O, 5R). MWTx-001 anti-TMPRSS6 antibody and its humanized variant hzMWTx-001Var anti-TMPRSS6 antibody showed binding to human TMPRSS6 (FIGS. 5A, 5J) and did not show binding to matriptase (ST14) (FIGS. 5B, 5K) or matriptase-3 (TMPRSS7) (FIGS. 5C, 5L). MWTx-002 anti-TMPRSS6 antibody and its humanized variant hzMWTx-002Var anti-TMPRSS6 antibody showed binding to human TMPRSS6 (matriptase-2) (FIGS. 5D, 5M) and did not show binding to matriptase (ST14) (FIGS. 5E, 5N) or matriptase-3 (TMPRSS7) (FIGS. 5F, 5O). MWTx-003 anti-TMPRSS6 antibody and its humanized variant hzMWTx-003Var anti-TMPRSS6 antibody showed binding to human TMPRSS6 (matriptase-2) (FIGS. 5G, 5P) and did not show binding to matriptase (ST14) (FIGS. 5H, 5Q) or matriptase-3 (TMPRSS7) (FIGS. 5I, 5R).

Example 6. Treatment with Anti-TMPRSS6 Antibodies in a Mouse Pharmacodynamic Model In order to study the in vivo pharmacodynamic responses of anti-TMPRSS6 antibodies, 2-10 mg/kg of MWTx-003 anti-TMPRSS6 antibody (FIGS. 6A-6B, 6D-6E, 6G-6H, 6J-6K) or its humanized variant hzMWTx-003Var anti-TMPRSS6 antibody (FIGS. 6C, 6F, 6I, 6L) was injected intraperitoneally into wildtype C57BL/6J mouse. Mouse IgG2b (BioXcell, FIGS. 6A-6B, 6D-6E, 6G-6H, 6J-6K) or human IgG1 (BioXcell, FIGS. 6C, 6F, 6I, 6L) was used as isotype control. 20 hours post injection, 50 µg of GFP-TMPRSS6 plasmid DNA (generated in house by inserting human TMPRSS6 into a GFP vector) was delivered into each mouse by hydrodynamic tail vein injection. 44 hours post hydrodynamic injection, mice were euthanized, liver tissues and blood were collected. Liver RNA was purified by EZgene Total RNA Purification Plus from Biomiga (San Diego, CA) according to the manufacturer's instructions. Mouse serum was obtained by centrifugation of whole blood at 1500×g, 10 min.

Effects of Treatment with Anti-TMPRSS6 Antibodies on Serum Iron

Serum iron was measured by a chromogenic assay developed in house (FIGS. 6A-6C). Briefly, mouse serum or iron standard (31-500 µg/dL) was mixed with Mixed Acid Solution (0.6M Trichloroacetic acid, 0.4M Thioglycolic sodium, 1M HCl) by vertexing for 30 sec. The mixtures were incubated for 10 min at 37° C. before centrifugation at 10,000×g for 10 min followed by color development in Color Solution (1.5M Sodium Acetate, 0.5 mM Bathophenanthroline disulfonic salt). The absorbance was then read at $OD_{535nm}$. The serum iron concentration was calculated from linear iron standard curve. Treatment of 10 mg/kg MWTx-003 anti-TMPRSS6 antibody (FIGS. 6A-6B) and its humanized variant hzMWTx-003Var anti-TMPRSS6 antibody (FIG. 6C) significantly reduced serum iron.

Effects of Treatment with Anti-TMPRSS6 Antibodies on Serum Hepcidin

Serum hepcidin was measured by Hepcidin-Murine Compete ELISA kit purchased from Intrinsic Lifesciences (La Jolla, CA) according to the manufacturer's instructions (FIGS. 6D-6F). Briefly, diluted mouse serum or hepcidin standard was mixed with hepcidin biotin conjugate before adding to the plate coated with an anti-murine hepcidin antibody. Serum hepcidin or hepcidin standard competes with hepcidin biotin conjugate for binding to coated anti-hepcidin antibody. The bound hepcidin biotin conjugate was detected with streptavidin conjugated horseradish peroxidase (HRP), and color developed with TMB followed by stop solution. The absorbance was then read at $OD_{450nm}$. The data was analyzed with Graphpad Prism 8 using a four-parameter logistic (4-PL) curve-fit, and serum hepcidin concentration was interpolated. Hydrodynamic delivery of GFP-TMPRSS6 significantly reduced serum hepcidin level (FIG. 6D), whereas treatment with 10 mg/kg MWTx-003 anti-TMPRSS6 antibody (FIGS. 6D-6E) and its humanized variant hzMWTx-003Var anti-TMPRSS6 antibody (FIG. 6F) reversed the repression of hepcidin and significantly increased serum hepcidin level.

Effects of Treatment with Anti-TMPRSS6 Antibodies on Liver Hepcidin RNA

Liver hepcidin RNA was quantified by real-time qPCR (FIGS. 6G-6I). Briefly, cDNA was first synthesized from liver RNA using iScript Reverse Transcription Supermix (Bio-Rad) according to the manufacturer's instructions. Hepcidin transcripts were amplified with specific primers listed below in Table 4, and detected using SsoAdvanced™ Universal SYBR® Green Supermix (Bio-Rad) according to the manufacturer's instructions on Bio-Rad CFX96 qPCR instrument. Samples were analyzed in triplicate, and results are normalized to β-actin RNA levels (measured by transcription, amplification with primers listed in Table 4, and quantification as described above). Hydrodynamic delivery of GFP-TMPRSS6 significantly reduced liver hepcidin RNA (FIG. 6G). Treatment of 10 mg/kg MWTx-003 anti-TMPRSS6 antibody (FIGS. 6G-6H) and its humanized variant hzMWTx-003Var anti-TMPRSS6 antibody (FIG. 6I) reversed the repression of Hamp and significantly increased liver hepcidin RNA levels. The following primers were used for RNA quantification by real-time qPCR: Hepcidin forward primer: 5'-AAG CAG GGC AGA CAT TGC GAT-3' (SEQ ID NO: 85); Hepcidin reverse primer: 5'-CAG GAT GTG GCT CTA GGC TAT-3' (SEQ ID NO: 86); β-actin forward primer: 5'-ACC CAC ACT GTG CCC ATC TA-3' (SEQ ID NO: 87); β-actin reverse primer: 5'-CAC GCT CGG TCA GGA TCT TC-3' (SEQ ID NO: 88).

Serum concentration of MWTx-003 anti-TMPRSS6 antibody or its humanized variant hzMWTx-003Var anti-TMPRSS6 antibody was quantified by cell surface ELISA developed in house (as described above, FIG. 6J-6L). Briefly, diluted mouse serum or anti-TMPRSS6 antibody standard were incubated with 100% methanol fixed HEK293T cells stably expressing human TMPRSS6 (HEK293T cells were used as background control). Bound MWTx-003 anti-TMPRSS6 antibody was detected with goat anti-mouse IgG conjugated with HRP, and bound hzMWTx-003Var anti-TMPRSS6 antibody was detected with goat anti-human IgG conjugated with HRP. Color was developed with TMB followed by stop solution. The absorbance was then read at $OD_{450nm}$. Samples were analyzed in triplicate, and results are normalized to HEK293T control. The data was analyzed with Graphpad Prism 8 using a four-parameter logistic (4-PL) curve-fit, and serum anti-TMPRSS6 antibody concentration was interpolated.

Example 7. In Vivo Efficacy of Anti-TMPRSS6 Antibody Using Beta-Thalassemia Mouse Model In order to study in vivo efficacy of anti-TMPRSS6 antibody, a β-thalassemia mouse model (B6.129P2-Hbb-b1$^{tm1Unc}$ Hbb_b2$^{tm1Unc}$/J, JAX Stock No: 002683, The Jackson Laboratories, Bar Harbor ME) was chosen, herein referred to as Th3/+ mouse. 4-5 weeks old Th3/+ mice and their wildtype (WT) littermates were put on an iron sufficient diet (Teklad TD.80394) and Th3/+ mice were treated with 10 mg/kg MWTx-003 anti-TMPRSS6 antibody or mouse IgG2b isotype control every three days for 4 weeks, while WT littermates did not receive treatments. At the end of the treatment course, mice were euthanized, and spleen, liver, femur and blood samples were collected. Liver total RNA was purified, and serum was collected as described above.
Effects on Blood Counts, Splenomegaly, Serum Iron, Serum Hepcidin, Liver Hepcidin RNA Complete Blood Count (CBC) was performed by VETSCAN HM5 automated hematology analyzer (FIGS. 7A-7D). MWTx-003 anti-TMPRSS6 antibody treatment significantly increased Red Blood Count (RBC, FIG. 7A) and hematocrit (HCT, FIG. 7C), and reduced Red Cell Distribution Width (RDW, FIG. 7D), but had no apparent effect on Hemoglobin (HGB, FIG. 7B) in Th3/+ mice.

Figure 7A:
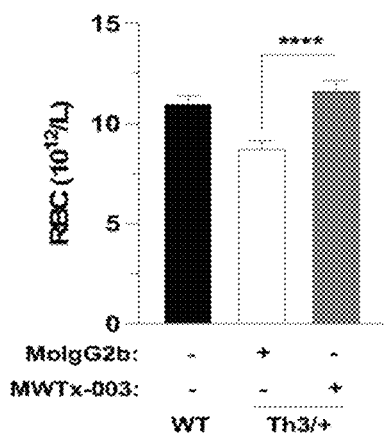
FIGS. 7A-7R show in vivo efficacy of anti-TMPRSS6 antibody using a β-thalassemia mouse model.
Figure 7B:
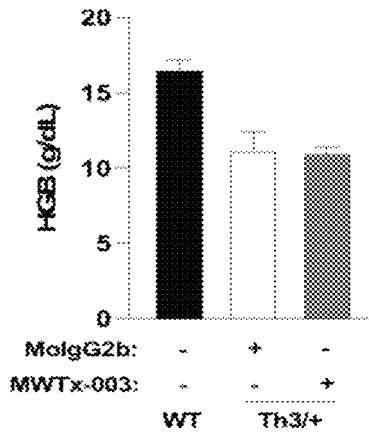
Figure 7C:
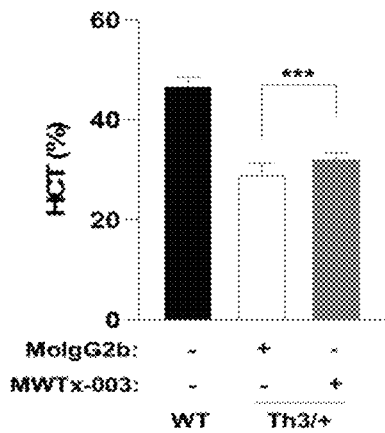
Figure 7D:
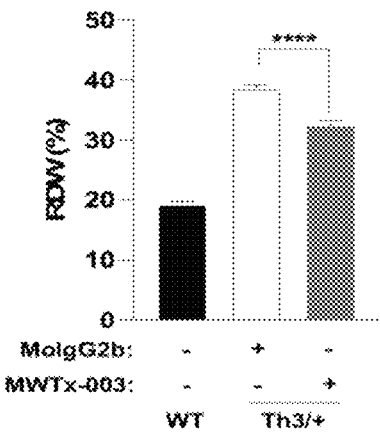
Figure 7E:
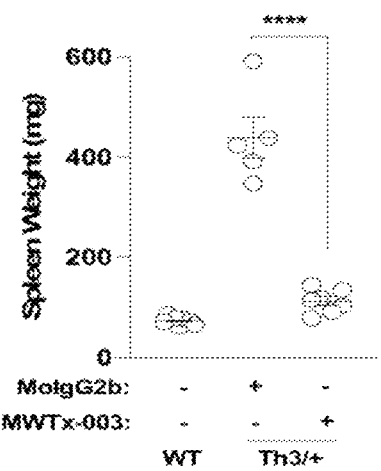
FIG. 7E shows effect of MWTx-003 anti-TMPRSS6 antibody on spleen weight using Th3/+ mice.

Spleen weight was measured, and MWTx-003 anti-TMPRSS6 antibody treatment significantly reduced splenomegaly for Th3/+ mice (FIG. 7E).

Serum iron was measured as described above. Treatment with MWTx-003 anti-TMPRSS6 antibody significantly reduced serum iron (FIG. 7F). Liver non-heme iron was measured using a similar chromogenic assay (FIG. 7G). Briefly, minced small liver tissue was dried at 65° C. for overnight followed by digestion with mixed acid (3M HCl, 10% Trichloroacetic acid) at 65° C. for 20 hr. Then, digestion supernatant was collected for color development in Color Solution (1.5M sodium acetate, 0.5 mM bathophenanthroline disulfonic salt). The absorbance was then read at $OD_{535nm}$. Treatment with MWTx-003 anti-TMPRSS6 antibody significantly reduced liver non-heme iron (FIG. 7G).

Serum hepcidin was measured by Hepcidin-Murine Compete ELISA kit as described above. Treatment with MWTx-003 anti-TMPRSS6 antibody significantly increased serum hepcidin (FIG. 7H).

Liver hepcidin RNA was quantified by real-time qPCR as described above. Treatment with MWTx-003 anti-TMPRSS6 antibody significantly increased liver hepcidin RNA (FIG. 7I).

Serum concentration of MWTx-003 anti-TMPRSS6 antibody was quantified by cell surface ELISA developed in-house as described above (FIG. 7J).
Effects on Erythropoiesis In order to study effects of MWTx-003 anti-TMPRSS6 antibody on erythropoiesis in Th3/+ mice, bone marrow was harvested from femur (see FIGS. 7K-7M) and splenocytes were harvested from spleen (see FIGS. 7N-7P), and analyzed. Harvested cells were blocked with rat anti-mouse CD16/CD32 (BD Biosciences) for 15 min followed by staining with rat anti-mouse TER119 conjugated with FITC (BD Biosciences) and rat anti-mouse CD44 conjugated with APC (Invitrogen) for 30 min on ice. Washed cells were stained with the viability marker 7-AAD (BD Biosciences) for 10 min on ice before FACS analysis using a NOVOCYTE® Flow Cytometer. Ter119$^+$, 7-ADD$^-$ cells were selected, and density plots were graphed with anti-mouse CD44 over cell size (FSC-H). Plots were analyzed to identify cell types (cell clusters) and determine the abundance of each type (cluster) Representative plots in FIGS. 7K-7P show that four distinct cell clusters were distinguished from top to bottom, corresponding to successive stages in erythroid differentiation and identified as: basophilic erythroblasts (cluster I), polychromatic erythroblasts (cluster II), orthochromatic erythroblasts and nonnucleated reticulocytes (cluster III) and mature red cells (cluster IV). Percentage (%) value of each cluster in a sample was calculated as a measure of the abundance of cell type(s) in that cluster, as shown in FIGS. 7K-7P. The % value for each cell cluster (I), (II), (III), (IV) was calculated for each sample (bone marrow, spleen) from each animal in each treatment course, as follows: WT (no treatment) N=9; disease model Th3/+ mouse treated with IgG2b isotype control (Th3+ w/MoIgG2b), N=5; disease model Th3/+ mouse treated with MWTx-003 anti-TMPRSS6 antibody (Th3+ w/MWTx-003), N=7 and average values were then calculated. On average, populations of basophilic erythroblasts (I) showed a 7.58% (Th3+ w/MoIgG2b) to 6.52% (Th3+ w/MWTx-003) shift (7.96% for WT), polychromatic erythroblasts (II) showed a 54.20%

Figure 7Q:
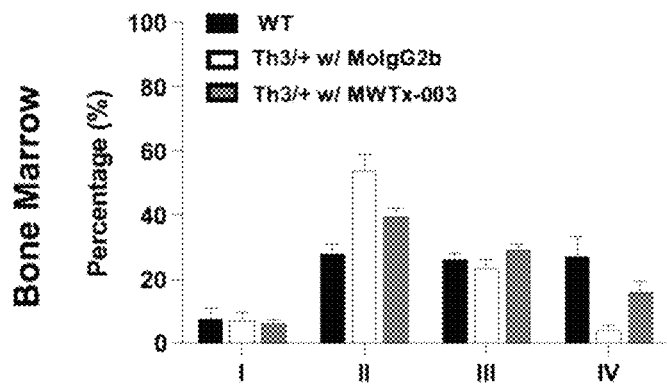
Figure 7R:
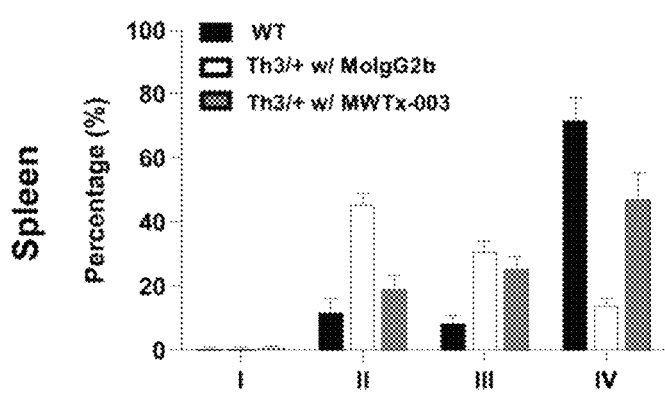

(Th3+ w/MoIgG2b) to 40.01% (Th3+ w/MWTx-003) shift (28.53% for WT), orthochromatic erythroblasts and non-nucleated reticulocytes (III) showed a 24.06% (Th3+ w/MoIgG2b) to 29.73% (Th3+ w/MWTx-003) shift (26.67% for WT) and mature red cells (IV) showed a 4.54% (Th3+ w/MoIgG2b) to 16.44% shift (27.66% for WT) in bone marrow cells after four weeks. On average, populations of basophilic erythroblasts (I) showed a 0.71% (Th3+ w/MoIgG2b) to 0.91% (Th3+ w/MWTx-003) shift (0.46% for WT), polychromatic erythroblasts (II) showed a 45.76% (Th3+ w/MoIgG2b) to 19.25% (Th3+ w/MWTx-003) shift (12.23% for WT), orthochromatic erythroblasts and non-nucleated reticulocytes (III) showed a 31.16% (Th3+ w/MoIgG2b) to 28.72% (Th3+ w/MWTx-003) shift (8.67% for WT) and a mature red cells (IV) showed a 14.13% (Th3+ w/MoIgG2b) to 44.38% (Th3+ w/MWTx-003) shift (72.17% for WT) in spleen after found weeks. These results are shown in a bar graph in FIG. 7Q for bone marrow, and FIG. 7R for spleen.

In Th3/+ mice, treatment with MWTx-003 anti-TM-PRSS6 antibody improved ineffective erythropoiesis, with a significant proportion of erythroblasts differentiated and matured into red blood cells.

Example 8. Anti-TMPRSS6 Antibodies Epitope Binning

OCTET® RED96e was used for epitope binning of MWTx-001 (FIG. 8A), MWTx-002 (FIG. 8B) and MWTx-003 (FIG. 8C) anti-TMPRSS6 antibodies. First, ecto-TM-PRSS6-FLAG (as described above) was labelled with biotin by Biotinylation Kit (Abcam). Pre-hydrated streptavidin (SA) biosensors were equilibrated in 1×KB (as described above) for 60 sec for the first baseline, followed by loading with 10 mg/ml of biotinylated ecto-TMPRSS6-FLAG onto the SA biosensors for 300 sec. Then, the second baseline signal was established for 60 sec before saturation with 50 mg/ml of antibody (MWTx-001, FIG. 8A; MWTx-002, FIG. 8B; MWTx-003, FIG. 8C) in 1×KB for 600 sec. At last, the third baseline signal was established for 60 sec before competition with 50 μg/ml of MWTx-001, MWTx-002 or MWTx-003 in 1×KB for 300 sec. MWTx-001 anti-TM-PRSS6 antibody binding towards ecto-TMPRSS6-FLAG was not competed with MWTx-002 anti-TMPRSS6 antibody or MWTx-003 anti-TMPRSS6 antibody (FIG. 8A). MWTx-002 anti-TMPRSS6 antibody binding towards ecto-TMPRSS6-FLAG was not competed with MWTx-001 anti-TMPRSS6 antibody but was competed with MWTx-003 anti-TMPRSS6 antibody (FIG. 8B). MWTx-003 anti-TM-PRSS6 antibody binding towards ecto-TMPRSS6-FLAG was not competed with MWTx-001 anti-TMPRSS6 antibody but was competed with MWTx-002 anti-TMPRSS6 antibody (FIG. 8C). Data analysis was done using Octet Data Analysis HT Software. Association signals were summarized in FIG. 8D.

```
                               SEQUENCE LISTING

Sequence total quantity: 102
SEQ ID NO: 1              moltype = AA  length = 118
FEATURE                   Location/Qualifiers
source                    1..118
                          mol_type = protein
                          organism = Mus musculus
SEQUENCE: 1
QVQLQQPGAE LAKPGASVKM SCKASGYTFT SYWITWVKQR PGQDLEWIGN IYPGSGSTYY   60
NEKFKSKATL TVDTSSRTAY MQLSSLTSAD SAVYYCAPYD SDYAMDYWGQ GTSVTVSS    118

SEQ ID NO: 2              moltype = AA  length = 8
FEATURE                   Location/Qualifiers
source                    1..8
                          mol_type = protein
                          organism = Mus musculus
SEQUENCE: 2
GYTFTSYW                                                            8

SEQ ID NO: 3              moltype = AA  length = 8
FEATURE                   Location/Qualifiers
source                    1..8
                          mol_type = protein
                          organism = Mus musculus
SEQUENCE: 3
IYPGSGST                                                            8

SEQ ID NO: 4              moltype = AA  length = 11
FEATURE                   Location/Qualifiers
source                    1..11
                          mol_type = protein
                          organism = Mus musculus
SEQUENCE: 4
APYDSDYAMD Y                                                        11

SEQ ID NO: 5              moltype = DNA  length = 354
FEATURE                   Location/Qualifiers
source                    1..354
                          mol_type = other DNA
                          organism = Mus musculus
```

```
SEQUENCE: 5
caggtccaac tgcagcagcc tggggctgag cttgcgaagc ctggggcttc agtgaagatg    60
tcctgcaagg cttctggcta caccttcacc agctactgga taacctgggt gaagcagagg   120
cctggacaag accttgagtg gattggaaat atttatcctg gtagtggtag tacttactac   180
aatgagaagt tcaagagcaa ggccacactg actgtagaca catcctccag aacagcctac   240
atgcagctca gcagtctgac atctgcggac tctgcggtct attactgtgc ccctatgat    300
tccgactatg ctatggacta ctggggtcaa ggaacctcag tcaccgtctc ctca          354

SEQ ID NO: 6           moltype = AA  length = 107
FEATURE                Location/Qualifiers
source                 1..107
                       mol_type = protein
                       organism = Mus musculus
SEQUENCE: 6
DIKMTQSPSS MYASLGERVT ITCKASQDIN NYLSWFQQKP GKSPKTLIYR ANRLVDGVPS    60
RVSGSGSGQD YSLTISSLEY EDVGIYFCLQ YDEFPLTFGA GTKLELK                 107

SEQ ID NO: 7           moltype = AA  length = 6
FEATURE                Location/Qualifiers
source                 1..6
                       mol_type = protein
                       organism = Mus musculus
SEQUENCE: 7
QDINNY                                                                 6

SEQ ID NO: 8           moltype =  length =
SEQUENCE: 8
000

SEQ ID NO: 9           moltype = AA  length = 9
FEATURE                Location/Qualifiers
source                 1..9
                       mol_type = protein
                       organism = Mus musculus
SEQUENCE: 9
LQYDEFPLT                                                              9

SEQ ID NO: 10          moltype = DNA  length = 321
FEATURE                Location/Qualifiers
source                 1..321
                       mol_type = other DNA
                       organism = Mus musculus
SEQUENCE: 10
gacatcaaga tgacccagtc tccatcttcc atgtatgcat ctctaggaga gagagtcact    60
atcacttgca aggcgagtca ggacattaat aactatttaa gctggttcca gcagaaacca   120
gggaaatctc ctaagaccct gatctatcgt gcaaacagat tggtagatgg ggtcccatca   180
agggtcagtg gcagtggatc tgggcaagat tattctctca ccatcagcag cctggagtat   240
gaagatgtgg gaatttattt ttgtctacag tatgatgagt ttcctctcac gttcggtgct   300
gggaccaagc tggagctgaa a                                              321

SEQ ID NO: 11          moltype = AA  length = 121
FEATURE                Location/Qualifiers
source                 1..121
                       mol_type = protein
                       organism = Mus musculus
SEQUENCE: 11
EVQLQQSGAE LVKPGASVKL SCTASGFNIK DYYIHWVKER TEQGLEWFGR IDPEDGESEY    60
APKFQGKATL TADTSSNTAY LQLSSLTSED TAVYYCTRGD SMMVTYFDYW GQGTTLTVSS   120
E                                                                    121

SEQ ID NO: 12          moltype = AA  length = 8
FEATURE                Location/Qualifiers
source                 1..8
                       mol_type = protein
                       organism = Mus musculus
SEQUENCE: 12
GFNIKDYY                                                               8

SEQ ID NO: 13          moltype = AA  length = 8
FEATURE                Location/Qualifiers
source                 1..8
                       mol_type = protein
                       organism = Mus musculus
```

```
SEQUENCE: 13
IDPEDGES                                                                        8

SEQ ID NO: 14           moltype = AA  length = 13
FEATURE                 Location/Qualifiers
source                  1..13
                        mol_type = protein
                        organism = Mus musculus
SEQUENCE: 14
TRGDSMMVTY FDY                                                                 13

SEQ ID NO: 15           moltype = DNA  length = 360
FEATURE                 Location/Qualifiers
source                  1..360
                        mol_type = other DNA
                        organism = Mus musculus
SEQUENCE: 15
gaggttcagc tgcagcagtc tggggcagaa cttgtgaagc caggggcctc agtcaagttg             60
tcctgcacag cctctggctt caacattaaa gactactata tacactgggt gaaagagagg            120
actgaacagg gcctggagtg gtttggaagg attgatcctg aggatggtga aagtgaatat            180
gccccgaaat tccagggcaa ggccacttta acagcagaca catcctccaa tacagcctac            240
ctgcagctca gcagcctgac atctgaggac actgccgtct attactgtac tagaggagac            300
tctatgatgg ttacctactt tgactactgg ggccaaggca ccactctcac ggtctcctca            360

SEQ ID NO: 16           moltype = AA  length = 107
FEATURE                 Location/Qualifiers
source                  1..107
                        mol_type = protein
                        organism = Mus musculus
SEQUENCE: 16
DIVMTQSHKF MSTSVGDRVS ITCKASQDVS TAVAWYQQKP GQSPKLLIYW AFTRHTGVPD             60
RFTSTGSGTD YALTISSVQA EDLALYYCQQ HYRSPWTFGG GTKLEIK                          107

SEQ ID NO: 17           moltype = AA  length = 6
FEATURE                 Location/Qualifiers
source                  1..6
                        mol_type = protein
                        organism = Mus musculus
SEQUENCE: 17
QDVSTA                                                                         6

SEQ ID NO: 18           moltype =   length =
SEQUENCE: 18
000

SEQ ID NO: 19           moltype = AA  length = 9
FEATURE                 Location/Qualifiers
source                  1..9
                        mol_type = protein
                        organism = Mus musculus
SEQUENCE: 19
QQHYRSPWT                                                                      9

SEQ ID NO: 20           moltype = DNA  length = 321
FEATURE                 Location/Qualifiers
source                  1..321
                        mol_type = other DNA
                        organism = Mus musculus
SEQUENCE: 20
gacattgtga tgacccagtc tcacaaattc atgtccacat cagtaggaga cagggtcagc             60
atcacctgca aggccagtca ggatgtgagt actgctgtag cctggtatca acaaaaacca            120
gggcaatctc ctaaactact gatttactgg gctttcaccc gtcacactgg agtccctgat            180
cgcttcacaa gcactggatc tgggacagat tatgctctca ccatcagcag tgtgcaggct            240
gaagacctgg cactttatta ctgtcagcaa cattatcgca gtccgtggac gttcggtgga            300
ggcaccaaac tggaaatcaa a                                                      321

SEQ ID NO: 21           moltype = AA  length = 118
FEATURE                 Location/Qualifiers
source                  1..118
                        mol_type = protein
                        organism = Mus musculus
SEQUENCE: 21
EVQLQQSGAE LVKPGASVKL SCTASGFNIE DYYIHWVKER TEQGLEWIGR IDPEDGETTY             60
APQFQGKATI IPDTSSNTAY MQLSSLTSED AAVYYCARSI YLDPMDYWGQ GTSVTVSS              118
```

| SEQ ID NO: 22 | moltype = AA length = 8 |
| --- | --- |
| FEATURE | Location/Qualifiers |
| source | 1..8 |
| | mol_type = protein |
| | organism = Mus musculus |

SEQUENCE: 22
GFNIEDYY                                                                        8

| SEQ ID NO: 23 | moltype = AA length = 8 |
| --- | --- |
| FEATURE | Location/Qualifiers |
| source | 1..8 |
| | mol_type = protein |
| | organism = Mus musculus |

SEQUENCE: 23
IDPEDGET                                                                        8

| SEQ ID NO: 24 | moltype = AA length = 11 |
| --- | --- |
| FEATURE | Location/Qualifiers |
| source | 1..11 |
| | mol_type = protein |
| | organism = Mus musculus |

SEQUENCE: 24
ARSIYLDPMD Y                                                                   11

| SEQ ID NO: 25 | moltype = DNA length = 354 |
| --- | --- |
| FEATURE | Location/Qualifiers |
| source | 1..354 |
| | mol_type = other DNA |
| | organism = Mus musculus |

SEQUENCE: 25
```
gaagttcagc tgcagcagtc tggggcagaa cttgtgaagc caggggcctc agtcaagttg    60
tcctgcacag cttctggctt caacattgaa gactactata tacactgggt gaaggagagg   120
actgaacagg gcctggagtg gattggaagg attgatcctg aggatggtga aactacatat   180
gccccgcagt tccagggcaa ggccactata ataccagaca catcctccaa cacagcctac   240
atgcagctca gcagcctgac atctgaggac gctgccgtct attactgtgc tagatcgatc   300
taccttgatc ctatggacta ctggggtcaa ggaacctcag tcaccgtctc ctca          354
```

| SEQ ID NO: 26 | moltype = AA length = 107 |
| --- | --- |
| FEATURE | Location/Qualifiers |
| source | 1..107 |
| | mol_type = protein |
| | organism = Mus musculus |

SEQUENCE: 26
```
DIVMTQSHKF MSTSVGDRVS ITCKASQDVT TAVAWYQQKP GQSPKILIYW ATTRHTGVPD    60
RFTGSISGTT YILTISSVQA EDLALYYCQQ HYSTPYTFGG GTKLEIK                 107
```

| SEQ ID NO: 27 | moltype = AA length = 6 |
| --- | --- |
| FEATURE | Location/Qualifiers |
| source | 1..6 |
| | mol_type = protein |
| | organism = Mus musculus |

SEQUENCE: 27
QDVTTA                                                                          6

| SEQ ID NO: 28 | moltype = length = |
| --- | --- |

SEQUENCE: 28
000

| SEQ ID NO: 29 | moltype = AA length = 9 |
| --- | --- |
| FEATURE | Location/Qualifiers |
| source | 1..9 |
| | mol_type = protein |
| | organism = Mus musculus |

SEQUENCE: 29
QQHYSTPYT                                                                       9

| SEQ ID NO: 30 | moltype = DNA length = 321 |
| --- | --- |
| FEATURE | Location/Qualifiers |
| source | 1..321 |
| | mol_type = other DNA |
| | organism = Mus musculus |

SEQUENCE: 30
```
gacattgtga tgacccagtc tcacaaattc atgtccacat cagtaggaga cagggtcagc    60
atcacctgca aggccagtca ggatgtgact actgctgtcg cctggtatca acaaaaacca   120
ggacagtctc ctaaaatact gatttactgg gcaaccaccc ggcacactgg agtccctgat   180
cgcttcacag gcagtatatc tgggacaact tatattctca ccatcagtag tgtgcaggct   240
gaagacctgg cactttatta ctgtcagcaa cattatagca ctccgtacac gttcggaggg   300
gggaccaagc tggaaataaa a                                              321
```

| SEQ ID NO: 31 | moltype = AA  length = 118 |
| --- | --- |
| FEATURE | Location/Qualifiers |
| REGION | 1..118 |
| | note = source = /note="Description of Artificial Sequence: Synthetic polypeptide" |
| source | 1..118 |
| | mol_type = protein |
| | organism = synthetic construct |

SEQUENCE: 31
```
EVQLVQSGAE VKKPGASVKV SCKASGYTFT SYWITWVRQA PGQRLEWIGN IYPGSGSTYY   60
NEKFKSKATI TRDTSSRTAY MELSSLRSED TAVYYCAPYD ADYAMDYWGQ GTLVTVSS   118
```

| SEQ ID NO: 32 | moltype = AA  length = 8 |
| --- | --- |
| FEATURE | Location/Qualifiers |
| REGION | 1..8 |
| | note = source = /note="Description of Artificial Sequence: Synthetic peptide" |
| source | 1..8 |
| | mol_type = protein |
| | organism = synthetic construct |

SEQUENCE: 32
```
GYTFTSYW                                                            8
```

| SEQ ID NO: 33 | moltype = AA  length = 8 |
| --- | --- |
| FEATURE | Location/Qualifiers |
| REGION | 1..8 |
| | note = source = /note="Description of Artificial Sequence: Synthetic peptide" |
| source | 1..8 |
| | mol_type = protein |
| | organism = synthetic construct |

SEQUENCE: 33
```
IYPGSGST                                                            8
```

| SEQ ID NO: 34 | moltype = AA  length = 11 |
| --- | --- |
| FEATURE | Location/Qualifiers |
| REGION | 1..11 |
| | note = source = /note="Description of Artificial Sequence: Synthetic peptide" |
| source | 1..11 |
| | mol_type = protein |
| | organism = synthetic construct |

SEQUENCE: 34
```
APYDADYAMD Y                                                       11
```

| SEQ ID NO: 35 | moltype = DNA  length = 354 |
| --- | --- |
| FEATURE | Location/Qualifiers |
| misc_feature | 1..354 |
| | note = source = /note="Description of Artificial Sequence: Synthetic polynucleotide" |
| source | 1..354 |
| | mol_type = other DNA |
| | organism = synthetic construct |

SEQUENCE: 35
```
gaagtgcagc tggtgcaatc tggcgccgaa gtgaagaaac ctggcgcctc tgtgaaggtg   60
tcctgcaagg cttccggcta cacctttacc agctactgga tcacctgggt ccgacaggct  120
cctggccaga gactggaatg gatcggcaac atctacctg gctccggctc cacctactac  180
aacgagaagt tcaagtccaa ggccacaatc acccgggaca cctcttccag aaccgctac   240
atggaactgt ccagcctgag atctgaggac accgccgtgt actactgcgc cccttacgac  300
gccgactacg ccatggatta ttggggccag ggcaccctgg tcaccgtgtc ctct        354
```

| SEQ ID NO: 36 | moltype = AA  length = 107 |
| --- | --- |
| FEATURE | Location/Qualifiers |
| REGION | 1..107 |
| | note = source = /note="Description of Artificial Sequence: Synthetic polypeptide" |
| source | 1..107 |
| | mol_type = protein |
| | organism = synthetic construct |

SEQUENCE: 36
```
DIQMTQSPSS LSASVGDRVT ITCKASQDIS NYLSWFQQKP GKAPKLLIYR ANRLVEGVPS   60
RFSGSGSGTD FTLTISSLQP EDFATYFCLQ YDEFPLTFGG GTKVEIK                107
```

| SEQ ID NO: 37 | moltype = AA  length = 6 |
| --- | --- |
| FEATURE | Location/Qualifiers |
| REGION | 1..6 |
| | note = source = /note="Description of Artificial Sequence: Synthetic peptide" |

```
source                    1..6
                          mol_type = protein
                          organism = synthetic construct
SEQUENCE: 37
QDISNY                                                                    6

SEQ ID NO: 38             moltype =   length =
SEQUENCE: 38
000

SEQ ID NO: 39             moltype = AA   length = 9
FEATURE                   Location/Qualifiers
REGION                    1..9
                          note = source = /note="Description of Artificial Sequence:
                          Synthetic peptide"
source                    1..9
                          mol_type = protein
                          organism = synthetic construct
SEQUENCE: 39
LQYDEFPLT                                                                 9

SEQ ID NO: 40             moltype = DNA   length = 321
FEATURE                   Location/Qualifiers
misc_feature              1..321
                          note = source = /note="Description of Artificial Sequence:
                          Synthetic polynucleotide"
source                    1..321
                          mol_type = other DNA
                          organism = synthetic construct
SEQUENCE: 40
gacatccaga tgacccagtc tccatcctct ctgtccgcct ctgtgggcga cagagtgacc    60
atcacatgca aggccagcca ggacatctcc aactacctgt cctggttcca gcagaagcct   120
ggcaaggctc ccaagctgct gatctacaga gccaacagac tggtggaagg cgtgccctcc   180
agattctccg gatctggctc tggcaccgac tttaccctga caatctccag cctgcagcct   240
gaggacttcg ctacctactt ctgcctgcaa tacgacgagt ccctctctga cttttggcgga   300
ggcaccaagg tggaaatcaa g                                              321

SEQ ID NO: 41             moltype = AA   length = 120
FEATURE                   Location/Qualifiers
REGION                    1..120
                          note = source = /note="Description of Artificial Sequence:
                          Synthetic polypeptide"
source                    1..120
                          mol_type = protein
                          organism = synthetic construct
SEQUENCE: 41
EVQLVQSGAE VKKPGASVKV SCKASGFNIK DYYIHWVRQA TGQGLEWMGR IDPEDAESEY     60
APKFQGRVTI TADTSTDTAY MELSSLRSED TAVYYCTRGD SMMVTYFDYW GQGTLVTVSS    120

SEQ ID NO: 42             moltype = AA   length = 8
FEATURE                   Location/Qualifiers
REGION                    1..8
                          note = source = /note="Description of Artificial Sequence:
                          Synthetic peptide"
source                    1..8
                          mol_type = protein
                          organism = synthetic construct
SEQUENCE: 42
GFNIKDYY                                                                  8

SEQ ID NO: 43             moltype = AA   length = 8
FEATURE                   Location/Qualifiers
REGION                    1..8
                          note = source = /note="Description of Artificial Sequence:
                          Synthetic peptide"
source                    1..8
                          mol_type = protein
                          organism = synthetic construct
SEQUENCE: 43
IDPEDAES                                                                  8

SEQ ID NO: 44             moltype = AA   length = 13
FEATURE                   Location/Qualifiers
REGION                    1..13
                          note = source = /note="Description of Artificial Sequence:
                          Synthetic peptide"
source                    1..13
                          mol_type = protein
                          organism = synthetic construct
```

```
SEQUENCE: 44
TRGDSMMVTY FDY                                                      13

SEQ ID NO: 45           moltype = DNA  length = 360
FEATURE                 Location/Qualifiers
misc_feature            1..360
                        note = source = /note="Description of Artificial Sequence:
                        Synthetic polynucleotide"
source                  1..360
                        mol_type = other DNA
                        organism = synthetic construct
SEQUENCE: 45
gaagtgcagc tggtgcaatc tggcgccgaa gtgaagaaac ctggcgcctc tgtgaaggtg   60
tcctgcaagg cctctggctt caacatcaag gactactaca tccactgggt ccgacaggct  120
accggacagg gacttgagtg gatgggcaga atcgaccctg aggacgccga gtctgagtac  180
gcccctaagt ttcagggcag agtgaccatc accgccgaca cctctaccga caccgcctac  240
atgaactgt  ccagcctgag atctgaggac accgccgtgt actactgcac cagaggcgac  300
tccatgatgg ttacctactt cgactactgg ggccagggca ccctggtcac agtttcttcc  360

SEQ ID NO: 46           moltype = AA  length = 107
FEATURE                 Location/Qualifiers
REGION                  1..107
                        note = source = /note="Description of Artificial Sequence:
                        Synthetic polypeptide"
source                  1..107
                        mol_type = protein
                        organism = synthetic construct
SEQUENCE: 46
DIQMTQSPSS LSASVGDRVT ITCKASQDVS TAVAWYQQKP GKAPKLLIYW AFTRHTGVPS   60
RFSGSGSGTD YALTISSLQP EDFATYYCQQ HYRSPWTFGG GTKVEIK                107

SEQ ID NO: 47           moltype = AA  length = 6
FEATURE                 Location/Qualifiers
REGION                  1..6
                        note = source = /note="Description of Artificial Sequence:
                        Synthetic peptide"
source                  1..6
                        mol_type = protein
                        organism = synthetic construct
SEQUENCE: 47
QDVSTA                                                               6

SEQ ID NO: 48           moltype =      length =
SEQUENCE: 48
000

SEQ ID NO: 49           moltype = AA  length = 9
FEATURE                 Location/Qualifiers
REGION                  1..9
                        note = source = /note="Description of Artificial Sequence:
                        Synthetic peptide"
source                  1..9
                        mol_type = protein
                        organism = synthetic construct
SEQUENCE: 49
QQHYRSPWT                                                            9

SEQ ID NO: 50           moltype = DNA  length = 321
FEATURE                 Location/Qualifiers
misc_feature            1..321
                        note = source = /note="Description of Artificial Sequence:
                        Synthetic polynucleotide"
source                  1..321
                        mol_type = other DNA
                        organism = synthetic construct
SEQUENCE: 50
gacatccaga tgacccagtc tccatcctct ctgtccgcct ctgtgggcga cagagtgacc   60
atcacatgca aggcctctca ggacgtgtcc accgccgttg cttggtatca gcagaagcct  120
ggcaaggccc ctaagctgct gatctactgg gccttcacca gacacaccgg cgtgccctct  180
aggttctccg gctctggctc tggcaccgat tacgctctga caatctccag cctgcagcct  240
gaggacttcg ccacctacta ctgccagcag cactacagaa gcccctggac atttggcgga  300
ggcaccaagg tggaaatcaa g                                            321

SEQ ID NO: 51           moltype = AA  length = 118
FEATURE                 Location/Qualifiers
REGION                  1..118
                        note = source = /note="Description of Artificial Sequence:
                        Synthetic polypeptide"
```

```
source                  1..118
                        mol_type = protein
                        organism = synthetic construct
SEQUENCE: 51
QVQLVQSGAE VKKPGASVKV SCKASGFNIE DYYMHWVRQA PGQRLEWMGR IDPEDAETTY    60
SPKFQGRVTI IPDTSANTAY MELSSLRSED TAVYYCARSI YLDPMDYWGQ GTLVTVSS    118

SEQ ID NO: 52           moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 52
GFNIEDYY                                                              8

SEQ ID NO: 53           moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 53
IDPEDAET                                                              8

SEQ ID NO: 54           moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 54
ARSIYLDPMD Y                                                         11

SEQ ID NO: 55           moltype = DNA  length = 354
FEATURE                 Location/Qualifiers
misc_feature            1..354
                        note = source = /note="Description of Artificial Sequence:
                         Synthetic polynucleotide"
source                  1..354
                        mol_type = other DNA
                        organism = synthetic construct
SEQUENCE: 55
caggtgcagc tggtgcagtc tggcgccgaa gtgaaaaagc ctggcgcctc tgtgaaggtg    60
tcctgcaagg cctctggctt caacatcgag gactactaca tgcactgggt ccgacaggcc   120
cctggccaga gattggaatg gatgggcaga atcgaccccg aggacgccga gacaacctac   180
tctcctaagt tccagggccg cgtgacaatc atccctgaca cctctgccaa caccgcctac   240
atggaactgt ccagcctgag atctgaggac accgccgtgt actactgcgc ccggtctatc   300
tacctggacc ctatggacta ttggggccag ggcaccctgg tcacagtgtc ctct          354

SEQ ID NO: 56           moltype = AA  length = 107
FEATURE                 Location/Qualifiers
REGION                  1..107
                        note = source = /note="Description of Artificial Sequence:
                         Synthetic polypeptide"
source                  1..107
                        mol_type = protein
                        organism = synthetic construct
SEQUENCE: 56
DIQMTQSPKS LSASVGDRVT ITCRASQDVT TALAWYQQKP GQSPKLLIYW ATTRHSGVPS    60
RFSGSGSGTD FTLTISSLQP EDFATYYCQQ HYSTPYTFGQ GTKLEIK                 107

SEQ ID NO: 57           moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 57
QDVTTA                                                                6
```

```
SEQ ID NO: 58          moltype =    length =
SEQUENCE: 58
000

SEQ ID NO: 59          moltype = AA   length = 9
FEATURE                Location/Qualifiers
REGION                 1..9
                       note = source = /note="Description of Artificial Sequence:
                        Synthetic peptide"
source                 1..9
                       mol_type = protein
                       organism = synthetic construct
SEQUENCE: 59
QQHYSTPYT                                                                 9

SEQ ID NO: 60          moltype = DNA   length = 321
FEATURE                Location/Qualifiers
misc_feature           1..321
                       note = source = /note="Description of Artificial Sequence:
                        Synthetic polynucleotide"
source                 1..321
                       mol_type = other DNA
                       organism = synthetic construct
SEQUENCE: 60
gacatccaga tgacccagtc tccaaagtct ctgtccgcct ccgtgggcga cagagtgacc   60
atcacctgta gagcctctca ggacgtgacc accgctctgg cttggtatca gcagaagcct  120
ggccagtctc ctaagctgct gatctactgg gccaccacca gacactctgg cgtgccctct  180
agattctccg gctctggctc tggcaccgac tttaccctga caatcccagc ctgcagcct  240
gaggacttcg ccacctacta ctgccagcag cactacagca cccccttacac ctttggccag  300
ggcaccaagc tggaaatcaa g                                             321

SEQ ID NO: 61          moltype = AA   length = 447
FEATURE                Location/Qualifiers
source                 1..447
                       mol_type = protein
                       organism = Mus musculus
SEQUENCE: 61
QVQLQQPGAE LAKPGASVKM SCKASGYTFT SYWITWVKQR PGQDLEWIGN IYPGSGSTYY    60
NEKFKSKATL TVDTSSRTAY MQLSSLTSAD SAVYYCAPYD SDYAMDYWGQ GTSVTVSSAK   120
TTAPSVYPLA PVCGDTTGSS VTLGCLVKGY FPEPVTLTWN SGSLSSGVHT FPAVLQSDLY   180
TLSSSVTVTS STWPSQSITC NVAHPASSTK VDKKIEPRGP TIKPCPPCKC PAPNLLGGPS   240
VFIFPPKIKD VLMISLSPIV TCVVVDVSED DPDVQISWFV NNVEVHTAQT QTHREDYNST   300
LRVVSALPIQ HQDWMSGKEF KCKVNNKDLP APIERTISKP KGSVRAPQVY VLPPPEEEMT   360
KKQVTLTCMV TDFMPEDIYV EWTNNGKTEL NYKNTEPVLD SDGSYFMYSK LRVEKKNWVE   420
RNSYSCSVVH EGLHNHHTTK SFSRTPG                                       447

SEQ ID NO: 62          moltype = DNA   length = 1347
FEATURE                Location/Qualifiers
source                 1..1347
                       mol_type = other DNA
                       organism = Mus musculus
SEQUENCE: 62
caggtccaac tgcagcagcc tggggctgag cttgcgaagc ctggggcttc agtgaagatg    60
tcctgcaagg cttctggcta caccttcacc agctactgga taacctgggt gaagcagagg   120
cctggacaag accttgagtg gattggaaat atttatcctg gtagtggtag tacttactac   180
aatgagaagt tcaagagcaa ggccacactg actgtagaca catcctccag aacagcctac   240
atgcagctca gcagtctgac atctgcggac tctgcggtct attactgtgc ccctatgat   300
tccgactatg ctatggacta ctggggtcaa ggaacctcag tcaccgtctc ctcagctaaa   360
acaacagccc catcggtcta tccactggcc cctgtgtgtg gagatacaac tggctcctcg   420
gtgactctag gatgcctggt caagggttat ttccctgagc cagtgacctt gacctggaac   480
tctggttccc tgtccagtgg tgtgcacacc ttcccagctg tcctgcagtc tgacctctac   540
accctcagct caagcgtgac tgtaaccagc tcgacctggc ccagccagtc catcacctgc   600
aatgtggccc accggcaag cagcaccaag gtggacaaga aaattgagcc cagagggccc   660
acaatcaagc cctgtcctcc atgcaaatgc ccagcaccta acctcttggg tggaccatcc   720
gtcttcatct tccctccaaa gatcaaggat gtactcatga tctccctgag ccccatagtc   780
acatgtgtag tcgttgatgt gagcgaggat gacccagatg tccagatcag ctggtttgtg   840
aacaacgtgg aagtgcacac tgctcagaca cagacgcata gagaggatta caacagtact   900
ctccgggttg tcagtgccct ccccatccag caccaggact ggatgagtgg caaggagttc   960
aaatgcaagg tcaacaacaa agacctccca gcgcccatcg agagaaccat ctcaaaaccc  1020
aaagggtcag taagagctcc acaggtatat gtcttgcctc caccagaaga ggagatgact  1080
aagaaacagg tcactctgac ctgcatggtc acagacttca tgcctgaaga catttacgtg  1140
gagtggacca acaacgggaa aacagagcta aactacaaga acactgaacc agtcctggac  1200
tctgatggtt cttacttcat gtacagcaag ctgagagtgg agaagaagaa ctgggtggag  1260
agaaatagct actcctgttc agtggtccac gagggtctgc acaatcacca cacgactaag  1320
agcttctccc ggactccggg ttagtaa                                      1347

SEQ ID NO: 63          moltype = AA   length = 214
FEATURE                Location/Qualifiers
source                 1..214
```

```
                        mol_type = protein
                        organism = Mus musculus
SEQUENCE: 63
DIKMTQSPSS MYASLGERVT ITCKASQDIN NYLSWFQQKP GKSPKTLIYR ANRLVDGVPS      60
RVSGSGSGQD YSLTISSLEY EDVGIYFCLQ YDEFPLTFGA GTKLELKRAD AAPTVSIFPP     120
SSEQLTSGGA SVVCFLNNFY PKDINVKWKI DGSERQNGVL NSWTDQDSKD STYSMSSTLT     180
LTKDEYERHN SYTCEATHKT STSPIVKSFN RNEC                                 214

SEQ ID NO: 64           moltype = DNA  length = 642
FEATURE                 Location/Qualifiers
source                  1..642
                        mol_type = other DNA
                        organism = Mus musculus
SEQUENCE: 64
gacatcaaga tgacccagtc tccatcttcc atgtatgcat ctctaggaga gagagtcact      60
atcacttgca aggcgagtca ggacattaat aactatttaa gctggttcca gcagaaacca     120
gggaaatctc ctaagaccct gatctatcgt gcaaacagat tggtagatgg ggtcccatca     180
agggtcagtg gcagtggatc tgggcaagat tattctctca ccatcagcag cctggagtat     240
gaagatgtgg gaatttattt ttgtctacag tatgatgagt ttcctctcac gttcggtgct     300
gggaccaagc tggagctgaa aagagctgac gccgctccta ccgtgtccat cttttccacct    360
agcagcgagc agctgacaag cggcggagcc agcgtcgtgt gcttcctgaa caacttctac     420
cccaaggaca tcaacgtgaa gtggaagatc gacggcagcg agagacagaa cggcgtgctg     480
aatagctgga ccgaccagga cagcaaggac tccacctaca gcatgtccag cacactgacc     540
ctgaccaagg acgagtacga gcggcacaac agctacacat gcgaggccac acacaagacc     600
agcacaagcc ccatcgtgaa gtccttcaac cggaacgagt gc                        642

SEQ ID NO: 65           moltype = AA  length = 455
FEATURE                 Location/Qualifiers
source                  1..455
                        mol_type = protein
                        organism = Mus musculus
SEQUENCE: 65
EVQLQQSGAE LVKPGASVKL SCTASGFNIK DYYIHWVKER TEQGLEWFGR IDPEDGESEY      60
APKFQGKATL TADTSSNTAY LQLSSLTSED TAVYYCTRGD SMMVTYFDYW GQGTTLTVSS     120
KTTPPSVYPL APGCGDTTGS SVTLGCLVKG YFPESVTVTW NSGSLSSSVH TFPALLQSGL     180
YTMSSSVTVP SSTWPSQTVT CSVAHPASST TVDKKLEPSG PISTINPCPP CKECHKCPAP     240
NLEGGPSVFI FPPNIKDVLM ISLTPKVTCV VVDVSEDDPD VQISWFVNNV EVHTAQTQTH     300
REDYNSTIRV VSTLPIQHQD WMSGKEFKCK VNNKDLPSPI ERTISKIKGL VRAPQVYILP     360
PPAEQLSRKD VSLTCLVVGF NPGDISVEWT SNGHTEENYK DTAPVLDSDG SYFIYSKLNM     420
KTSKWEKTDS FSCNVRHEGL KNYYLKKTIS RSPGK                                455

SEQ ID NO: 66           moltype = DNA  length = 1365
FEATURE                 Location/Qualifiers
source                  1..1365
                        mol_type = other DNA
                        organism = Mus musculus
SEQUENCE: 66
gaggttcagc tgcagcagtc tggggcagaa cttgtgaagc caggggcctc agtcaagttg      60
tcctgcacag cctctggctt caacattaaa gactactata cacactgggt gaagagagg      120
actgaacagg gcctggagtg gtttggaagg attgatcctg aggatggtga agtgaatat      180
gccccgaaat tccagggcaa ggccactttc acagcagaca catcctccaa tacagcctac     240
ctgcagctca gcagcctgac atctgaggac actgccgtct attactgtac tagaggagac     300
tctatgatgg ttacctactt tgactactgg ggccaaggca ccactctcac ggtctcctca     360
aagaccacac tcctagcgt gtaccctctg gctcctggct gtggcgatac aacaggcagc     420
tctgtgacac tgggctgcct ggtcaagggc tactttcctg agagcgtgac agtgacctgg     480
aacagcggca gcctgtctag cagcgtgcac acctttccag ctctgctcca gagcggcctg     540
tacaccatgt cctctagtgt gaccgtgcct agcagcacct ggcctagcca gacagtgaca     600
tgtagcgtgg cccatcctgc cagcagcaca accgtggaca agaagctgga acctagcggc     660
cccatcagca ccatcaatcc ctgtcctcca tgcaaagaat gccacaagtg ccccgctcct     720
aacctggaag tgggccaag cgtgttcatc ttcccaccta acatcaagga cgtgctgatg     780
atcagcctga cacctaaagt gacctgcgtg gtggtggacg tgtccgagga tgatcccgat     840
gtgcagatca gttggttcgt gaacaacgtg gaagtgcaca cagcccagac acagacccac     900
agagaggact acaatagcac cattcgcgtg gtgtccacac tgcctatcca gcaccaggat     960
tggatgagcg gcaaagagtt caagtgcaaa gtgaacaaca aggacctgcc ttctccaatc    1020
gagcggacca tcagcaagat caagggactc gtcagagccc ctcaggtgta catcttgcct    1080
ccaccagccg agcagctgag cagaaaggat gtgtccctga cctgtctggt cgtgggcttc    1140
aaccctggcg acatcagcgt ggaatggacc agcaatggcc acaccgagga aaactacaag    1200
gacacagccc ctgtgctgga cagcgacggc agctacttca tctacagcaa gctgaacatg    1260
aagaccagca agtgggagaa aaccgacagc ttctcctgca acgtgcggca cgaggcgctg    1320
aagaactact acctgaagaa aaccatctct cggagccccg gcaag                    1365

SEQ ID NO: 67           moltype = AA  length = 214
FEATURE                 Location/Qualifiers
source                  1..214
                        mol_type = protein
                        organism = Mus musculus
SEQUENCE: 67
DIVMTQSHKF MSTSVGDRVS ITCKASQDVS TAVAWYQQKP GQSPKLLIYW AFTRHTGVPD      60
RFTSTGSGTD YALTISSVQA EDLALYYCQQ HYRSPWTFGG GTKLEIKRAD AAPTVSIFPP     120
```

```
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNEC                              214

SEQ ID NO: 68              moltype = DNA   length = 642
FEATURE                    Location/Qualifiers
source                     1..642
                           mol_type = other DNA
                           organism = Mus musculus
SEQUENCE: 68
gacattgtga tgacccagtc tcacaaattc atgtccacat cagtaggaga cagggtcagc    60
atcacctgca aggccagtca ggatgtgagt actgctgtag cctggtatca acaaaaacca   120
gggcaatctc ctaaactact gatttactgg gctttcaccc gtcacactgg agtccctgat   180
cgcttcacaa gcactggatc tgggacagat tatgctctca ccatcagcag tgtgcaggct   240
gaagacctgg cactttatta ctgtcagcaa cattatcgca gtccgtggac gttcggtgga   300
ggcaccaaac tggaaatcaa agagctgac gccgctccta ccgtgtccat ctttccacct   360
agcagcgagc agctgacaag cggcggagcc agcgtcgtgt gcttcctgaa caacttctac   420
cccaaggaca tcaacgtgaa gtggaagatc acggcagcg agacagaa cggcgtgctg   480
aatagctgga ccgaccagga cagcaaggac tccacctaca gcatgtccag cacactgacc   540
ctgaccaagg acgagtacga gcggcacaac agctacacat gcgaggccac acacaagacc   600
agcacaagcc ccatcgtgaa gtccttcaac cggaacgagt gc                     642

SEQ ID NO: 69              moltype = AA   length = 453
FEATURE                    Location/Qualifiers
source                     1..453
                           mol_type = protein
                           organism = Mus musculus
SEQUENCE: 69
EVQLQQSGAE LVKPGASVKL SCTASGFNIE DYYIHWVKER TEQGLEWIGR IDPEDGETTY    60
APQFQGKATI IPDTSSNTAY MQLSSLTSED AAVYYCARSI YLDPMDYWGQ GTSVTVSSKT   120
TPPSVYPLAP GCGDTTGSSV TLGCLVKGYF PESVTVTWNS GSLSSSVHTF PALLQSGLYT   180
MSSSVTVPSS TWPSQTVTCS VAHPASSTTV DKKLEPSGPI STINPCPPCK ECHKCPAPNL   240
EGGPSVFIFP PNIKDVLMIS LTPKVTCVVV DVSEDDPDVQ ISWFVNNVEV HTAQTQTHRE   300
DYNSTIRVVS TLPIQHQDWM SGKEFKCKVN NKDLPSPIER TISKIKGLVR APQVYILPPP   360
AEQLSRKDVS LTCLVVGFNP GDISVEWTSN GHTEENYKDT APVLDSDGSY FIYSKLNMKT   420
SKWEKTDSFS CNVRHEGLKN YYLKKTISRS PGK                                453

SEQ ID NO: 70              moltype = DNA   length = 1359
FEATURE                    Location/Qualifiers
source                     1..1359
                           mol_type = other DNA
                           organism = Mus musculus
SEQUENCE: 70
gaggttcagc tgcagcagtc tggcgccgag cttgtgaaac ctggcgcctc tgtgaagctg    60
agctgtaccg ccagcggctt caacatcgag gactactaca tccactgggt caaagagcgg   120
accgagcagg gactcgagtg gatcggaaga atcgaccccg aggacggcga gacaacatac   180
gcccctcagt tcagggcaa agccacaatc atccccgaca ccagcagcaa caccgcctac   240
atgcaactga gcagcctgac ctctgaagat gccgccgtgt actactgcgc ccggtccatc   300
tatctggacc ccatggatta ttgggggcag ggcacaagcg tgaccgtgtc ctctaagacc   360
acacctccta gcgtgtaccc tctggctcct ggctgtggcg atacaacagg cagctctgtg   420
acactgggct gcctggtcaa gggctacttt cctgagagcg tgacagtgac ctggaacagc   480
ggcagcctgt ctagcagcgt gcacaccttt ccagctctgc tccagagcgg cctgtacacc   540
atgtcctcta gtgtgaccgt gcctagcagc acctggccta gccagacagt gacatgtagc   600
gtggcccatc ctgccagcag cacaaccgtg gacaagaagc tggaacctag cggccccatc   660
agcaccatca tccctgtcc tccatgcaaa gaatgccaca gtgccccgc tcctaacctg   720
gaaggtggcc caagcgtgtt catcttccca cctaacatca aggacgtgct gatgatcagc   780
ctgacaccta agtgacctg cgtggtggtg gacgtgtccg aggatgatcc cgatgtgcag   840
atcagttggt tcgtgaacaa cgtggaagtg cacacagccc agacagac ccacagagag   900
gactacaata gcaccattcg cgtggtgtcc acactgccta ccagcacca ggattggatg   960
agcggcaaag agttcaagtg caaagtgaac aacaaggacc tgccttctcc aatcgagcgg  1020
accatcagca agatcaaggg actcgtcaga gcccctcagg tgtacatctt gcctccacca  1080
gccgagcagc tgagcagaaa ggatgtgtcc ctgacctgtc tggtcgtggg cttcaaccct  1140
ggcgacatca gcgtggaatg gaccagcaat ggccacaccg gaaaaacta aaggacaca  1200
gcccctgtgc tggacagcga cggcagctac ttcatctaca gcaagctgaa catgaagacc  1260
agcaagtggg agaaaaccga cagcttctcc tgcaacgtgc ggcacgaggg cctgaagaac  1320
tactacctga agaaaaccat ctctcggagc cccggcaag                         1359

SEQ ID NO: 71              moltype = AA   length = 214
FEATURE                    Location/Qualifiers
source                     1..214
                           mol_type = protein
                           organism = Mus musculus
SEQUENCE: 71
DIVMTQSHKF MSTSVGDRVS ITCKASQDVT TAVAWYQQKP GQSPKILIYW ATTRHTGVPD    60
RFTGSISGTT YILTISSVQA EDLALYYCQQ HYSTPYTFGG GTKLEIKRAD AAPTVSIFPP   120
SSEQLTSGGA SVVCFLNNFY PKDINVKWKI DGSERQNGVL NSWTDQDSKD STYSMSSTLT   180
LTKDEYERHN SYTCEATHKT STSPIVKSFN RNEC                              214

SEQ ID NO: 72              moltype = DNA   length = 642
FEATURE                    Location/Qualifiers
```

```
                              source           1..642
                                               mol_type = other DNA
                                               organism = Mus musculus
                              SEQUENCE: 72
                              gacatcgtga tgacccagag ccacaagttc atgagcacca gcgtgggcga cagagtgtcc   60
                              atcacctgta aagccagcca ggacgtgaca acagccgtgg cctggtatca gcagaagcct  120
                              ggccagtctc ctaagatcct gatctactgg gccaccacca gacacaccgg cgtgccagat  180
                              agattcaccg gcagcatcag cggcaccacc tacatcctga caatcagctc tgtgcaggcc  240
                              gaggatctgg ccctgtacta ctgtcagcag cactacagca ccccttacac ctttggcgga  300
                              ggcaccaagc tggaaatcaa gagagctgac gccgctccta ccgtgtccat ctttccacct  360
                              agcagcgagc agctgacaag cggcggagcc agcgtcgtgt gcttcctgaa caacttctac  420
                              cccaaggaca tcaacgtgaa gtggaagatc gacggcagcg agagacagaa cggcgtgctg  480
                              aatagctgga ccgaccagga cagcaaggac tccacctaca gcatgtccag cacactgacc  540
                              ctgaccaagg acgagtacga gcggcacaac agctacacat gcgaggccac acacaagacc  600
                              agcacaagcc ccatcgtgaa gtccttcaac cggaacgagt gc                     642

SEQ ID NO: 73    moltype = AA  length = 447
                              FEATURE          Location/Qualifiers
                              REGION           1..447
                                               note = source = /note="Description of Artificial Sequence:
                                               Synthetic polypeptide"
                              source           1..447
                                               mol_type = protein
                                               organism = synthetic construct
                              SEQUENCE: 73
                              EVQLVQSGAE VKKPGASVKV SCKASGYTFT SYWITWVRQA PGQRLEWIGN IYPGSGSTYY   60
                              NEKFKSKATI TRDTSSRTAY MELSSLRSED TAVYYCAPYD ADYAMDYWGQ GTLVTVSSAS  120
                              TKGPSVFPLA PSSKSTSGGT AALGCLVKDY FPEPVTVSWN SGALTSGVHT FPAVLQSSGL  180
                              YSLSSVVTVP SSSLGTQTYI CNVNHKPSNT KVDKKVEPKS CDKTHTCPPC PAPELLGGPS  240
                              VFLFPPKPKD TLMISRTPEV TCVVVDVSHE DPEVKFNWYV DGVEVHNAKT KPREEQYAST  300
                              YRVVSVLTVL HQDWLNGKEY KCKVSNKALP APIEKTISKA KGQPREPQVY TLPPSRDELT  360
                              KNQVSLTCLV KGFYPSDIAV EWESNGQPEN NYKTTPPVLD SDGSFFLYSK LTVDKSRWQQ  420
                              GNVFSCSVMH EALHNHYTQK SLSLSPG                                       447

SEQ ID NO: 74    moltype = DNA  length = 1341
                              FEATURE          Location/Qualifiers
                              misc_feature     1..1341
                                               note = source = /note="Description of Artificial Sequence:
                                               Synthetic polynucleotide"
                              source           1..1341
                                               mol_type = other DNA
                                               organism = synthetic construct
                              SEQUENCE: 74
                              gaagtgcagc tggtgcaatc tggcgccgaa gtgaagaaac ctggcgcctc tgtgaaggtg   60
                              tcctgcaagg cttccggcta cacctttacc agctactgga tcacctgggt ccgacaggct  120
                              cctggccaga gactggaatg gatcggcaac atctaccctg gctccggctc cacctactac  180
                              aacgagaagt tcaagtccaa ggccacaatc acccgggaca cctcttccag aaccgcctac  240
                              atggaactgt ccagcctgag atctgaggac accgccgtgt actactgcgc ccccttacgac  300
                              gccgactacg ccatggatta ttggggccag ggcaccctgg tcaccgtgtc ctctgctcct  360
                              accaagggac ccagcgtgtt ccctctggct ccttccagca gtctacctcc tggcggaaca  420
                              gctgctctgg gctgcctggt caaggactac tttcctgagc ctgtgaccgt gtcttggaac  480
                              tctggcgctc tgacatccgg cgtgcacaca tttccagctg tgctgcagtc ctccggcctg  540
                              tactctctgt cctctgtcgt gaccgtgcct cctctagcc tgggcaccca gacctacatc  600
                              tgcaatgtga accacaagcc ttccaacacc aaggtggaca gaaggtgga acccaagtcc  660
                              tgcgacaaga cccacacctg tcctccatgt cctgctccag aactgctcgg cggaccttcc  720
                              gtgttcctgt ttcctccaaa gcctaaggac accctgatga tctctcggac ccctgaagtg  780
                              acctgcgtgg tggtggatgt gtctcacgag acccagaag tgaagttcaa ttggtacgtg  840
                              gacggcgtgg aagtgcacaa cgccaagacc aagcctagag gaacagta cgccagcacc  900
                              tacagagtgg tgtccgtgct gacagtgctg caccaggatt ggctgaacgg caaagagtac  960
                              aagtgcaagg tgtccaacaa ggccctgcct gctccatcg aaaagaccat cagcaaggcc 1020
                              aagggccagc ctagagaacc caggttac accttgcctc catctcggga cgagctgacc 1080
                              aagaaccagg tgtccctgac ctgtctcgtg aagggcttct acccctccga catcgccgtg 1140
                              gaatgggagt ctaatggcca gccagagaac aactacaaga caacccctcc tgtgctggac 1200
                              tccgacggct cattcttcct gtactccaag ctgaccgtgg acaagtccag atggcagcag 1260
                              ggcaacgtgt tctcctgctc cgtgatgcac gaggccctgc acaatcacta cacacagaag 1320
                              tccctgtctc tgtcccctgg c                                          1341

SEQ ID NO: 75    moltype = AA  length = 214
                              FEATURE          Location/Qualifiers
                              REGION           1..214
                                               note = source = /note="Description of Artificial Sequence:
                                               Synthetic polypeptide"
                              source           1..214
                                               mol_type = protein
                                               organism = synthetic construct
                              SEQUENCE: 75
                              DIQMTQSPSS LSASVGDRVT ITCKASQDIS NYLSWFQQKP GKAPKLLIYR ANRLVEGVPS   60
                              RFSGSGSGTD FTLTISSLQP EDFATYFCLQ YDEFPLTFGG GTKVEIKRTV AAPSVFIFPP  120
                              SDEQLKSGTA SVVCLLNNFY PREAKVQWKV DNALQSGNSQ ESVTEQDSKD STYSLSSTLT  180
```

LSKADYEKHK VYACEVTHQG LSSPVTKSFN RGEC                                          214

```
SEQ ID NO: 76           moltype = DNA   length = 642
FEATURE                 Location/Qualifiers
misc_feature            1..642
                        note = source = /note="Description of Artificial Sequence:
                        Synthetic polynucleotide"
source                  1..642
                        mol_type = other DNA
                        organism = synthetic construct
SEQUENCE: 76
gacatccaga tgacccagtc tccatcctct ctgtccgcct ctgtgggcga cagagtgacc   60
atcacatgca aggccagcca ggacatctcc aactacctgt cctggttcca gcagaagcct  120
ggcaaggctc ccaagctgct gatctacaga gccaacagac tggtgaagg cgtgcccttc  180
agattctccg gatctggctc tggcaccgac tttaccctga caatctccag cctgcagcct  240
gaggacttcg ctacctactt ctgcctgcaa tacgacgagt ccctctgac ctttggcgga  300
ggcaccaagg tggaaatcaa gcggacagtg gccgctcctt ccgtgttcat cttcccacct  360
tccgacgagc agctgaagtc tggaacagct ctgtcgtgt gctgctgaa caacttctac  420
cctcgggaag ccaaggtgca gtggaaggtg gacaatgccc tgcagtccgg caactcccaa  480
gagtctgtga ccgagcagga ctccaaggac agcacctaca gcctgtcctc cacactgacc  540
ctgtccaagg ccgactacga gaagcacaag gtgtacgcct gcgaagtgac ccatcagggc  600
ctgtctagcc ctgtgaccaa gtctttcaac cggggcgagt gt                     642

SEQ ID NO: 77           moltype = AA   length = 449
FEATURE                 Location/Qualifiers
REGION                  1..449
                        note = source = /note="Description of Artificial Sequence:
                        Synthetic polypeptide"
source                  1..449
                        mol_type = protein
                        organism = synthetic construct
SEQUENCE: 77
EVQLVQSGAE VKKPGASVKV SCKASGFNIK DYYIHWVRQA TGQGLEWMGR IDPEDAESEY   60
APKFQGRVTI TADTSTDTAY MELSSLRSED TAVYYCTRGD SMMVTYFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYA  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                    449

SEQ ID NO: 78           moltype = DNA   length = 1347
FEATURE                 Location/Qualifiers
misc_feature            1..1347
                        note = source = /note="Description of Artificial Sequence:
                        Synthetic polynucleotide"
source                  1..1347
                        mol_type = other DNA
                        organism = synthetic construct
SEQUENCE: 78
gaagtgcagc tggtgcaatc tggcgccgaa gtgaagaaac ctggcgcctc tgtgaaggtg   60
tcctgcaagg cctctggctt caacatcaag gactactaca tccactgggt ccgacaggct  120
accggacagg gacttgagtg gatgggcaga atcgaccctg aggacgccga gtctgagtac  180
gcccctaagt tcagggcag agtgaccatc accgccgaca cctctaccga caccgcctac  240
atggaactgt ccagcctgag atctgaggac accgccgtgt actactgcac cagaggcgac  300
tccatgatgg ttacctactt cgactactgg ggccagggca ccctggtcac agtttcttcc  360
gcttccacca agggacccag cgtgttccct ctggctcctt ccagcaagtc tacctctggc  420
ggaacagctg ctctgggctg cctggtcaag gattacttcc ctgagcctgt gaccgtgtcc  480
tggaactctg gcgctctgac atccggcgtg cacaccttc agctgtgct gcaatcctcc  540
ggcctgtact ctctgtcctc cgtcgtgacc gtgccttcta gctctctggg cacccagacc  600
tacatctgca atgtgaacca caagcctccc aacaccaagg tggacaagaa ggtgaacccc  660
aagtcctgcg acaagaccca cacctgtcct ccatgtcctg ctccagaact gctcggcgga  720
ccttccgtgt tcctgttttcc tccaaagcct aaggacaccc tgatgatctc tcggaccct  780
gaagtgacct gcgtggtggt ggatgtgtct cacgaggtga agttcaattgg  840
tacgtggacg gcgtggaagt gcacaacgcc aagaccaagc ctagagagga acagtacgcc  900
tccacctaca gagtggtgtc cgtgctgaca gtgctgcacc aggattggct gaacggcaaa  960
gagtacaagt gcaaggtgtc caacaaggca ctgcccgctc ctatcgaaaa gaccatctcc 1020
aaggccaagg gccagcctag agaacccag gtttacactc tgcctccatc tcgggacgag 1080
ctgaccaaga accaggtgtc cctgacctgt ctcgtgaagg gcttctaccc ctccgacatc 1140
gccgtggaat gggagtctaa tggccagcca gagaacaact acaagacaac cctcctgtg 1200
ctggactccg acggctcatt cttcctgtac tccaagctga ccgtggacaa gtccagatgg 1260
cagcagggca acgtgttctc ctgctccgtg atgcacgagg ccctgcacaa tcactacaca 1320
cagaagtctc tgtccctgtc tcctggc                                    1347

SEQ ID NO: 79           moltype = AA   length = 214
FEATURE                 Location/Qualifiers
REGION                  1..214
                        note = source = /note="Description of Artificial Sequence:
                        Synthetic polypeptide"
```

```
                         source          1..214
                                         mol_type = protein
                                         organism = synthetic construct
SEQUENCE: 79
DIQMTQSPSS LSASVGDRVT ITCKASQDVS TAVAWYQQKP GKAPKLLIYW AFTRHTGVPS      60
RFSGSGSGTD YALTISSLQP EDFATYYCQQ HYRSPWTFGG GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 80            moltype = DNA    length = 642
FEATURE                  Location/Qualifiers
misc_feature             1..642
                         note = source = /note="Description of Artificial Sequence:
                           Synthetic polynucleotide"
source                   1..642
                         mol_type = other DNA
                         organism = synthetic construct
SEQUENCE: 80
gacatccaga tgacccagtc tccatcctct ctgtccgcct ctgtgggcga cagagtgacc      60
atcacatgca aggcctctca ggacgtgtcc accgccgttg cttggtatca gcagaagcct     120
ggcaaggccc ctaagctgct gatctactgg gccttcacca cacaccggg cgtgccctct      180
aggttctccg gctctggctc tggcaccgat tacgctctga caatcctcag cctgcagcct     240
gaggacttcg ccacctacta ctgccagcag cactacagaa gcccctggac atttggcgga     300
ggcaccaagg tggaaatcaa gcggacagtg gccgctcctt ccgtgttcat cttcccacct     360
tccgacgagc agctgaagtc cggcacagct tctgtcgtgt gcctgctgaa caacttctac     420
cctcgggaag ccaaggtgca gtggaaggtg gacaatgccc tgcagtccgg caactcccaa     480
gagtctgtga ccgagcagga ctccaaggac agcacctaca gcctgtcctc cacactgacc     540
ctgtccaagg ccgactacga aagcacaag gtgtacgcct gcgaagtgac ccatcagggc      600
ctgtctagcc ctgtgaccaa gtctttcaac cggggcgagt gt                         642

SEQ ID NO: 81            moltype = AA    length = 447
FEATURE                  Location/Qualifiers
REGION                   1..447
                         note = source = /note="Description of Artificial Sequence:
                           Synthetic polypeptide"
source                   1..447
                         mol_type = protein
                         organism = synthetic construct
SEQUENCE: 81
QVQLVQSGAE VKKPGASVKV SCKASGFNIE DYYMHWVRQA PGQRLEWMGR IDPEDAETTY      60
SPKFQGRVTI IPDTSANTAY MELSSLRSED TAVYYCARSI YLDPMDYWGQ GTLVTVSSAS     120
TKGPSVFPLA PSSKSTSGGT AALGCLVKDY FPEPVTVSWN SGALTSGVHT FPAVLQSSGL     180
YSLSSVVTVP SSSLGTQTYI CNVNHKPSNT KVDKKVEPKS CDKTHTCPPC PAPEAAGGPS     240
VFLFPPKPKD TLMISRTPEV TCVVVDVSHE DPEVKFNWYV DGVEVHNAKT KPREEQYNST     300
YRVVSVLTVL HQDWLNGKEY KCKVSNKALP APIEKTISKA KGQPREPQVY TLPPSREEMT     360
KNQVSLTCLV KGFYPSDIAV EWESNGQPEN NYKTTPPVLD SDGSFFLYSK LTVDKSRWQQ     420
GNVFSCSVMH EALHNHYTQK SLSLSPG                                         447

SEQ ID NO: 82            moltype = DNA    length = 1341
FEATURE                  Location/Qualifiers
misc_feature             1..1341
                         note = source = /note="Description of Artificial Sequence:
                           Synthetic polynucleotide"
source                   1..1341
                         mol_type = other DNA
                         organism = synthetic construct
SEQUENCE: 82
caggtgcagc tggtgcagtc tggcgccgaa gtgaaaaagc ctggcgcctc tgtgaaggtg      60
tcctgcaagg cctctggctt caacatcgag gactactaca tgcactgggt ccgacaggcc     120
cctggccaga gattggaatg gatgggcaga atcgaccccg aggacgccga gacaacctac     180
tctcctaagt tccagggccg cgtgacaatc atccctgaca cctctgccaa caccgcctac     240
atggaactgt ccagcctgag atctgaggac accgccgtgt actactgcgc ccggtctatc     300
tacctggacc ctatggacta ttggggccag ggcaccctgg tcacagtgtc ctctgcttct     360
accaagggac ccagcgtgtt ccctctggct ccttccagca gtctacctc tggcggaaca      420
gctgctctgg gctgcctggt caaggactac tttccagagc ctgtgaccgt gtcctggaac     480
tctggcgctc tgacatctgg cgtgcacacc tttccagctg tgctgcagtc ctccggcctg     540
tactctctgt cctctgtcgt gaccgtgcct tccagctctc tgggaaccca gacctacatc     600
tgcaatgtga accacaagcc ttccaacacc aaggtggaca gaaggtggaa acccaagtgc     660
tgcgacaaga cccacacctg tcctccatgt cctgctccag aagctgctgg cggcccttcc     720
gtgtttctgt tccctccaaa gcctaaggac accctgatga tctctcggac ccctgaagtg     780
acctgcgtgt tggtggatgt gtctcacgag gaccagaag tgaagttcaa ttggtacgtg      840
gacggcgtga agtgcacaa cgccaagacc aagcctagag gaacagta caactccacc        900
tacagagtgg tgtccgtgct gaccgtgctg caccaggatt ggctgaacgg caaagagtac     960
aagtgcaagg tgtccaacaa ggcactgccc gctcctatcg aaaagaccat ctccaaggcc    1020
aagggccagc ctagggaacc ccaggtttac accctgcctc aagccgggga agagatgacc    1080
aagaaccagg tgtccctgac ctgcctcgtg aagggcttct acccttccga catcgccgtg    1140
gaatgggaga gcaatggcca gccagagaac aactacaaga caccccctcc tgtgctggac    1200
tccgacggct cattcttcct gtactccaag ctgacagtgg acaagtccag atggcagcag    1260
ggcaacgtgt tctcctgctc cgtgatgcac gaggccctgc acaatcacta cacacagaag    1320
```

```
tccctgtctc tgtccsctgg c                                            1341
```

SEQ ID NO: 83          moltype = AA   length = 214
FEATURE                Location/Qualifiers
REGION                 1..214
                       note = source = /note="Description of Artificial Sequence:
                         Synthetic polypeptide"
source                 1..214
                       mol_type = protein
                       organism = synthetic construct
SEQUENCE: 83
```
DIQMTQSPKS LSASVGDRVT ITCRASQDVT TALAWYQQKP GQSPKLLIYW ATTRHSGVPS   60
RFSGSGSGTD FTLTISSLQP EDFATYYCQQ HYSTPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214
```

SEQ ID NO: 84          moltype = DNA   length = 642
FEATURE                Location/Qualifiers
misc_feature           1..642
                       note = source = /note="Description of Artificial Sequence:
                         Synthetic polynucleotide"
source                 1..642
                       mol_type = other DNA
                       organism = synthetic construct
SEQUENCE: 84
```
gacatccaga tgacccagtc tccaaagtct ctgtccgcct ccgtgggcga cagagtgacc   60
atcacctgta gagcctctca ggacgtgacc accgctctgg cttggtatca gcagaagcct  120
ggccagtctc ctaagctgct gatctactgg gccaccacca gacactctgg cgtgccctct  180
agattctccg gctctggctc tggcaccgac tttaccctga caatctccag cctgcagcct  240
gaggacttcg ccacctacta ctgccagcag cactacagcc cccttacac ctttggccag  300
ggcaccaagc tggaaatcaa gcggacagtg gccgctcctt ccgtgttcat cttcccacct  360
tccgacgagc agctgaagtc cggcacagct tctgtcgtgt gcctgctgaa caacttctac  420
cctcgggaag ccaaggtgca gtggaaggtg gacaatgccc tgcagtccgg caactcccaa  480
gagtctgtga ccgagcagga ctccaaggac agcacctaca gcctgtcctc cacactgacc  540
ctgtccaagg ccgactacga gaagcacaag gtgtacgcct gcgaagtgac ccatcaggc  600
ctgtctagcc ctgtgaccaa gtctttcaac cggggcgagt gt                     642
```

SEQ ID NO: 85          moltype = DNA   length = 21
FEATURE                Location/Qualifiers
misc_feature           1..21
                       note = source = /note="Description of Artificial Sequence:
                         Synthetic primer"
source                 1..21
                       mol_type = other DNA
                       organism = synthetic construct
SEQUENCE: 85
```
aagcagggca gacattgcga t                                             21
```

SEQ ID NO: 86          moltype = DNA   length = 21
FEATURE                Location/Qualifiers
misc_feature           1..21
                       note = source = /note="Description of Artificial Sequence:
                         Synthetic primer"
source                 1..21
                       mol_type = other DNA
                       organism = synthetic construct
SEQUENCE: 86
```
caggatgtgg ctctaggcta t                                             21
```

SEQ ID NO: 87          moltype = DNA   length = 20
FEATURE                Location/Qualifiers
misc_feature           1..20
                       note = source = /note="Description of Artificial Sequence:
                         Synthetic primer"
source                 1..20
                       mol_type = other DNA
                       organism = synthetic construct
SEQUENCE: 87
```
acccacactg tgcccatcta                                               20
```

SEQ ID NO: 88          moltype = DNA   length = 20
FEATURE                Location/Qualifiers
misc_feature           1..20
                       note = source = /note="Description of Artificial Sequence:
                         Synthetic primer"
source                 1..20
                       mol_type = other DNA
                       organism = synthetic construct
SEQUENCE: 88
```
cacgctcggt caggatcttc                                                    20

SEQ ID NO: 89          moltype = AA   length = 118
FEATURE                Location/Qualifiers
REGION                 1..118
                       note = source = /note="Description of Artificial Sequence:
                       Synthetic polypeptide"
source                 1..118
                       mol_type = protein
                       organism = synthetic construct
SEQUENCE: 89
QVQLVQSGAE VKKPGASVKV SCKASGFNIE DYYMHWVRQA PGQRLEWMGR IDPEDGETTY  60
SPKFQGRVTI IPDTSANTAY MELSSLRSED TAVYYCARSI YLDPMDYWGQ GTLVTVSS   118

SEQ ID NO: 90          moltype = AA   length = 118
FEATURE                Location/Qualifiers
REGION                 1..118
                       note = source = /note="Description of Artificial Sequence:
                       Synthetic polypeptide"
source                 1..118
                       mol_type = protein
                       organism = synthetic construct
SEQUENCE: 90
QVQLQQSGAE VKKPGASVKV SCTASGFNIE DYYINWVRQA TGQGLEWMGR IDPEDGETGY  60
AQKFQGRVTM TRNTSISTAY MELSSLRSED TAVYYCARSI YLDPMDYWGQ GTLVTVSS   118

SEQ ID NO: 91          moltype = AA   length = 118
FEATURE                Location/Qualifiers
REGION                 1..118
                       note = source = /note="Description of Artificial Sequence:
                       Synthetic polypeptide"
source                 1..118
                       mol_type = protein
                       organism = synthetic construct
SEQUENCE: 91
QVQLVQSGAE VKKPGASVKV SCKASGFNIE DYYMHWVRQA PEQGLEWMGR IDPEDGETTY  60
APKFQGRVTS TRDTSINTAY MELSRLRSDD TVVYYCARSI YLDPMDYWGQ GTLVTVSS   118

SEQ ID NO: 92          moltype = AA   length = 118
FEATURE                Location/Qualifiers
REGION                 1..118
                       note = source = /note="Description of Artificial Sequence:
                       Synthetic polypeptide"
source                 1..118
                       mol_type = protein
                       organism = synthetic construct
SEQUENCE: 92
QVQLVQSGAE VKKPGASVKV SCKASGFNIE DYYMHWVRQA PEQGLEWMGI IDPEDGETSY  60
AQKFQGRVTM TRDTSTNTAY MELSSLRSED TAVYYCARSI YLDPMDYWGQ GTLVTVSS   118

SEQ ID NO: 93          moltype = AA   length = 107
FEATURE                Location/Qualifiers
REGION                 1..107
                       note = source = /note="Description of Artificial Sequence:
                       Synthetic polypeptide"
source                 1..107
                       mol_type = protein
                       organism = synthetic construct
SEQUENCE: 93
DIQMTQSPKS LSASVGDRVT ITCRASQDVT TALAWYQQKP GQSPKLLIYW ATTRHSGVPS  60
RFSGSGSGTD FTLTISSLQP EDFATYYCQQ HYSTPYTFGQ GTKLEIK              107

SEQ ID NO: 94          moltype = AA   length = 107
FEATURE                Location/Qualifiers
REGION                 1..107
                       note = source = /note="Description of Artificial Sequence:
                       Synthetic polypeptide"
source                 1..107
                       mol_type = protein
                       organism = synthetic construct
SEQUENCE: 94
DIQMTQSPKS VSASVGDRVT ITCRASQDVT TALAWYQQKP GQSPKLLIYW ATSLQSGVPS  60
RFSGSGSGTD FTLTISSLQP EDFATYYCQQ HYSTPYTFGQ GTKLEIK              107

SEQ ID NO: 95          moltype = AA   length = 107
FEATURE                Location/Qualifiers
REGION                 1..107
                       note = source = /note="Description of Artificial Sequence:
                       Synthetic polypeptide"

```
source                         1..107
                               mol_type = protein
                               organism = synthetic construct
SEQUENCE: 95
DIQMTQSPKS  LSASVGDRVT  ITCQASQDVT  TALNWYQQKP  GKAPKLLIYW  ATNLETGVPS   60
RFSGSGSGTD  FTFTISSLQP  EDIATYYCQQ  HYSTPYTFGQ  GTKLEIK                 107

SEQ ID NO: 96                  moltype = AA  length = 107
FEATURE                        Location/Qualifiers
REGION                         1..107
                               note = source = /note="Description of Artificial Sequence:
                                  Synthetic polypeptide"
source                         1..107
                               mol_type = protein
                               organism = synthetic construct
SEQUENCE: 96
DIVMTQSPKS  LAVSLGERAT  INCKSSQDVT  TALAWYQQKP  GQSPKLLIYW  ATTRESGVPD   60
RFSGSGSGTD  YTLTISSLQA  EDVAVYYCQQ  HYSTPYTFGQ  GTKLEIK                 107

SEQ ID NO: 97                  moltype = AA  length = 808
FEATURE                        Location/Qualifiers
REGION                         1..808
                               note = source = /note="Description of Artificial Sequence:
                                  Synthetic polypeptide"
source                         1..808
                               mol_type = protein
                               organism = synthetic construct
SEQUENCE: 97
MPVAEAPQVA  GGQGDGGDGE  EAEPEGMFKA  CEDSKRKARG  YLRLVPLFVL  LALLVLASAG   60
VLLWYFLGYK  AEVMVSQVYS  GSLRVLNRHF  SQDLTRRESS  AFRSETAKAQ  KMLKELITST  120
RLGTYYNSSS  VYSFGEGPLT  CFFWFILQIP  EHRRLMLSPE  VVQALLVEEL  LSTVNSSAAV  180
PYRAEYEVDP  EGLVILEASV  KDIAALNSTL  GCYRYSYVGQ  GQVLRLKGPD  HLASSCLWHL  240
QGPKDLMLKL  RLEWTLAECR  DRLAMYDVAG  PLEKRLITSV  YGCSRQEPVV  EVLASGAIMA  300
VVWKKGLHSY  YDPFVLSVQP  VVFQACEVNL  TLDNRLDSQG  VLSTPYFPSY  YSPQTHCSWH  360
LTVPSLDYGL  ALWFDAYALR  RQKYDLPCTQ  GQWTIQNRRL  CGLRILQPYA  ERIPVVATAG  420
ITINFTSQIS  LTGPGVRVHY  GLYNQSDPCP  GEFLCSVNGL  CVPACDGVKD  CPNGLDERNC  480
VCRATFQCKE  DSTCISLPKV  CDGQPDCLNG  SDEEQCQEGV  PCGTFTFQCE  DRSCVKKPNP  540
QCDGRPDCRD  GSDEEHCDCG  LQGPSSRIVG  GAVSSEGEWP  WQASLQVRGR  HICGGALIAD  600
RWVITAAHCF  QEDSMASTVL  WTVFLGKVWQ  NSRWPGEVSF  KVSRLLLHPY  HEEDSHDYDV  660
ALLQLDHPVV  RSAAVRPVCL  PARSHFFEPG  LHCWITGWGA  LREGGPISNA  LQKVDVQLIP  720
QDLCSEVYRY  QVTPRMLCAG  YRKGKKDACQ  GDSGGPLVCK  ALSGRWFLAG  LVSWGLGCGR  780
PNYFGVYTRI  TGVISWIQQV  VTHHHHHH                                       808

SEQ ID NO: 98                  moltype = AA  length = 817
FEATURE                        Location/Qualifiers
REGION                         1..817
                               note = source = /note="Description of Artificial Sequence:
                                  Synthetic polypeptide"
source                         1..817
                               mol_type = protein
                               organism = synthetic construct
SEQUENCE: 98
MPRCFQLPCS  TRMPTTEVPQ  AADGQGDAGD  GEEAAEPEGK  FKPPKNTKRK  NRDYVRFTPL   60
LLVLAALVSA  GVMLWYFLGY  KAEVTVSQVY  SGSLRVLNRH  FSQDLGRRES  IAFRSESAKA  120
QKMLQELVAS  TRLGTYYNSS  SVYSFGEGPL  TCFFWFILDI  PEYQRLTLSP  EVVRELLVDE  180
LLSNSSTLAS  YKTEYEVDPE  GLVILEASVN  DIVVLNSTLG  CYRYSYVNPG  QVLPLKGPDQ  240
QTTSCLWHLQ  GPEDLMIKVR  LEWTRVDCRD  RVAMYDAAGP  LEKRLITSVY  GCSRQEPVME  300
VLASGSVMAV  VWKKGMHSYY  DPFLLSVKSV  AFQDCQVNLT  LEGRLDTQGF  LRTPYYPSYY  360
SPSTHCSWHL  TVPSLDYGLA  LWFDAYALRR  QKYNRLCTQG  QWMIQNRRLC  GFRTLQPYAE  420
RIPMVASDGV  TINFTSQISL  TGPGVQVYYS  LYNQSDPCPG  EFLCSVNGLC  VPACDGIKDC  480
PNGLDERNCV  CRAMFQCQED  STCISLPRVC  DRQPDCLNGS  DEEQCQEGVP  CGTFTFQCED  540
RSCVKKPNPE  CDGQSDCRDG  SDEQHCDCGL  QGLSSRIVGG  TVSSEGEWPW  QASLQIRGRH  600
ICGGALIADR  WVITAAHCFE  DSMASPKLW   TVFLGKMRQN  SRWPGEVSFK  VSRLFLHPYH  660
EEDSHDYDVA  LLQLDHPVVY  SATVRPVCLP  ARSHFFEPGQ  HCWITGWGAQ  REGGPVSNTL  720
QKVDVQLVPQ  DLCSEAYRYQ  VSPRMLCAGY  RKGKKDACQG  DSGGPLVCRE  PSGRWFLAGL  780
VSWGLGCGRP  NFFGVYTRVT  RVINWIQQVL  THHHHHH                            817

SEQ ID NO: 99                  moltype = AA  length = 806
FEATURE                        Location/Qualifiers
REGION                         1..806
                               note = source = /note="Description of Artificial Sequence:
                                  Synthetic polypeptide"
source                         1..806
                               mol_type = protein
                               organism = synthetic construct
SEQUENCE: 99
MPVAKAPQVA  GGQGDGGDGE  EAEPEGMFEA  CEDSKRKARG  YLRLAPLWLT  LVVLTSVGVL   60
LWYFLGYKAE  VTVSQVYSGS  LRVLNRHFSQ  DLTRRESSAF  RSETAKAQKM  LKELIASTRL  120
GTYYNSSSVY  SFGEGPLTCF  FWFILQIPEH  RRLMLSPEVV  QALLVEELLS  TVNSSAAVPY  180
```

```
RAEYEVDPEG LVILEASVKD IAALNSTLGC YRYSYVGQGQ VLRLKGPDHL ASSCLWHLQG    240
PEDLMLKLRL EWTLAECRDR LAMYDVAGPL EKRLITSVYG CSRQEPVVEV LASGAIMAVV    300
WKKGLHSYYD PFMLSVQSVV FQACEVNLTL DDRLDSQGVL STPYFPSYYS PRTHCSWHLT    360
VPSLDYGLAL WFDAYALRRQ KYDLPCTQGQ WTIQNRRLCG LRILQPYAER IPVVATAGIT    420
INFTSQISLT GPGVRVHYGL YNQSDPCPGE FLCSVNGLCV PACDGVKDCP NGLDERNCVC    480
RATFQCQEDS TCISLLKVCD GQPDCLNGSD EERCQEGVPC GTFTFQCEDQ SCVKKPNPQC    540
DGRPDCRDGS DEQHCDCGLQ GPSSRIVGGA VSSEGEWPWQ ASLQVRGRHI CGGALIADRW    600
VITAAHCFQE DSMASPALWT VFLGKVWQNS RWPGEVSFKV SRLLLHPYHE EDSHDYDVAL    660
LQLDHPVVRS AAVRPVCLPA RSHFFEPGLH CWITGWGALR EGGPTSNALQ KVDVQLIPQD    720
LCSEAYRYQV TPRMLCAGYR KGKKDACQGD SGGPLVCKAL SGRWFLAGLV SWGLGCGRPN    780
YFGVYTRITG VIGWIQQVVT HHHHHH                                        806

SEQ ID NO: 100           moltype = AA  length = 860
FEATURE                  Location/Qualifiers
REGION                   1..860
                         note = source = /note="Description of Artificial Sequence:
                         Synthetic polypeptide"
source                   1..860
                         mol_type = protein
                         organism = synthetic construct
SEQUENCE: 100
MGSDRARKGG GGPKDFGAGL KYNSRHEKVN GLEEGVEFLP VNNVKKVEKH GPGRWVVLAA    60
VLIGLLLVLL GIGFLVWHLQ YRDVRVQKVF NGYMRITNEN FVDAYENSNS TEFVSLASKV   120
KDALKLLYSG VPFLGPYHKE SAVTAFSEGS VIAYYWSEFS IPQHLVEEAE RVMAEERVVM   180
LPPRARSLKS FVVTSVVAFP TDSKTVQRTQ DNSCSFGLHA RGVELMRFTT PGFPDSPYPA   240
HARCQWALRG DADSVLSLTF RSFDLASCDE RGSDLVTVYN TLSPMEPHAL VQLCGTYPPS   300
YNLTFHSSQN VLLITLITNT ERRHPGFEAT FFQLPRMSSC GGRLRKAQGT FNSPYYPGHY   360
PPNIDCTWNI EVPNNQHVKV RFKFFYLLEP GVPAGTCPKD YVEINGEKYC GERSQFVVTS   420
NSNKITVRFH SDQSYTDTGF LAEYLSYDSS DPCPGQFTCR TGRCIRKELR CDGWADCTDH   480
SDELNCSCDA GHQFTCKNKF CKPLFWVCDS VNDCGDNSDE QGCSCPAQTF RCSNGKCLSK   540
SQQCNGKDDC GDGSDEASCP KVNVVTCTKH TYRCLNGLCL SKGNPECDGK EDCSDGSDEK   600
DCDCGLRSFT RQARVVGGTD ADEGEWWQVS LHALGQGHIC GASLISPNWL VSAAHCYIDD   660
RGFRYSDPTQ WTAFLGLHDQ SQRSAPGVQE RRLKRIISHP FFNDFTFDYD IALLELEKPA   720
EYSSMVRPIC LPDASHVFPA GKAIWVTGWG HTQYGGTGAL ILQKGEIRVI NQTTCENLLP   780
QQITPRMMCV GFLSGGVDSC QGDSGGPLSS VEADGRIFQA GVVSWGDGCA QRNKPGVYTR   840
LPLFRDWIKE NTGVHHHHHH                                               860

SEQ ID NO: 101           moltype = AA  length = 849
FEATURE                  Location/Qualifiers
REGION                   1..849
                         note = source = /note="Description of Artificial Sequence:
                         Synthetic polypeptide"
source                   1..849
                         mol_type = protein
                         organism = synthetic construct
SEQUENCE: 101
MDKENSDVSA APADLKISNI SVQVVSAQKK LPVRRPPLPG RRLPLPGRRP PQRPIGKAKP    60
KKQSKKKVPF WNVQNKIILF TVFLFILAVI AWTLLWLYIS KTESKDAFYF AGMFRITNIE   120
FLPEYRQKES REFLSVSRTV QQVINLVYTT SAFSKFYEQS VVADVSSNNK GGLLVHFWIV   180
FVMPRAKGHI FCEDCVAAIL KDSIQTSIIN RTSVGSLQGL AVDMDSVVLN AGLRSDYSST   240
IGSDKGCSQY FYAEHLSLHY PLEISAASGR LMCHFKLVAI VGYLIRLSIK SIQIEADNCV   300
TDSLTIYDSL LPIRSSILYR ICEPTRTLMS FVSTNNLMLV TFKSPHIRRL SGIRAYFEVI   360
PEQKCENTVL VKDITGFEGK ISSPYYPSYY PPKCKCTWKF QTSLSTLGIA LKFYNYSITK   420
KSMKGCEHGW WEINEHMYCG SYMDHQTIFR VPSPLVHIQL QCSSRLSDKP LLAEYGSYNI   480
SQPCPVGSFR CSSGLCVPQA QRCDGNDCF DESDELFCVS PQPACNTSSF RQHGPLICDG   540
FRDCENGRDE QNCTQSIPCN NRTFKCGNDI CFRKQNAKCD GTVDCPDGSD EEGCTCSRSS   600
SALHRIIGGT DTLEGGWPWQ VSLHFVGSAY CGASVISREW LLSAAHCFHG NRLSDPTPWT   660
AHLGMYVQGN AKFVSPVRRI VVHEYYNSQT FDYDIALLQL SIAWPETLKQ LIQPICIPPT   720
GQRVRSGEKC WVTGWGRRHE ADNKGSLVLQ QAEVELIDQT LCVSTYGIIT SRMLCAGIMS   780
GKRDACKGDS GGPLSCRRKS DGKWILTGIV SWGHGSGRPN FPGVYTRVSN FVPWIHKYVP   840
SLLHHHHHH                                                           849

SEQ ID NO: 102           moltype = AA  length = 783
FEATURE                  Location/Qualifiers
REGION                   1..783
                         note = source = /note="Description of Artificial Sequence:
                         Synthetic polypeptide"
source                   1..783
                         mol_type = protein
                         organism = synthetic construct
SEQUENCE: 102
MDMRVPAQLL GLLLLWLPGA RGADIGYKAE VMVSQVYSGS LRVLNRHFSQ DLTRRESSAF    60
RSETAKAQKM LKELITSTRL GTYYNSSSVY SFGEGPLTCF FWFILQIPEH RRLMLSPEVV   120
QALLVEELLS TVNSSAAVPY RAEYEVDPEG LVILEASVKD IAALNSTLGC YRYSYVGQGQ   180
VLRLKGPDHL ASSCLWHLQG PKDLMLKLRL EWTLAECRDR LAMYDVAGPL EKRLITSVYG   240
CSRQEPVVEV LASGAIMAVV WKKGLHSYYD PFVLSVQPVV FQACEVNLTL DNRLDSQGVL   300
STPYFPSYYS PQTHCSWHLT VPSLDYGLAL WFDAYALRRQ KYDLPCTQGQ WTIQNRRLCG   360
LRILQPYAER IPVVATAGIT INFTSQISLT GPGVRVHYGL YNQSDPCPGE FLCSVNGLCV   420
PACDGVKDCP NGLDERNCVC RATFQCKEDS TCISLPKVCD GQPDCLNGSD EEQCQEGVPC   480
```

```
GTFTFQCEDR  SCVKKPNPQC  DGRPDCRDGS  DEEHCDCGLQ  GPSSRIVGGA  VSSEGEWPWQ   540
ASLQVRGRHI  CGGALIADRW  VITAAHCFQE  DSMASTVLWT  VFLGKVWQNS  RWPGEVSFKV   600
SRLLLHPYHE  EDSHDYDVAL  LQLDHPVVRS  AAVRPVCLPA  RSHFFEPGLH  CWITGWGALR   660
EGGPISNALQ  KVDVQLIPQD  LCSEVYRYQV  TPRMLCAGYR  KGKKDACQGD  SGGPLVCKAL   720
SGRWFLAGLV  SWGLGCGRPN  YFGVYTRITG  VISWIQQVVT  GGGGSGGGGS  GGGGSDYKDD   780
DDK                                                                     783
```

What is claimed is:

1. An anti-type II transmembrane serine protease 6 (TMPRSS6) antibody comprising: a heavy chain complementarity-determining region 1 (HC CDR1) comprising the amino acid sequence of SEQ ID NO: 52, a HC CDR2 comprising the amino acid sequence of SEQ ID NO: 53, a HC CDR3 comprising the amino acid sequence of SEQ ID NO: 54; and a light chain complementarity-determining region 1 (LC CDR1) comprising the amino acid sequence of SEQ ID NO: 57, a LC CDR2 comprising the amino acid sequence of SEQ ID NO: 58, and a LC CDR3 comprising the amino acid sequence of SEQ ID NO: 59.

2. The anti-TMPRSS6 antibody of claim 1, wherein the antibody is a humanized antibody.

3. The anti-TMPRSS6 antibody of claim 1, wherein the HC CDR1, HC CDR2, HC CDR3, LC CDR1, LC CDR2, and LC CDR3 are grafted into a framework comprising variable regions derived from a human immunoglobulin framework.

4. The anti-TMPRSS6 antibody of claim 1, wherein the antibody comprises a heavy chain variable region (VH) comprising the amino acid sequence of SEQ ID NO: 51.

5. The anti-TMPRSS6 antibody of claim 1, wherein the antibody comprises a light chain variable region (VL) comprising the amino acid sequence of SEQ ID NO: 56.

6. The anti-TMPRSS6 antibody of claim 4, wherein the antibody comprises a light chain variable region (VL) comprising the amino acid sequence of SEQ ID NO: 56.

7. The anti-TMPRSS6 antibody of claim 1, wherein the antibody is a full-length antibody, a Fab fragment, or a single-chain variable fragment (scFv).

8. The anti-TMPRSS6 antibody of claim 1, wherein the antibody comprises a heavy chain constant region of IgG1.

9. The anti-TMPRSS6 antibody of claim 1, wherein the antibody comprises a heavy chain comprising the amino acid sequence of SEQ ID NO: 81.

10. The anti-TMPRSS6 antibody of claim 1, wherein the antibody comprises a light chain comprising the amino acid sequence of SEQ ID NO: 83.

11. The anti-TMPRSS6 antibody of claim 9, wherein the antibody comprises a light chain comprising the amino acid sequence of SEQ ID NO: 83.

12. The anti-TMPRSS6 antibody of claim 1, wherein the antibody cross-reacts with at least one non-human TMPRSS6.

13. The anti-TMPRSS6 antibody of claim 12, wherein the non-human TMPRSS6 is a mouse TMPRSS6 or a non-human primate TMPRSS6.

14. The anti-TMPRSS6 antibody of claim 1, wherein the antibody specifically binds to human TMPRSS6.

15. The anti-TMPRSS6 antibody of claim 1, wherein the antibody does not specifically bind to human matriptase-1 or human matriptase-3.

16. A composition comprising the anti-TMPRSS6 of claim 1 and a pharmaceutically acceptable carrier.

17. A composition comprising the anti-TMPRSS6 of claim 6 and a pharmaceutically acceptable carrier.

18. A composition comprising the anti-TMPRSS6 of claim 11 and a pharmaceutically acceptable carrier.

19. An isolated nucleic acid encoding the heavy chain variable region and/or the light chain variable region of the antibody of claim 6.

20. An isolated nucleic acid encoding the heavy chain and/or the light chain of the antibody of claim 11.

21. The isolated nucleic acid of claim 19, wherein the isolate nucleic acid comprises the sequence of SEQ ID NO: 82.

22. The isolated nucleic acid of claim 19, wherein the isolated nucleic acid comprises the sequence of SEQ ID NO: 84.

23. The isolated nucleic acid of claim 20, wherein the isolated nucleic acid comprises the sequence of SEQ ID NO: 84.

24. A vector comprising the isolated nucleic acid of claim 20.

25. A host cell comprising the vector of claim 24.

* * * * *